(12) United States Patent
Ibrahim et al.

(10) Patent No.: US 11,660,099 B2
(45) Date of Patent: May 30, 2023

(54) MEDICAL DEVICES

(71) Applicant: AtriCure, Inc., West Chester, OH (US)

(72) Inventors: Tamer Ibrahim, Danville, CA (US); Kenneth L. Miller, Hamilton, OH (US); Michael Hooven, Cincinnati, OH (US); Dwight Morejohn, Davis, CA (US)

(73) Assignee: AtriCure, Inc., West Chester, OH (US)

( * ) Notice: Subject to any disclaimer, the term of this patent is extended or adjusted under 35 U.S.C. 154(b) by 625 days.

(21) Appl. No.: 16/749,429

(22) Filed: Jan. 22, 2020

(65) Prior Publication Data

US 2020/0261096 A1 Aug. 20, 2020

Related U.S. Application Data

(63) Continuation of application No. 15/051,363, filed on Feb. 23, 2016, now Pat. No. 10,548,611.
(Continued)

(51) Int. Cl.
*A61B 17/128* (2006.01)
*A61B 17/02* (2006.01)
(Continued)

(52) U.S. Cl.
CPC ............ *A61B 17/1285* (2013.01); *A61B 1/00* (2013.01); *A61B 1/018* (2013.01);
(Continued)

(58) Field of Classification Search
CPC ....... A61B 17/1285; A61B 1/00; A61B 1/018; A61B 17/0218; A61B 17/3421; A61B 17/50; A61B 17/52; A61B 18/1492; A61B 90/37; A61B 1/00082; A61B 1/00089; A61B 1/00135; A61B 17/12099; A61B 17/12122; A61B 17/122; A61B 18/0218; A61B 90/30; A61B 2017/00243; A61B 2017/00309; A61B 2017/00314; A61B 2017/00336; A61B 2017/00477; A61B 2017/00876; A61B 2017/0225; A61B 2017/12054; A61B 2017/308; A61B 2017/320044; A61B 2017/3425;
(Continued)

(56) References Cited

U.S. PATENT DOCUMENTS

| | | |
|---|---|---|
| 4,509,517 A | 4/1985 | Zibelin |
| 4,811,735 A | 3/1989 | Nash |

(Continued)

*Primary Examiner* — Robert A Lynch
*Assistant Examiner* — Mikail A Mannan
(74) *Attorney, Agent, or Firm* — Dykema Gossett PLLC

(57) ABSTRACT

In at least one embodiment, a medical device can comprise an elongate outer sheath that extends along a sheath longitudinal axis and defines a central lumen extending therethrough, the elongate outer sheath can comprise a proximal sheath portion and a distal sheath portion. A first guidewire can comprise a first guidewire end and a second guidewire end, the first guidewire can extend from the first and second guidewire ends through the central lumen and can form a distal looped portion. An occlusion device can be disposed at a distal end of an elongate flexible shaft. The elongate flexible shaft can extend from the proximal sheath portion through the central lumen. The occlusion device can include a guide lumen through which the first guide wire passes.

17 Claims, 42 Drawing Sheets

Related U.S. Application Data

(60) Provisional application No. 62/119,800, filed on Feb. 23, 2015.

(51) Int. Cl.

| | | |
|---|---|---|
| *A61B 1/018* | (2006.01) | |
| *A61B 90/00* | (2016.01) | |
| *A61B 18/14* | (2006.01) | |
| *A61B 17/50* | (2006.01) | |
| *A61B 1/00* | (2006.01) | |
| *A61B 17/52* | (2006.01) | |
| *A61B 17/34* | (2006.01) | |
| *A61B 17/12* | (2006.01) | |
| *A61B 17/122* | (2006.01) | |
| *A61B 17/00* | (2006.01) | |
| *A61B 17/32* | (2006.01) | |
| *A61B 18/00* | (2006.01) | |
| *A61B 17/30* | (2006.01) | |
| *A61B 90/30* | (2016.01) | |
| *A61B 18/02* | (2006.01) | |

(52) U.S. Cl.
CPC ...... *A61B 17/0218* (2013.01); *A61B 17/3421* (2013.01); *A61B 17/50* (2013.01); *A61B 17/52* (2013.01); *A61B 18/1492* (2013.01); *A61B 90/37* (2016.02); *A61B 1/00082* (2013.01); *A61B 1/00089* (2013.01); *A61B 1/00135* (2013.01); *A61B 17/122* (2013.01); *A61B 17/12099* (2013.01); *A61B 17/12122* (2013.01); *A61B 18/0218* (2013.01); *A61B 90/30* (2016.02); *A61B 2017/00243* (2013.01); *A61B 2017/00309* (2013.01); *A61B 2017/00314* (2013.01); *A61B 2017/00336* (2013.01); *A61B 2017/00477* (2013.01); *A61B 2017/00876* (2013.01); *A61B 2017/0225* (2013.01); *A61B 2017/12054* (2013.01); *A61B 2017/308* (2013.01); *A61B 2017/320044* (2013.01); *A61B 2017/3425* (2013.01); *A61B 2017/3488* (2013.01); *A61B 2018/00029* (2013.01); *A61B 2018/00267* (2013.01); *A61B 2018/00279* (2013.01); *A61B 2018/00577* (2013.01); *A61B 2090/08021* (2016.02); *A61B 2217/005* (2013.01); *A61B 2218/002* (2013.01); *A61B 2218/007* (2013.01)

(58) Field of Classification Search
CPC .. A61B 2017/3488; A61B 2018/00029; A61B 2018/00267; A61B 2018/00279; A61B 2018/00577; A61B 2090/08021; A61B 2217/005; A61B 2218/002; A61B 2218/007; A61B 1/00071; A61B 1/00066; A61B 1/00112; A61B 1/05; A61B 17/29; A61B 17/2909; A61B 2017/2901; A61B 2017/2926; A61B 2017/2932; A61M 25/01

See application file for complete search history.

(56) References Cited

U.S. PATENT DOCUMENTS

| | | |
|---|---|---|
| 6,371,968 B1 | 4/2002 | Kogasaka et al. |
| 6,537,273 B1 | 3/2003 | Sosiak et al. |
| 2002/0023653 A1 | 2/2002 | Sternman et al. |
| 2004/0117032 A1* | 6/2004 | Roth .................. A61F 2/2427 623/23.72 |
| 2004/0199236 A1 | 10/2004 | Laske |
| 2005/0256507 A1 | 11/2005 | Long |
| 2007/0166345 A1 | 7/2007 | Pavcnik |
| 2008/0312664 A1 | 12/2008 | Bardsley et al. |
| 2010/0145306 A1 | 6/2010 | Mickley et al. |
| 2011/0313242 A1 | 12/2011 | Surti |
| 2012/0035622 A1 | 2/2012 | Kiser et al. |
| 2012/0143177 A1 | 6/2012 | Avitall |
| 2012/0203206 A1 | 8/2012 | Nimkar |
| 2013/0211432 A1 | 8/2013 | Terada et al. |
| 2014/0088684 A1 | 3/2014 | Paskar |
| 2014/0180155 A1 | 6/2014 | Frietag |

* cited by examiner

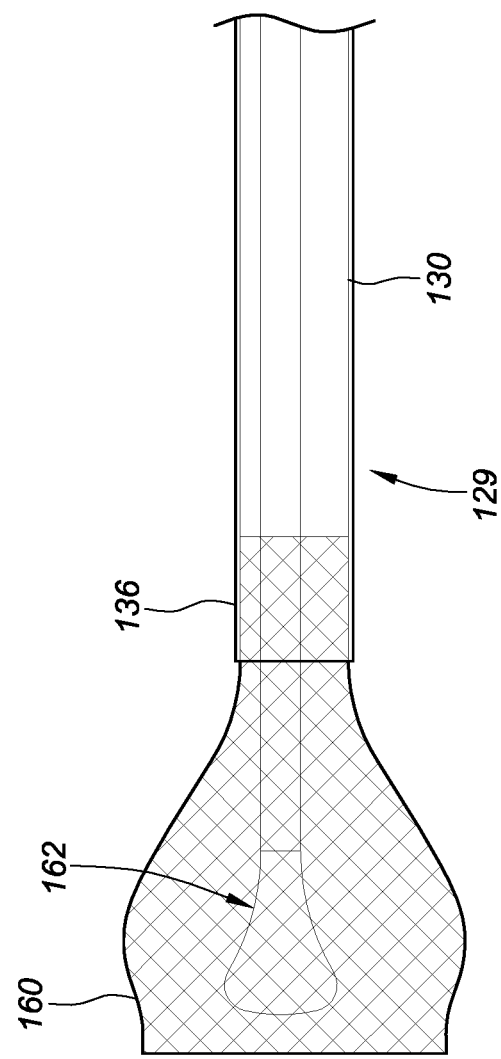

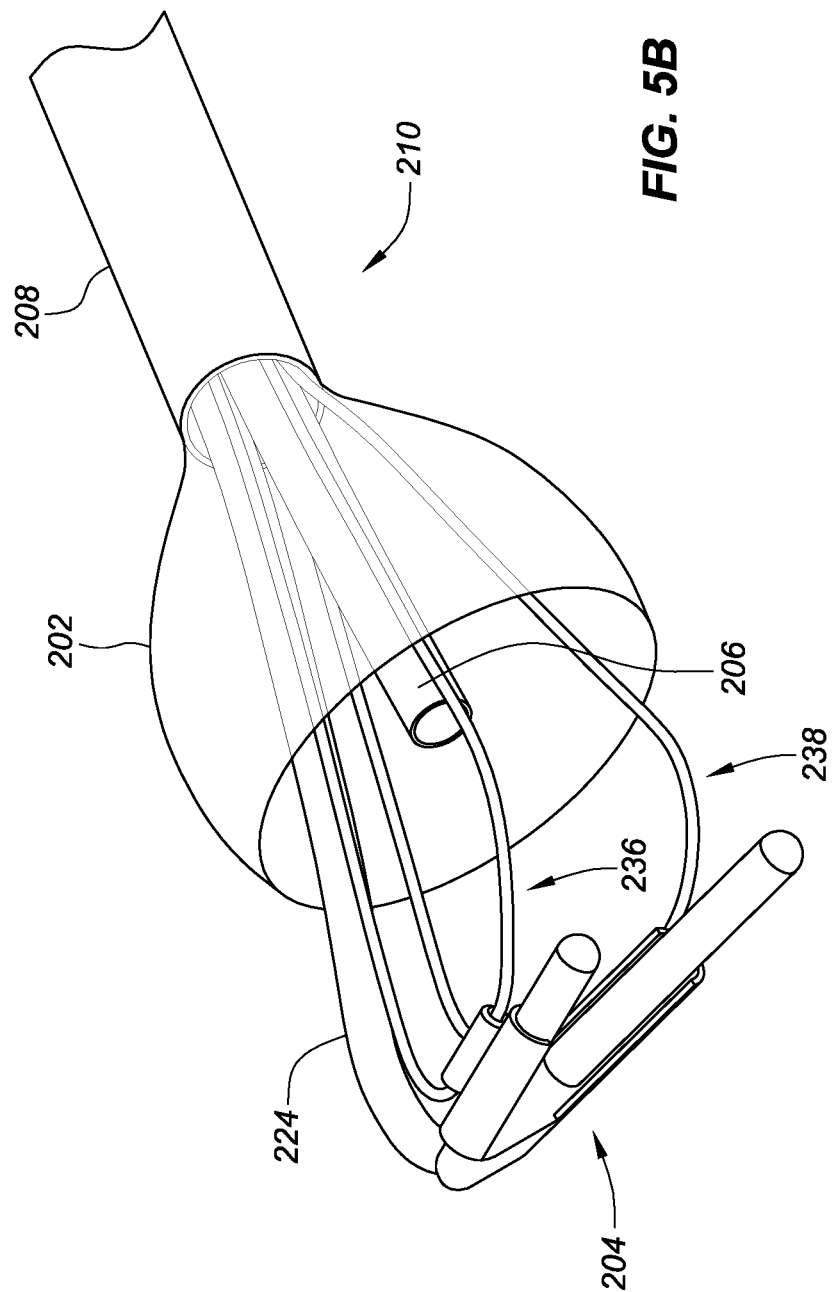

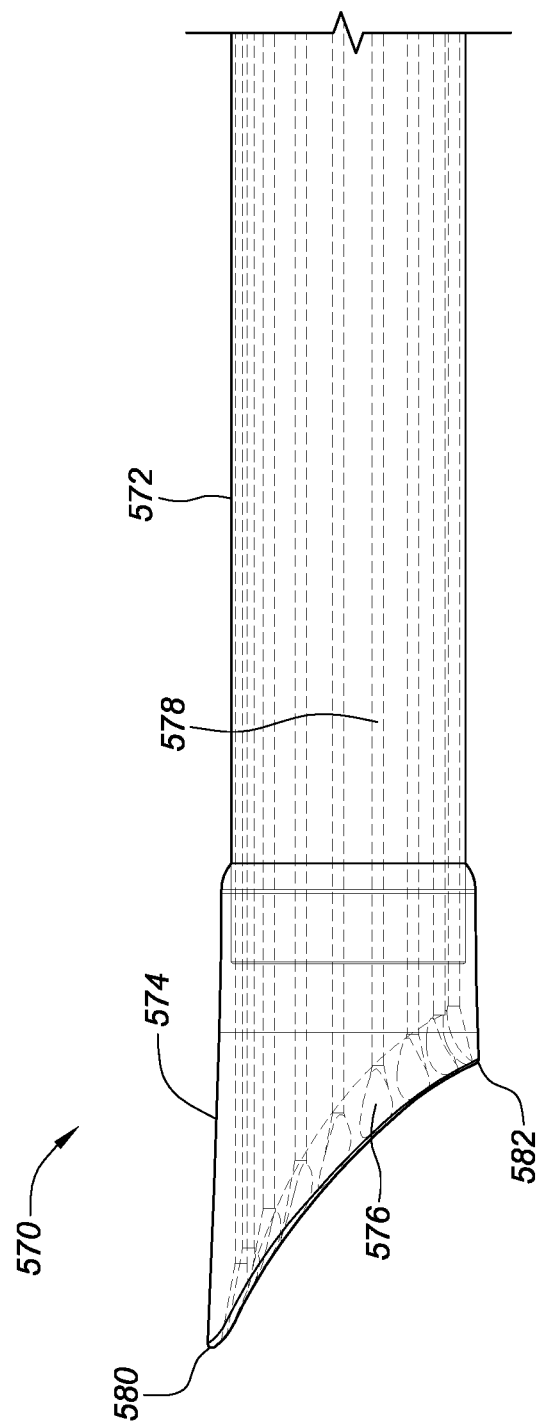

MEDICAL DEVICES

CROSS-REFERENCE TO RELATED APPLICATIONS

This application is a continuation of U.S. application Ser. No. 15/051,363, filed 23 Feb. 2016 (the '363 application), now U.S. Pat. No. 10,548,611, which claims priority to U.S. provisional patent application No. 62/119,800, filed 23 Feb. 2015 the '800 application). The '363 application and the '800 application are both hereby incorporated by reference as though fully set forth herein.

BACKGROUND a. Field

The instant disclosure relates to medical devices.

b. Background Art

Various conditions can affect the heart, which can alter a 'normal' functioning of the heart. Such conditions can include atrial arrhythmias, which include conditions in which an electrical activity of the heart is irregular, faster, or slower than normal. Treatment of atrial arrhythmias can often involve accessing the heart epicardially or endocardially with devices that can aid in detecting and/or treating the arrhythmias.

SUMMARY

In at least one embodiment, a medical device can comprise an elongate outer sheath that extends along a sheath longitudinal axis and defines a central lumen extending therethrough, the elongate outer sheath can comprise a proximal sheath portion and a distal sheath portion. A first guidewire can comprise a first guidewire end and a second guidewire end, the first guidewire can extend from the first and second guidewire ends through the central lumen and can form a distal looped portion. An occlusion device can be disposed at a distal end of an elongate flexible shaft. The elongate flexible shaft can extend from the proximal sheath portion through the central lumen. The occlusion device can include a guide lumen through which the first guide wire passes. The first guidewire can be configured to be moved distally with respect to the outer sheath. The distal looped portion can be disposed distally with respect to the distal sheath portion. The occlusion device can be configured to be moved along the first guidewire.

In at least one embodiment, a medical device can comprise an elongate outer sheath that extends along a sheath longitudinal axis and defines a central lumen extending therethrough, the elongate outer sheath can comprise a proximal sheath portion and a distal sheath portion. A first guidewire can comprise a first guidewire end and a second guidewire end and a second guidewire can comprise a third guidewire end and a fourth guidewire end. The first and second guidewires can extend from their respective guidewire ends through the central lumen and can form a first guidewire distal looped portion and a second guidewire distal looped portion, respectively. An occlusion device can be disposed at a distal end of an elongate flexible shaft, the elongate flexible shaft can extend from the proximal sheath portion through the central lumen. The occlusion device can include a first guide lumen through which the first guidewire passes and a second guide lumen through which the second guidewire passes. The occlusion device can include a first jaw to which the first guide lumen is connected and a second jaw to which the second guide lumen is connected. The first jaw and the second jaw can be connected via a pivot point.

In at least one embodiment, a method of using a medical device can comprise deploying a first guidewire distal looped portion and a second guidewire distal looped portion of the medical device from a distal end of an elongate outer sheath that extends along a sheath longitudinal axis and defines a central lumen extending therethrough. The method can include guiding an occlusion device disposed at a distal end of an elongate flexible shaft along the first guidewire distal looped portion and the second guidewire distal looped portion. The method can include activating the occlusion device via a control disposed proximally of the distal end of the elongate outer sheath.

BRIEF DESCRIPTION OF THE DRAWINGS

FIG. 2C depicts the steerable expanding shroud in a second deployed state and an ablation device extending from a distal end of the expansion catheter associated with the exemplary expansion catheter system in FIG. 1, in accordance with embodiments of the present disclosure.

FIG. 5B depicts the steerable expanding shroud, the occlusion device in a second deployed state, and the visualization device extending from the distal end of the outer sheath comprising part of the expansion catheter, in accordance with embodiments of the present disclosure.

FIG. 14E is a side view of the distal end of the portal access device in FIG. 14B, in accordance with embodiments of the present disclosure.

DETAILED DESCRIPTION

Figure 1:
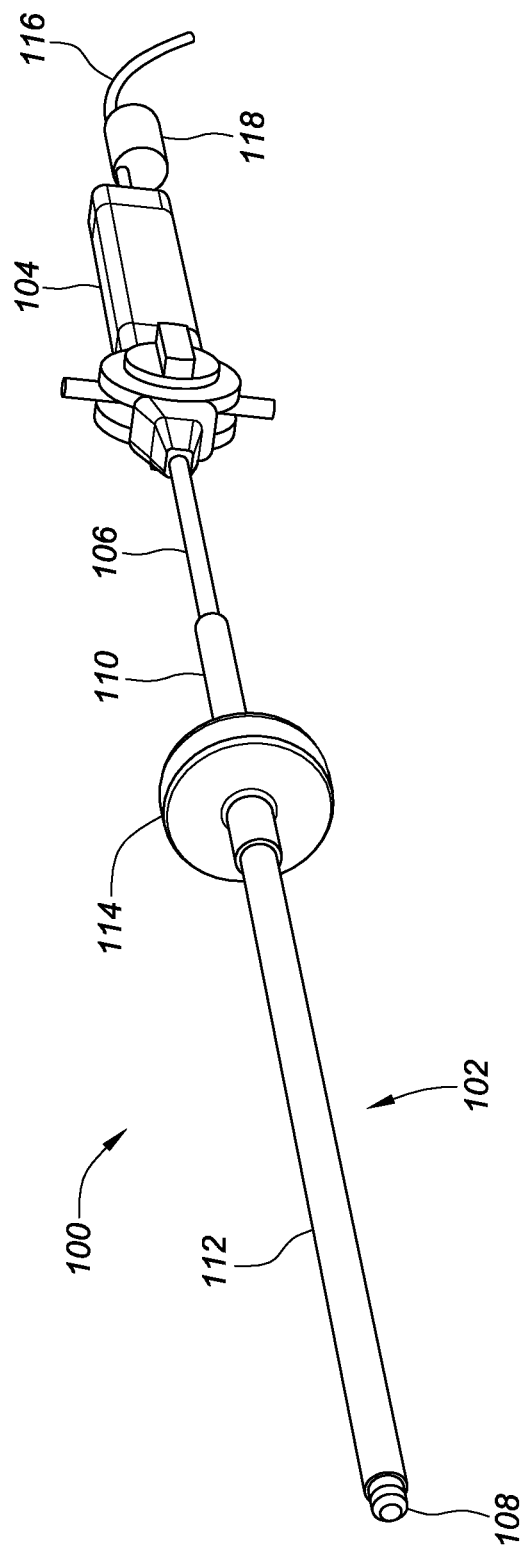
FIG. 1 depicts an expansion catheter system that can be used in relation to cardiac access, visualization, sensing, and/or ablation, in accordance with embodiments of the present disclosure.

FIG. 1 depicts an expansion catheter system 100 that can be used in relation to cardiac access, visualization, and/or ablation, in accordance with embodiments of the present disclosure. In some embodiments of the present disclosure the expansion catheter system 100 can include an expansion catheter 102, a tool (e.g., catheter handle 104 connected to a steerable catheter 106), and endoscope 108. The expansion catheter 102 can have a distal end and a proximal end. The catheter handle 104 can have various componentry included in the catheter handle 104 for control (e.g., deflection of the distal end of the expansion catheter 102). A proximal end of a steerable catheter 106 can be connected with a distal end of the catheter handle 104 and deflection of a distal portion of the steerable catheter 106 can be controlled via the catheter handle 104. For example, approximately the last three inches of the steerable catheter 106 can be controlled via the various componentry included in the catheter handle 104. An inner sheath 110 can be concentric with the steerable catheter 106 and can extend distally over the steerable catheter 106.

In some embodiments, a space can exist between the proximal end of the inner sheath 110 and the distal end of the catheter handle 104, leaving a portion of the steerable catheter 106 exposed. In some embodiments, an outer sheath 112 can be concentric with the inner sheath 110 and can extend distally from and can be connected to a stability handle 114 towards the distal end of the expansion catheter 102. An outer diameter of the inner sheath 110 can be very close to an inner diameter of the outer sheath 112, such that the inner sheath 110 can slide within the outer sheath 112.

In some embodiments, the outer sheath 112 can be an elongate outer sheath 112 that extends along a sheath longitudinal axis and defines a central lumen extending therethrough. The elongate outer sheath 112 can comprise a proximal sheath portion and a distal sheath portion.

As discussed further herein, various devices and associated components can be inserted through the steerable catheter 106 and can be slid axially through the steerable catheter 106, such that the devices can exit through the distal end of the expansion catheter 102. As shown in FIG. 1, an endoscope cable 116 can extend through a proximal end of the catheter handle 104, through the catheter handle 104, through the steerable catheter 106 to the endoscope 108 located in the distal end of the expansion catheter 102. In some embodiments, control circuitry 118 associated with the endoscope 108 can be located proximally with respect to the catheter handle 104. In an example, the endoscope 108 can be a CMOS endoscope.

In some embodiments, the inner sheath 110 can be slid distally with respect to the outer sheath 112, such that a steerable expanding shroud 160 is pushed out of the distal end of the outer sheath 112, as further described herein. A physician can grasp the stability handle 114 to cause the outer sheath 112 to remain stationary with respect to the catheter handle 104. Alternatively, or in addition, the stability handle 114 can be moved proximally with respect to the inner sheath 110 to cause the steerable expanding shroud 160 to be deployed from the distal end of the expansion catheter 102.

Because the distal end of the expansion catheter 102 can be positioned in close relation to a tissue surface, there can be some relative motion occurring between the outer and inner sheath to deploy the steerable expanding shroud 160. In an example, the outer sheath 112 can be pulled back just slightly via the stability handle 114 in concert with pushing the inner sheath 110 distally, which deploys the expansion catheter 100 portion. As the steerable expanding shroud 160 expands, it can naturally pull back. Thus, to keep the distal end of the steerable expanding shroud 160 and the scope in the same spot, the inner sheath 110 can be advanced farther than the outer sheath 112 is retracted. As the steerable expanding shroud 160 is retracted to full diameter by the pull sutures, the whole system may need to be advanced. In some embodiments, the outer sheath 112 can be held still in relation to a patient. In some embodiments, a stationary holding assist device can be utilized to hold the outer sheath 112 in position in relation to a target tissue.

Figure 2A:
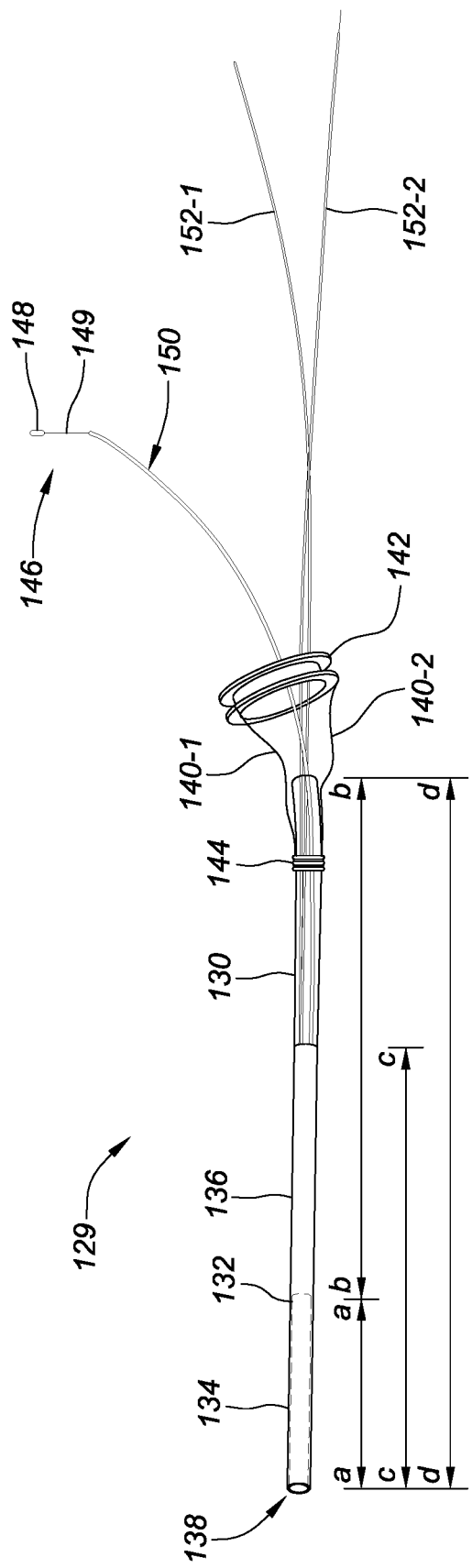
FIG. 2A depicts components comprising part of the exemplary expansion catheter system depicted in FIG. 1, in accordance with embodiments of the present disclosure.

FIG. 2A depicts components associated with the exemplary expansion catheter system 100 in FIG. 1, in accordance with embodiments of the present disclosure. In some embodiments, as described in relation to FIG. 1, various devices and associated components can be inserted through an inner sheath 130. The inner sheath 130 can have a length, defined by line b-b of approximately 25 centimeters, although the inner sheath 130 can be shorter or longer than 25 centimeters. In an example, and as depicted, the inner sheath 130 can be made from a semi-rigid, clear tube. As used herein, a tube can be a hollow cylinder, although the tube can be formed in various other shapes, such as a square, triangle, etc.

The inner sheath 130 can be flexible, such that it can move with the steerable catheter 106 (e.g., can be deflected), depicted in FIG. 1. The inner sheath 130 can be disposed within a central lumen formed by the elongate outer sheath 136 and can be coaxial with the outer sheath 136. In some embodiments, a distal end of the inner sheath 130 can extend proximally to the distal end of the expansion catheter. Located between the distal end of the inner sheath 132 and the distal end of the expansion catheter 129, can be a steerable expanding shroud 160 and/or other devices. For example, the steerable expanding shroud 160 can be located (e.g., stored) in a distal portion 134 of the expansion catheter 129 defined by line a-a. In some embodiments, line a-a can have a length of approximately 9.5 cm, although the distal portion 134 of the expansion catheter 129 that houses the steerable expanding shroud and/or other devices can have a length that is longer or shorter than 9.5 cm.

In some embodiments, an ablation device and/or an occlusion device (e.g., occlusion clip device) can also be inserted inside of the steerable expanding shroud 160, as further described herein. The steerable expanding shroud 160 can be connected to the distal end of the inner sheath 132. In some embodiments, the inner sheath 130 can be configured to axially move with respect to the outer sheath 136. As the inner sheath 130 is moved distally with respect to the outer sheath 136, which can also be made of similar material as the inner sheath 130, the steerable expanding shroud 160 can be forced from the distal end of the outer sheath 138 and can expand, as discussed further herein.

In some embodiments, a length of the outer sheath, defined by line c-c can be approximately 21 centimeters, although the length of the outer sheath can be less than or greater than 21 centimeters. In some embodiments, a length from the distal end of the outer sheath 136 to the proximal end of the inner sheath 130, defined by line d-d, can be approximately 33 centimeters, although the length can be greater than or less than 33 centimeters.

In some embodiments, various other components associated with devices inserted through a central lumen of the inner sheath 130 can also be inserted through the inner sheath 130. For example, sutures 140-1, 140-2 that are connected to a distal end of the steerable expanding shroud 160 can pass through the central lumen of the inner sheath 130 and can be connected to a ring 142 (e.g., control, control ring) or other device which can cause each of the sutures to be tensioned independently from one another. Although two sutures 140-1, 140-2 are depicted, a third suture, a third suture may be used. Hereinafter, sutures 140-1, 140-2 are generally referred herein as sutures 140.

In some embodiments, one or more sutures (e.g., three sutures, four sutures, eight sutures, nine sutures) can be connected to the distal end of the steerable expanding shroud. In some examples, a connection point between each of the sutures 140 and the steerable expanding shroud 160 can be equidistant from one another around a distal circumference of the steerable expanding shroud 160. In some embodiments, one or more o-rings 144 (e.g., frictional engagement devices) can be placed over the inner sheath 130 and positioned distally to a proximal end of the inner sheath 130. One or more suture holes can be formed distally from the o-rings 144, through which the sutures 140 can pass. The sutures 140 can extend from the distal end of the steerable expanding shroud through the central lumen of the inner sheath 130, out of the suture holes and between an outer surface of the inner sheath 130 and an inner surface of the o-rings 144, such that the o-rings 144 provide tension on the sutures. Thus, a tension applied to the sutures via the ring 142 can be maintained via frictional forces enacted by the o-rings 144 on the sutures.

Figure 5A:
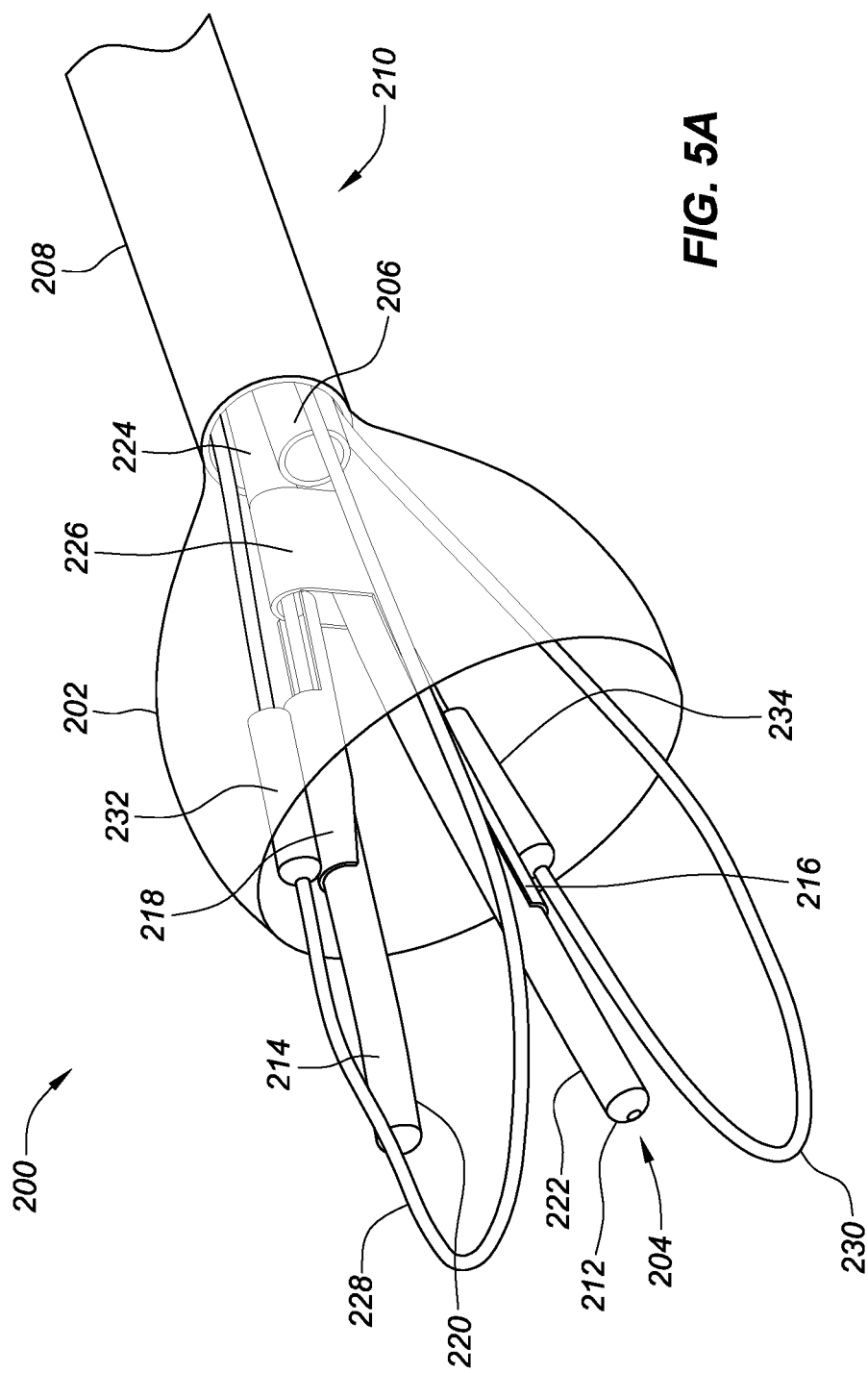
FIG. 5A depicts an embodiment of an expansion catheter system that includes a steerable expanding shroud, an occlusion device in a first deployed state, and a visualization device extending from a distal end of the outer sheath comprising part of the expansion catheter, in accordance with embodiments of the present disclosure.
Figure 5C:
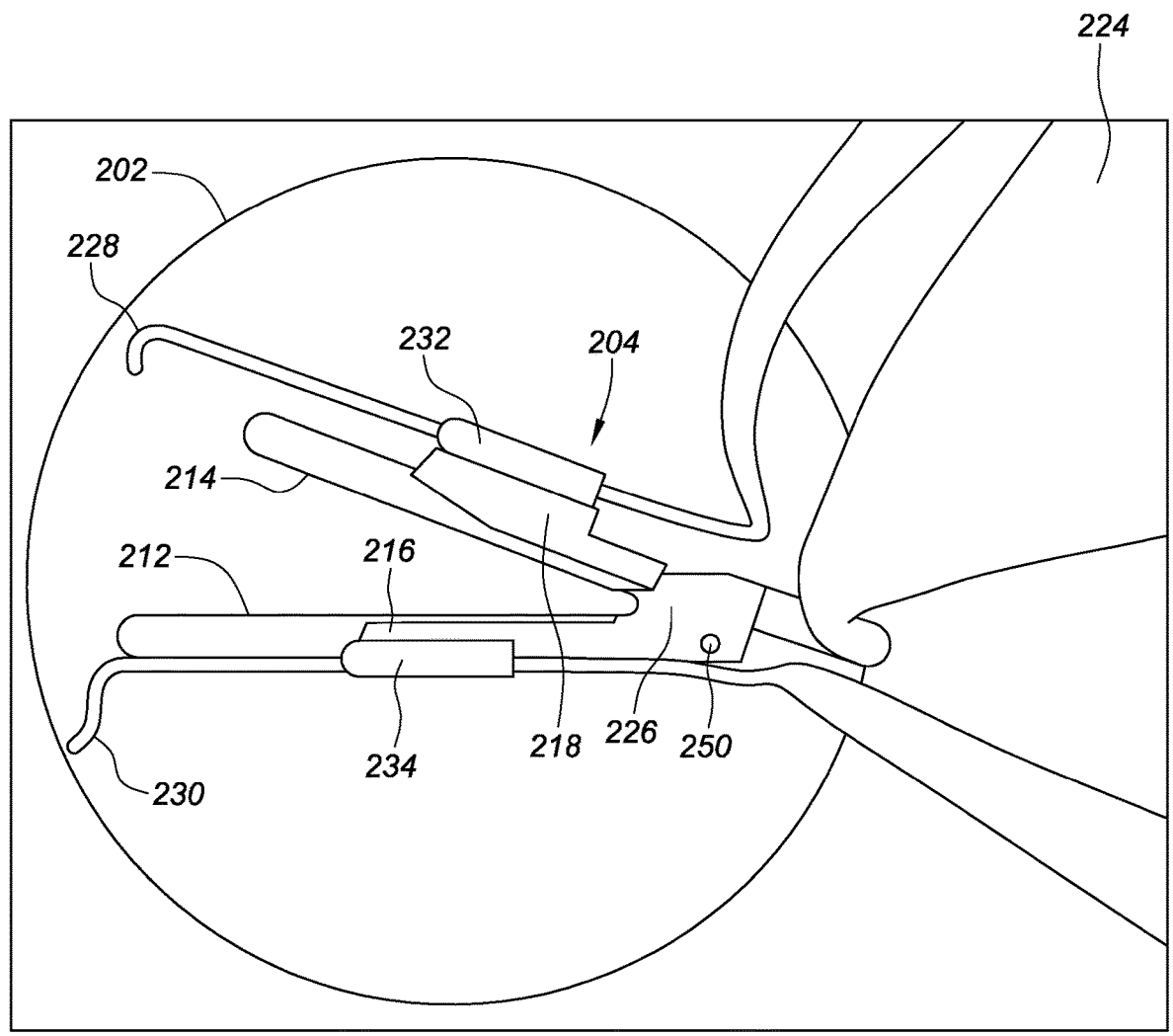
FIG. 5C is a view from the visualization device in FIG. 5B, in accordance with embodiments of the present disclosure.

Additionally, in some embodiments, the occlusion device advancing and opening controls 146 can extend through the central lumen of the inner sheath 130 to an occlusion device inside of the distal end of the outer sheath 136. The occlusion device (or other mechanism) can be deployed from the distal end of the expansion catheter 129 by advancing the push housing (e.g., cable 150 housing) toward the distal end of the expansion catheter 129. In some embodiments, the occlusion device can include jaws, as depicted in FIGS. 5A to 5C. Control of the occlusion device jaws can be provided by regressing a pull knob 148 on the cable 149 proximally. For example, the cable 149 can be connected to the occlusion device 204 and can be pulled and/or pushed to open and/or close the jaws associated with the occlusion device 204. In some embodiments, the cable housing can counter the force applied to the cable 149 and can provide a lumen through which the cable 149 can pass.

In some embodiments, guidewire rails 152-1, 152-2, further depicted in relation to FIGS. 5A to 5C for example, can extend through the central lumen of the inner sheath 130 to a distal end of the expansion catheter 129 to provide for control and/or positioning of various devices included in or near the distal end of the expansion catheter 129. In some embodiments, a proximal end of the steerable expanding shroud 160 can extend further proximally down the outer sheath, resulting in a longer steerable expanding shroud, which can form a tunnel that is longer and/or larger in diameter. In some embodiments, a longer steerable expanding shroud can form a tunnel that extends from a patient's heart to a position that is outside of the patient's body. In some embodiments, a longer steerable expanding shroud can be more flexible than a shorter steerable expanding shroud, which can accommodate to an anatomy better than a straight or fixed curved shaft.

In some embodiments, cuts can be made across a portion (e.g., distal end) of the inner sheath 130 and/or outer sheath 136. In some embodiments, the cuts can be perpendicular to a longitudinal axis of the inner sheath 130 and/or outer sheath 136. In some embodiments, cuts can be made on each side of the inner sheath 130 and/or outer sheath 136, such that the cuts are diametrically opposed to one another, which leaves two spines that are diametrically opposed to one another that run along the inner sheath 130 and/or outer sheath 136 axially. In some embodiments, 20 to 35 cuts can be made in the most distal three inches of the inner sheath 130 and/or outer sheath 136, although more cuts or fewer cuts can be made. The cuts can allow either the inner sheath 130 and/or outer sheath 136 to flex more easily and/or flex in a single plane.

In some embodiments, the inner sheath 130 and/or outer sheath 136 can be passively flexible and steered with a deflectable shaft (e.g., steerable catheter 106) passing through the inner sheath 130. Alternatively, pull members (e.g., wires) can be attached to a distal end of the inner sheath 130, which can cause the distal end of the expansion catheter 129 to deflect when tension is applied to one or more of the pull members. In some embodiments, a ribbon can be attached to the distal end of the inner sheath 130, which can cause the distal end of the expansion catheter 129 to deflect when tension is applied to one or more of the pull members. In an example, ribbons can be used to increase tensile strength without adding significantly to diameter requirements.

In some embodiments, when the axially perpendicular cuts are made in both the inner and/or outer sheath 130, 136, the cuts can interfere with each other and cause friction between the sheaths 130, 136, when the sheaths 130, 136 are deflected and/or rotated about the longitudinal axis. As such, one of the inner and/or outer sheath 130, 136 can have longitudinal cuts that extend along a longitudinal axis and are perpendicular to the axially perpendicular cuts. In some embodiments, one of the inner sheath 130 and/or outer sheath 136 can have alternating axial and axially perpendicular cuts. For example, a first set of cuts can be diametrically opposed to each other and can be axially perpendicular, a next adjacent set of cuts can be diametrically opposed to one another and can extend axially, followed by another set of cuts that are diametrically opposed to each other and are axially perpendicular. This pattern can continue along a particular length of at least one of the inner and outer sheath.

Figure 2B:
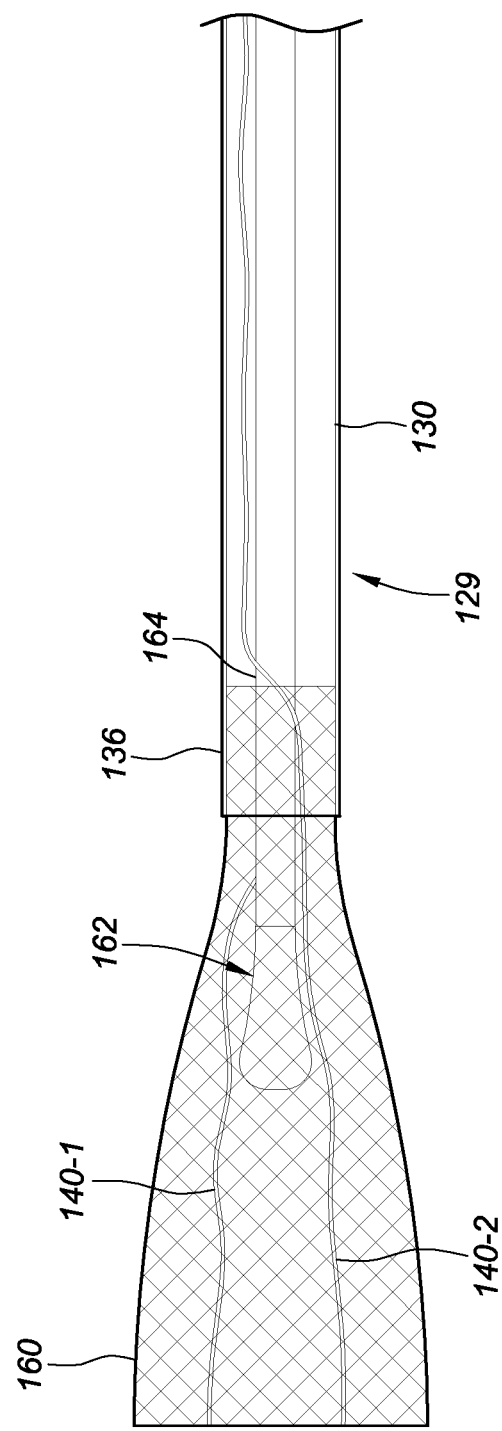
FIG. 2B is a fragmentary, isometric view of a steerable expanding shroud extending from an inner sheath that is slidingly mounted in an outer sheath, and shows the steerable expanding shroud in a first deployed state and an ablation device extending from the distal end of an expansion catheter associated with the exemplary expansion catheter system in FIG. 1, in accordance with embodiments of the present disclosure.

In some embodiments, the inner sheath 130 and/or outer sheath 136 can have diametrically opposed sets of cuts that are perpendicular to a longitudinal axis of the inner sheath 130 and/or outer sheath 136, with each adjacent set of cuts being disposed at 90 degrees with respect to one another. As such, interference between the inner sheath 130 and outer sheath 136 can be avoided because the rotationally alternating diametrically opposed perpendicular sets of cuts allow for the inner sheath 130 and/or outer sheath 136 to deflect in any direction (e.g., plane), thus avoiding interference when the inner sheath 130 and/or outer sheath 136 are configured to deflect within one deflection plane, and a deflection plane of the inner sheath 130 is perpendicular to a deflection plane of the outer sheath 136. In some embodiments, the inner and outer sheath may be comprised of flexible material without cuts and can FIG. 2B is a fragmentary, isometric view of a steerable expanding shroud 160 extending from an inner sheath 130 that is slidingly mounted in an outer sheath 136, and shows the steerable expanding shroud 160 in a first deployed state and an ablation device 162 extending from the distal end of an expansion catheter 129 associated with the exemplary expansion catheter system 100 depicted in FIG. 1, in accordance with embodiments of the present disclosure. In some embodiments, the ablation device 162 can be an occlusion device. As depicted in FIG. 2B, the steerable expanding shroud 160 has been pushed from the distal end of the outer sheath 136 by the inner sheath 130, to which the steerable expanding shroud is connected. As the steerable expanding shroud 160 exits the distal end of the outer sheath 136, the steerable expanding shroud 160 can expand.

In some embodiments, the steerable expanding shroud 160 can be made from woven nitinol wire, which can maintain a preformed shape. However, the steerable expanding shroud 160 can be formed from other materials. In some embodiments, when the steerable expanding shroud 160 is placed within (e.g., retracted into) the distal end of the expansion catheter 129, the steerable expanding shroud 160 can lengthen as the woven nitinol wire is compressed. As such, when the steerable expanding shroud 160 is deployed from the distal end of the expansion catheter 129, an overall length of the steerable expanding shroud 160 can shorten somewhat. As depicted in FIG. 2B, no tension is applied to the sutures 140-1, 140-2, resulting in the steerable expanding shroud 160 having no deflection with respect to a longitudinal axis running along the expansion catheter 129.

In some embodiments, the device 162 extending from the distal end of the expansion catheter 129 can be an ablation device, visualization device, and/or other type of device. The device 162 can have a tether 164, which can be connected to a proximal end of the device 162 and can extend proximally through the expansion catheter 129. In an example, the tether 164 can be a cable that includes a power and/or control wire. In some embodiments, the tether 164 can be semi-rigid, such that a force can be applied to a proximal end of the tether 164, which can be transferred through the tether 164 to the device 162, thus moving the device 162 proximally and/or distally. In some embodiments, and as depicted in FIG. 2B, the device 162 can be connected to a distal end of a steerable catheter 129. In some embodiments, the steerable catheter 126 can be approximately 12 French and can be deflectable along a distal portion (e.g., 4 to 5 centimeters).

In some embodiments, the expansion catheter system 100 can be used to introduce a device 162 into the interstitial space between the pericardial sac of the heart and the myocardium of the heart. The distal end of expansion catheter 129 can be introduced through the pericardial sac at or near an apex of the heart (e.g., subxiphoid) and the steerable expanding shroud 160 can be deployed. Upon deployment of the steerable expanding shroud 160, a tunnel can be created between the circumferential walls of the steerable expanding shroud 160, creating space for a device to operate in. For example, where the device 162 is an endoscope, the lens can be kept clear of tissues/fluid and the field of view can be enlarged by the steerable expanding shroud 160. Likewise, where the device is an ablation device, tissues that are not involved with a therapy applied by the ablation device can be kept clear along with fluid. In some embodiments, an irrigation tube can also extend down a central lumen of the expansion catheter 129 and/or a lumen created by the steerable expanding shroud 160 and can apply irrigation fluid to the site where the ablation device is operating.

FIG. 2C depicts the steerable expanding shroud 160 in a second deployed state and the device 162 extending from a distal end of the expansion catheter 129 associated with the exemplary expansion catheter system 100 in FIG. 1, in accordance with embodiments of the present disclosure. As depicted, the device 162 has remained in approximately the same place as shown in FIG. 2B, while the steerable expanding shroud 160 has been retracted proximally through a tension that has been approximately equally applied to the sutures 140 (e.g., via ring 142). As can be seen, the suture 140 running through a central lumen of the expansion catheter 129, which can be defined by the inner sheath 130, is now taught due to the tension applied to the suture via, for example, the ring 142, depicted in FIG. 2A. In addition, the outer sheath 136 and inner sheath 130 have remained in approximately the same position with respect to one another.

In some embodiments, retracting the steerable expanding shroud 160 can cause a diameter created by the steerable expanding shroud 160 to increase, as seen in FIG. 2C, which can create more room for devices to operate. In addition, as the steerable expanding shroud 160 is retracted, as depicted in FIG. 2C, the woven fibers of the steerable expanding shroud 160 can become more circumferential, which can cause the woven walls of the steerable expanding shroud 160 to become more rigid. For example, the woven walls of the steerable expanding shroud 160 can become more resistant to deflecting inward towards a lumen formed by the steerable expanding shroud 160 when a force is applied to an outer portion of the woven walls of the steerable expanding shroud 160.

In some embodiments, the steerable expanding shroud 160 can include a rigid and/or semi-rigid ring that extends around a distal most portion of the steerable expanding shroud 160. For example, the ring can be interwoven between fibers of the woven steerable expanding shroud 160. As such, tension applied to the sutures 140 can be directly translated to the interwoven ring, resulting in a more consistent application of force around a distal circumference of the steerable expanding shroud 160. In some embodiments, the sutures can be attached directly to the fibers of the woven steerable expanding shroud 160.

Figure 3:
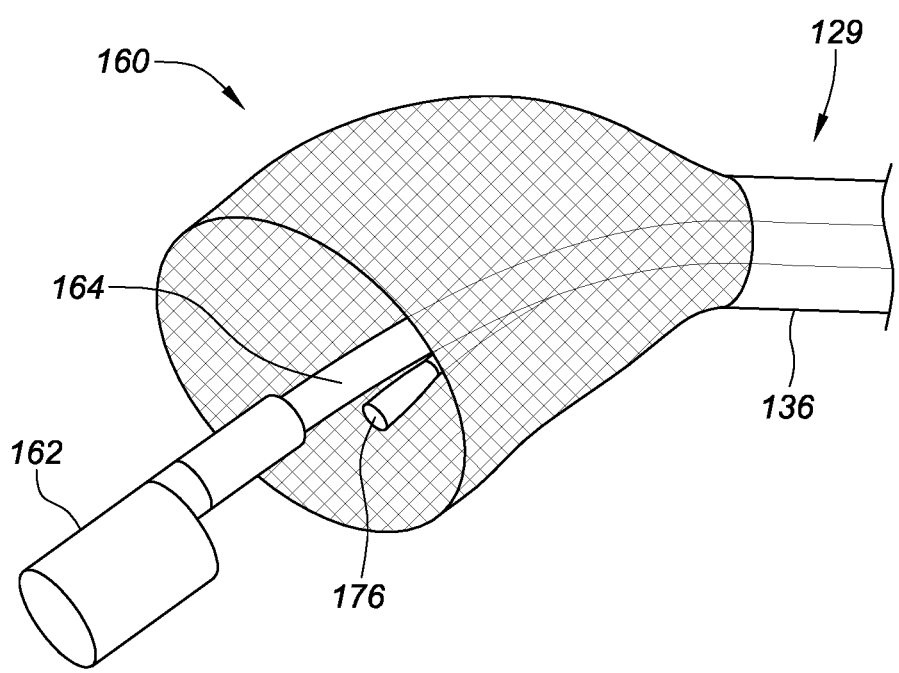
FIG. 3 depicts the steerable expanding shroud in a third deployed state, an ablation device, and a visualization device extending from the distal end of the expansion catheter associated with the exemplary expansion catheter system in FIG. 1, in accordance with embodiments of the present disclosure.

FIG. 3 depicts the steerable expanding shroud 160 in a third deployed state, a device 162, and an endoscope 176 extending from the distal end of the expansion catheter 129 associated with the exemplary expansion catheter system 100 in FIG. 1, in accordance with embodiments of the present disclosure. In some embodiments, an endoscope 176 can initially be placed in the expansion catheter 129 for guidance to a particular location and can then be removed, such that a different device can be deployed from the distal end of the expansion catheter 129. In an example, once the different device is inserted in the expansion catheter 129 or deployed from the distal end of the expansion catheter 129, the endoscope 176 can be reinserted.

In some embodiments, the expansion catheter 129 can be made more flexible when guiding the catheter into place by just having the endoscope 176 in place. As depicted in FIG. 3, the expanding catheter can been deflected laterally with respect to the longitudinal axis running along the expansion catheter 129. In an example, if three sutures are attached to the distal end of the steerable expanding shroud 160, a greater tension can be applied to one of the sutures resulting in a lateral deflection of the steerable expanding shroud 160 in a direction from the longitudinal axis towards that suture. In an example, the lateral deflection of the steerable expanding shroud 160 can be beneficial because the lateral deflection of the expanding shroud 160 can allow the distal circumference of the steerable expanding shroud 160 to make more complete contact with tissue. For instance, when a longitudinal axis defined by the expansion catheter 129 is not perpendicular with the myocardium, the distal circumference of the steerable expanding shroud 160 can be deflected such that minimal gaps or no gaps exist between the distal circumference of the steerable expanding shroud and the myocardium.

As seen in FIG. 3, the device 162 can be extended from the distal end of the outer sheath 136, such that it resides outside of the steerable expanding shroud 160. In some embodiments, an additional device (e.g., endoscope) can extend down the central lumen of the expansion catheter 129 and out of the distal end of the outer sheath 136. As such, a view can be provided via the endoscope 176. In some embodiments, the steerable expanding sheath 160 can be deflected to provide the device 162 with a maximum working range and the endoscope 176 a maximum field of view.

Figure 4:
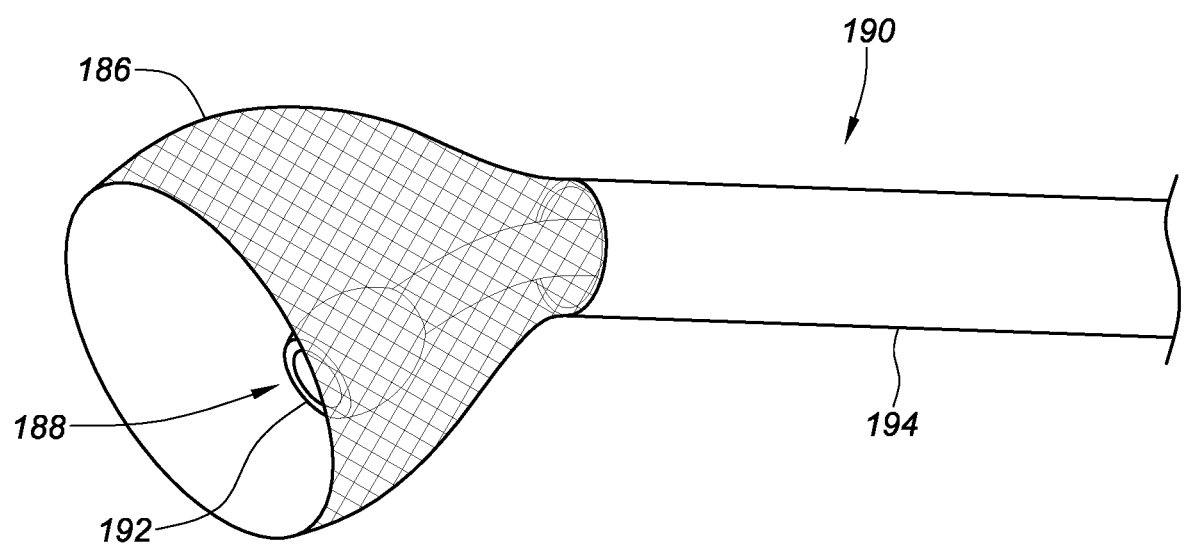
FIG. 4 depicts the steerable expanding shroud in a fourth deployed state and a visualization device extending into a volume defined within the steerable expanding shroud adjacent the distal end of the expansion catheter associated with the exemplary expansion catheter system in FIG. 1, in accordance with embodiments of the present disclosure.

FIG. 4 depicts a steerable expanding sheath 186 in a fourth deployed state and a visualization device 188 (e.g., endoscope) extending into a volume defined within the steerable expanding shroud adjacent the distal end of an expansion catheter 190 associated with the exemplary expansion catheter system 100 in FIG. 1, in accordance with embodiments of the present disclosure. As previously discussed, via selective tensioning of the sutures attached to the distal circumference of the steerable expanding shroud the steerable expanding shroud can be retracted, protracted and/or expanded by different amounts and/or laterally deflected by different amounts and/in different directions.

Some embodiments of the present disclosure include an endoscope that includes an inflatable bladder 192 at the distal tip. The inflatable bladder 192 is shown as inflated and/or partially inflated in FIG. 4. In an example, the inflatable bladder 194 can include an inner wall that is coaxial with an outer surface of the endoscope 188 and an outer wall that is coaxial with the inner wall of the inflatable bladder 194. The proximal end and the distal end of the inner and outer walls of the inflatable bladder 194 can be connected to one another, such that a seal is formed. An inflation port can exist in the inner wall, outer wall, and/or at the proximal connection point between the inner wall and the outer wall of the inflatable bladder 194. As such, air or liquid can be introduced into the inflatable bladder 194 through the inflation port via an inflation tube extending proximally down the expansion catheter. As air or liquid is pumped into the inflatable bladder 194, an annular shape and/or other shape can be formed.

In some embodiments, the inflatable bladder 194 can extend just distally of the endoscope 188, such that any abrupt edges associated with the endoscope 188 can be covered by the inflatable bladder 192, thus preventing tissue injury from occurring due to accidental and/or intentional contact between the endoscope 188 and the tissue of the patient. In some embodiments, an edge of the steerable expanding shroud 186, inner sheath, or outer sheath 194 can be covered or tangentially shielded by an inflatable bladder. For example, an inflatable bladder can be positioned around a distal edge (e.g., distal outer circumference) of the steerable expanding shroud 186; around a distal exterior circumference of the outer sheath 194; and/or around a distal exterior circumference of the inner sheath to prevent tissue injury from occurring due to accidental and/or intentional contact between the steerable expanding shroud 186; distal exterior circumference of the outer sheath 194; and/or distal exterior circumference of the inner sheath and the tissue of the patient.

In some embodiments, the inflatable bladder 192 may be used to assist in positioning the scope within the shroud 186. Deflection of the distal tip of the scope can swing the camera view along the arc of radius of the deflection. The bladder 192 may stabilize the scope tip with regard to the shroud 186, keeping the deflection sweep of the camera tip minimized but yet allowing its angle to change for desired view angle.

In some embodiments, the inflatable bladder 192 can be a single layer of a flexible and/or elastic material. For example, the inflatable bladder 192 can be a hollow cylinder formed of a flexible and/or elastic material that is connected to the outer wall of the endoscope at a distal end and proximal end of the hollow cylinder. The connection between the distal end and the proximal end of the inflatable bladder 192 and the outer wall of the endoscope 188 can be fluid tight, such that the space existing between an inner wall of the inflatable bladder 192 and the outer wall of the endoscope 188 can be inflated.

FIG. 5A depicts an embodiment of an expansion catheter system 200 that includes a steerable expanding shroud 202, an occlusion device 204 in a first deployed state, and a visualization device 206 extending from a distal end of the outer sheath 208 comprising part of the expansion catheter 210, in accordance with embodiments of the present disclosure. As discussed herein, the expansion catheter 210 can include the outer sheath 208 and the steerable expanding shroud 202 that is deployed from the distal end of the outer sheath 208.

In some embodiments, the steerable expanding shroud 202 can be deployed in an opening in the pericardium, such that an outer circumference of the steerable expanding shroud 202 'grabs' the pericardium, thus stabilizing the expansion catheter 210 and preventing movement of the expansion catheter 210 with respect to the pericardium. In some examples, the expansion catheter 210 may be able to lift the pericardium from the heart to create an enlarged interstitial space between the pericardium and the heart. This can allow for increased room for deployment of devices from the expansion catheter 210 in the interstitial space between the pericardium and the heart. As such, devices may be deployed wholly within the steerable expanding shroud 202 (e.g., within a lumen formed by the steerable expanding shroud 202), partially within the steerable expanding shroud 202, and/or outside of the steerable expanding shroud 202.

In some embodiments, an occlusion device 204 can be deployed from the distal end of the outer sheath 208, as discussed herein. In some embodiments, the occlusion device 204 can be used for occlusion of the left atrial appendage. In some embodiments, the occlusion device 204 can include a guide lumen through which a first guide wire passes (e.g., top guide wire 228 or bottom guide wire 230). The occlusion device 204 can include a bottom occlusion clip 212 and a top occlusion clip 214. The bottom occlusion clip 214 and the top occlusion clip 214 can be connected to a bottom support jaw 216 and a top support jaw 218, respectively, which can be configured to be closed upon one another. In an example, electrodes can be disposed along a top occlusion surface 220 of the top occlusion clip 214 and a bottom occlusion surface 222 of the bottom occlusion clip 212. In some embodiments, the top occlusion surface 220 and the bottom occlusion surface 222 can face one another. The electrodes can be disposed along the entire top and bottom occlusion surfaces 220, 222 and/or along a partial length of the top and bottom occlusion surfaces 220, 222. However, in some embodiments, the top occlusion clip 214 and the bottom occlusion clip 212 may contain ablation electrodes.

In some embodiments, the occlusion device can be connected to a distal end of a clip catheter (e.g., elongate flexible shaft 224) via a clip mount. The elongate flexible shaft 224 can extend from the proximal sheath portion through the central lumen of the outer sheath and/or In some embodiments, the bottom support jaw and the top support jaw can be connected at a clip hinge 226 (e.g., pivot point) that is connected to the clip mount. In an example, the clip hinge 226 can allow the top support jaw 218 to move respective to the bottom support jaw 216, or vice versa. Alternatively, the clip hinge 226 can allow both the bottom support jaw 216 and the top support jaw 218 to move respective to one another.

In some embodiments, the top support jaw 218 and the bottom support jaw 216 can be configured to pivot about the clip hinge 226, further depicted and discussed in relation to FIG. 5C, such that the top support jaw 218 and the bottom support jaw 216 can be opened or closed. In some embodiments, the top support jaw 218 and the bottom support jaw 216 can be closed such that the bottom occlusion clip 212 contacts the top occlusion clip 214 and/or comes within a close proximity of the top occlusion clip 214. In some embodiments, the bottom occlusion clip 212 and the top occlusion clip 214 can be closed such that when the atrial appendage is positioned between the bottom and top occlusion clips 212, 214, the atrial appendage can be occluded when the bottom and top occlusion clips 212, 214 are closed (e.g., are configured to occlude the atrial appendage).

The clip catheter (e.g., flexible shaft 224) can pass through a central lumen of the expansion catheter 210 from the occlusion device 204 to a control handle, in an example. In an undeployed state, the occlusion device 204 and the steerable expanding shroud 202 can be stored within the distal end of the outer sheath 208.

In some embodiments, as discussed in relation to FIG. 2A, the expansion catheter system can include guidewires (e.g., top guidewire 228, bottom guidewire 230) to aid in deployment of the occlusion device 204. For example, one or more guidewires can pass from a proximal end of the outer sheath 208 and can be looped in the distal end of the outer sheath 208 and can pass back to the proximal end of the outer sheath 208. In some embodiments, a distal end of the guidewires can be connected near the distal end of the outer sheath 208. For example, the guidewires can be connected to an inner wall of the distal end of the outer sheath 208. In an example, a top guide lumen 232 can be connected to the top support jaw 218 and in some embodiments can be 90 degrees opposed to the top occlusion surface 220 of the top support jaw 218 or top occlusion clip 214. For example, the top guide lumen 232 can be disposed along a side of the top support jaw 218, such that a longitudinal axis formed by the top guide lumen 232 is parallel with a longitudinal axis formed by the top support jaw 218 and/or top occlusion clip 214. In addition, a bottom guide lumen 234 can be connected to the bottom support jaw 216 and in some embodiments can be 90 degrees opposed to the bottom occlusion surface 222 of the bottom support jaw 216 or bottom occlusion clip 212. For example, the bottom guide lumen 234 can be disposed along a side of the bottom support jaw 216, such that a longitudinal axis formed by the bottom guide lumen 234 is parallel with a longitudinal axis formed by the bottom support jaw 216 and/or bottom occlusion clip 212. In an example, the guide lumens 232, 234 can be tubes, which can be hollow cylinders that are axially aligned with a longitudinal axis of each respective occlusion clip 212, 214 and/or support jaw 216, 218, as discussed herein.

In an example, a proximal end of each guidewire 228, 230 can be pushed distally such that a distal end of each guidewire 228, 230 is pushed distally with respect to the distal end of the outer sheath 208 such that a distal looped portion 236, 238 is disposed distally with respect to the distal sheath portion. In some embodiments, as depicted, a distal loop can be formed in each guidewires 228, 230, located distally with respect to the distal end of the outer sheath 208. In an example, the guidewires 228, 230 can be formed from a flexible material and/or shape memory material (e.g., nitinol), which can be naturally biased, such that loops formed by each of the guidewires 228, 230 expand when the guidewires 228, 230 are pushed out of the distal end of the outer sheath 208. For example, the guidewires 228, 230 can form loops that expand outwardly from a longitudinal axis formed by the expansion catheter 210, thus providing guides for the top guide lumen 232 and the bottom guide lumen 234 to ride along.

In some embodiments, the clip catheter can be a flexible shaft 224, which can be constructed so the shaft has an internal tension and an outer compression. Upon deployment of the guidewires 228, 230, the occlusion device 204 can be deployed from the distal end of the outer sheath 208 via the flexible shaft 224 (e.g., by pushing the flexible shaft 224 distally with respect to the outer shaft 208 and can be guided along the guidewires 228, 230. In an example, the occlusion device 204 can be turned as it follows the guidewires 228, 230 (e.g., is moved along the guidewires) toward the distal loops of the guidewires 228, 230, as depicted in FIG. 5B. For example, the occlusion device 204 can be turned from a straight orientation, the straight orientation being aligned with the sheath longitudinal axis, as the occlusion device is moved distally along the first guidewire and about the distal looped portion (e.g., distal looped portion 236). In some embodiments, the distal looped portion and the occlusion device can be stored within the central lumen in an undeployed state and can be located distally with respect to the distal sheath portion in a deployed state.

In some embodiments, a first guidewire (e.g., top guidewire 228) can comprise a first guidewire end and a second guidewire end and a second guidewire (e.g., bottom guidewire 230) can comprise a third guidewire end and a fourth guidewire end. The first and second guidewires can extend from their respective guidewire ends through the central lumen and can form a first guidewire distal looped portion 236 and a second guidewire distal looped portion 238, respectively, as depicted. In some embodiments, the first and second guidewire distal looped portions 236, 238 are stored within the central lumen in an undeployed state and the first and second guidewire distal looped portions 236, 238 are configured to expand outwardly (e.g., laterally) with respect to a longitudinal axis of the outer sheath 208 upon deployment from the distal sheath portion.

In some embodiments, the guide lumens 232, 234 can each be aligned with a longitudinal axis of a respective one of the support jaws 216, 218. In some embodiments, the first support jaw 216 can be configured to be moved distally along the first guidewire and about the first guidewire distal looped portion 236 and the second support jaw can be configured to be moved distally along the second guidewire and about the second distal looped portion 238 in unison with the first support jaw. In some embodiments, the first support jaw 216 and the second support jaw 218 can be turned from a straight orientation, the straight orientation being aligned with the sheath longitudinal axis, as the first support jaw 216 and the second support jaw are moved distally along the first and second guidewire and about the first and second distal looped portions 236, 238.

In some embodiments, the bladder 192 can help stabilize and hold guidewires 228 and 230 in place against inside of shroud 186, if sufficiently inflatable to fill the shroud after the clip 212 and 214 is advanced outside the shroud. In some embodiments, this can help maintain an advantageous guidewire position.

FIG. 5B depicts the steerable expanding sheath 202, the occlusion device 204 in a second deployed state, and the visualization device 206 extending from the distal end of the outer sheath 208 comprising part of the expansion catheter 210, in accordance with embodiments of the present disclosure. In some embodiments, the endoscope can extend through the central lumen (e.g., of the outer sheath 208 and/or inner sheath) from the proximal sheath portion to the distal sheath portion. As depicted in FIG. 5B, the endoscope 206 can also be moved distally with respect to the expansion catheter 210 to enable a better view of the occlusion device 204 and/or surrounding tissue structures within the body of the patient. As depicted, the occlusion device 204 can follow the guidewires 228, 230 as it is pushed distally with respect to the distal end of the outer sheath 208. In some embodiments, the flexible shaft 224 can bend to allow the occlusion device 204 to turn along the path formed by the guidewires 228, 230. In some embodiments, the guidewires 228, 230 can have a rigidity, individually or in combination with one another, that is greater than a rigidity of the flexible shaft 224, allowing for the flexible shaft 224 to bend instead of the guidewires 228, 230 as the occlusion device 204 is protracted and/or allowing for the flexible shaft 224 to bend more than the guidewires 228, 230 as the occlusion device 204 is protracted.

FIG. 5C depicts a view from the visualization device 206 in FIG. 5B, in accordance with embodiments of the present disclosure. As depicted, the view from the visualization device 206 (e.g., endoscope) shows the occlusion device 204, the guide lumens 232, 234, the guidewires 228, 230, the steerable expanding shroud 202, as well as the flexible shaft 224, which has been moved distally to deploy the occlusion device 204. A view of the clip hinge 226, as well as a clip hinge pin 250 is depicted. The top support jaw 218 can be configured to rotate about the hinge pin 250 and/or the bottom support jaw 216 can be configured to rotate about the hinge pin 250 to enable closing of the occlusion device 204. In some embodiments, the clip advancing and opening controls 146, depicted in FIG. 2A, can be used to open and/or close the occlusion device 204. In an example, the cable housing 150 and the cable 148 can extend through the flexible shaft 224. In some embodiments, a distal end of the cable 148 can be attached to the bottom support jaw 216 and upon pulling the pull knob 149 proximally, the bottom support jaw 216 can be closed and/or moved closer in relation to the top support jaw 218 (e.g., the bottom occlusion clip 212 can be moved closer to the top occlusion clip 214). In some embodiments, the guidewires 228, 230 can be biased in order to open the occlusion device 204. Thus, the occlusion device 204 can naturally remain in an open state unless a tension is applied to the cable 148 (e.g., via the pull knob).

Figure 6A:
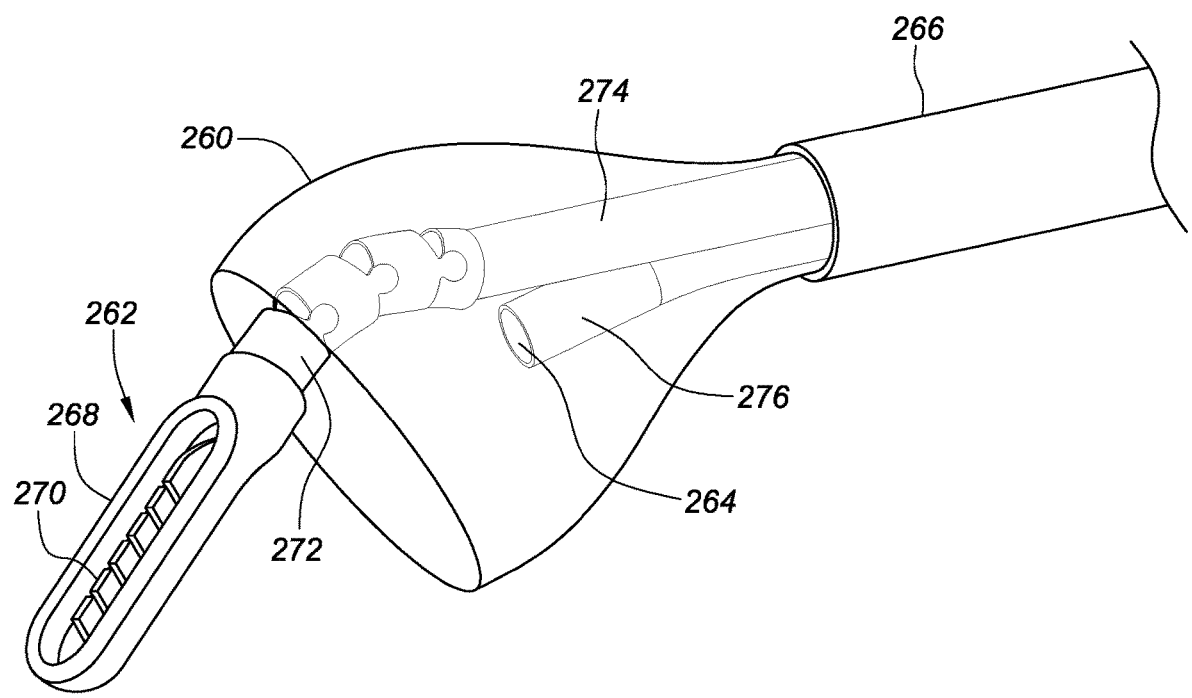
FIG. 6A depicts the steerable expanding shroud, an ablation device, and a visualization device extending from a distal end of the steerable expanding shroud associated with the exemplary expansion catheter system in FIG. 1, in accordance with embodiments of the present disclosure.

FIG. 6A depicts the steerable expanding shroud 260, an ablation device 262, and a visualization device 264 (e.g., endoscope) extending from a distal end of the expansion catheter 266 associated with the exemplary expansion catheter system in FIG. 1, in accordance with embodiments of the present disclosure. In some embodiments, an elongated suction ablation device 262, such as the COBRA Fusion® device can be deployed from the distal end of the expansion catheter 266. The elongated suction ablation device 262 can operate by creating a vacuum in a trough 270 of the suction body 268 that draws tissue into the trough 270, which is lined with electrodes. Power can be applied to the electrodes and used to ablate tissue, ensuring transmurality. The suction can also be used to hold the device in a desired location. In an example, the elongated suction ablation device 262 can be attached to a shaft that extends through the expansion catheter 266 and is connected to the elongated suction ablation device 262 via a manipulatable joint 272. In some embodiments, the manipulatable joint 272 can be robotic and controlled from the catheter handle and/or via another mechanical and/or electronic device in communication with the manipulatable joint 272.

In some embodiments, the elongated suction ablation device 262 can be deployed from the expansion catheter 266 by moving the shaft 274 associated with the device 262 distally along the expansion catheter. In addition, an endoscope can be deployed from the expansion catheter. In an example, the endoscope can include an inflatable bladder 276, as discussed in relation to FIG. 4. As depicted in FIG. 6A, the inflatable bladder 276 is in a deflated state. In an example, when the endoscope 264 is stored in the expansion catheter 266, the inflatable bladder 276 can be deflated.

Figure 6B:
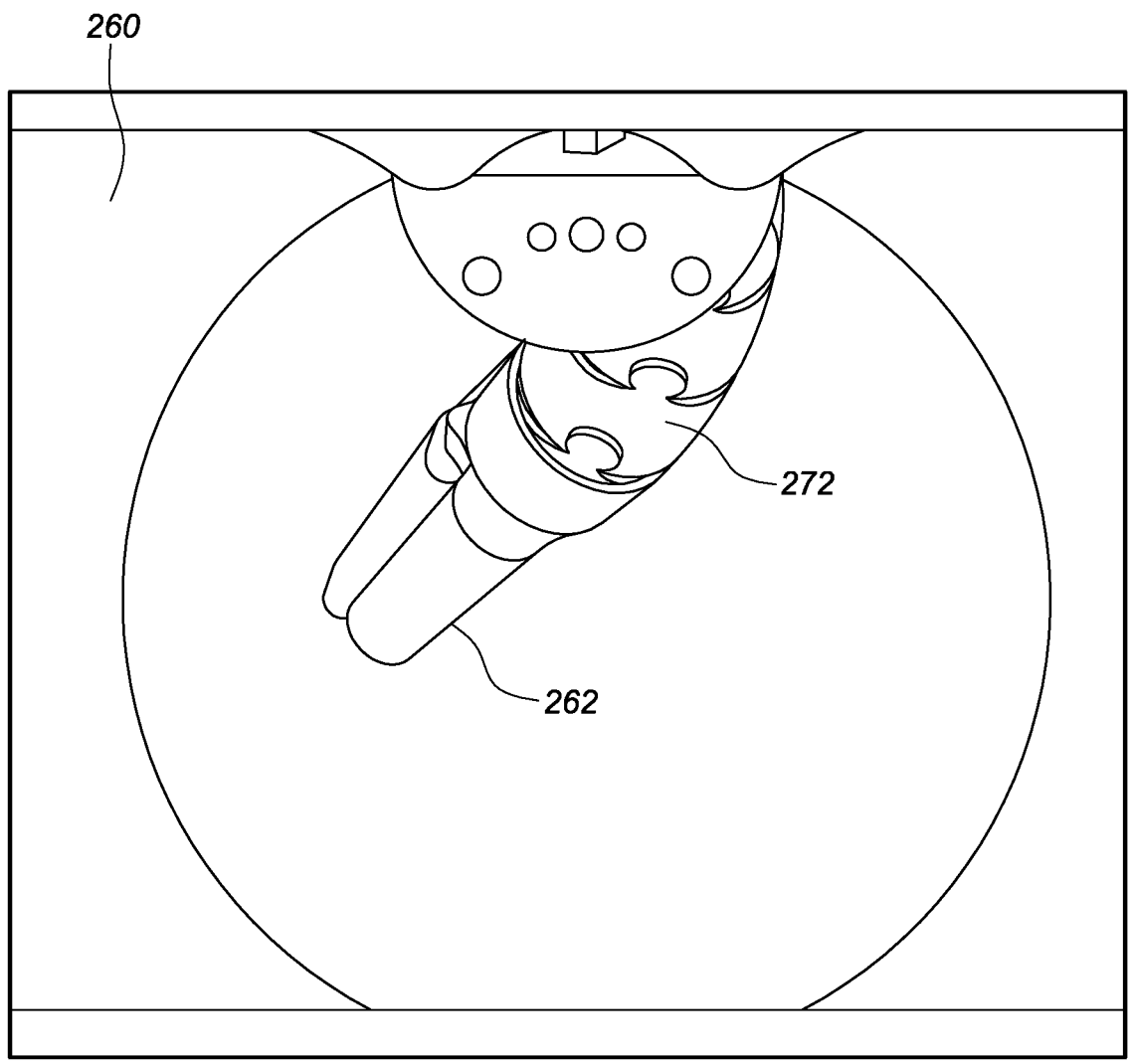
FIG. 6B is a view from the visualization device in FIG. 6A, in accordance with embodiments of the present disclosure.

FIG. 6B depicts a view from the visualization device 264 in FIG. 6A, in accordance with embodiments of the present disclosure. As depicted, a view from the visualization device 264 shows the elongated suction ablation device 262, the manipulatable joint 272, as well as the steerable expanding shroud 260. In some embodiments, the manipulatable joint 272 can be rotated, such that the elongated suction ablation device 262 can be rotated about a longitudinal axis formed by the shaft 274. In some embodiments, the manipulatable joint 272 can be a universal joint, allowing for deflection and/or torque transmission (e.g., roll) of the elongated suction ablation device 262 with respect to the shaft 274.

Figure 6C:
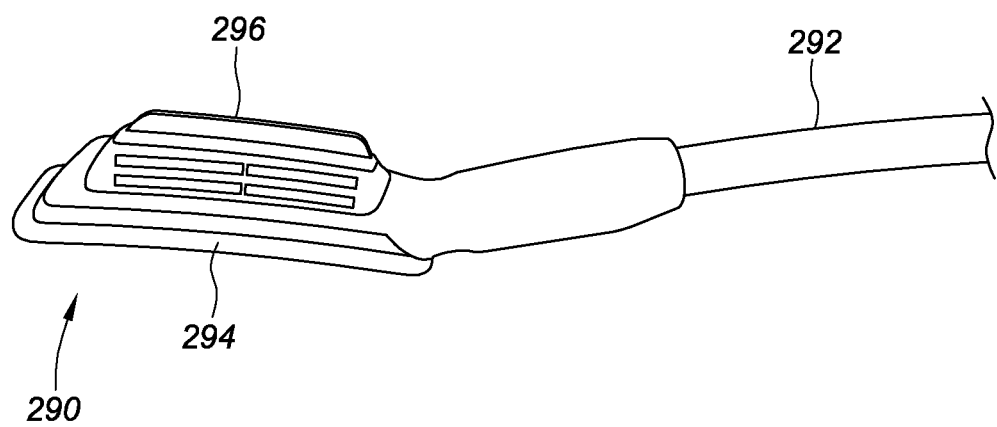
FIG. 6C depicts an elongated suction ablation device, in accordance with embodiments of the present disclosure.

FIG. 6C depicts an elongated suction ablation device 290, in accordance with embodiments of the present disclosure. In some embodiments, the elongated suction ablation device 290 can include a shaft 292, which can be flexible, semi-rigid, and/or steerable. The suction body 294 can be similar to the one depicted in FIG. 6A. The shaft 292 can be connected to an elongated suction body 294, which can be similar to the COBRA Fusion® device, without a magnet and/or tether located at a distal end of the suction body 294. Alternatively, in some embodiments, the distal end of the suction body 294 can include a magnet and/or tether. In some embodiments, an axial length of the suction body 294 can be approximately 25 millimeters, although dimensions are not so limited and the axial length of the suction body can be larger or smaller.

In some embodiments, a dorsal guidewire lumen 296 can extend dorsally along the suction body 294. In some embodiments, one or more lateral guidewire lumens can be disposed alongside the suction body. For example, a pair of lateral guidewire lumens can be disposed alongside the suction body and can be diametrically opposed to one another. The guidewire lumen 294 can be a tube through which a guidewire can pass in a manner similar to that discussed and depicted in relation to guide lumens 232, 234 in FIGS. 5A-5D. For example, the suction body 294 can be pushed from the distal end of the expansion catheter into a space created by the steerable expansion sheath and can be guided in place along the guidewire passing through the guide lumen.

Figure 6D:
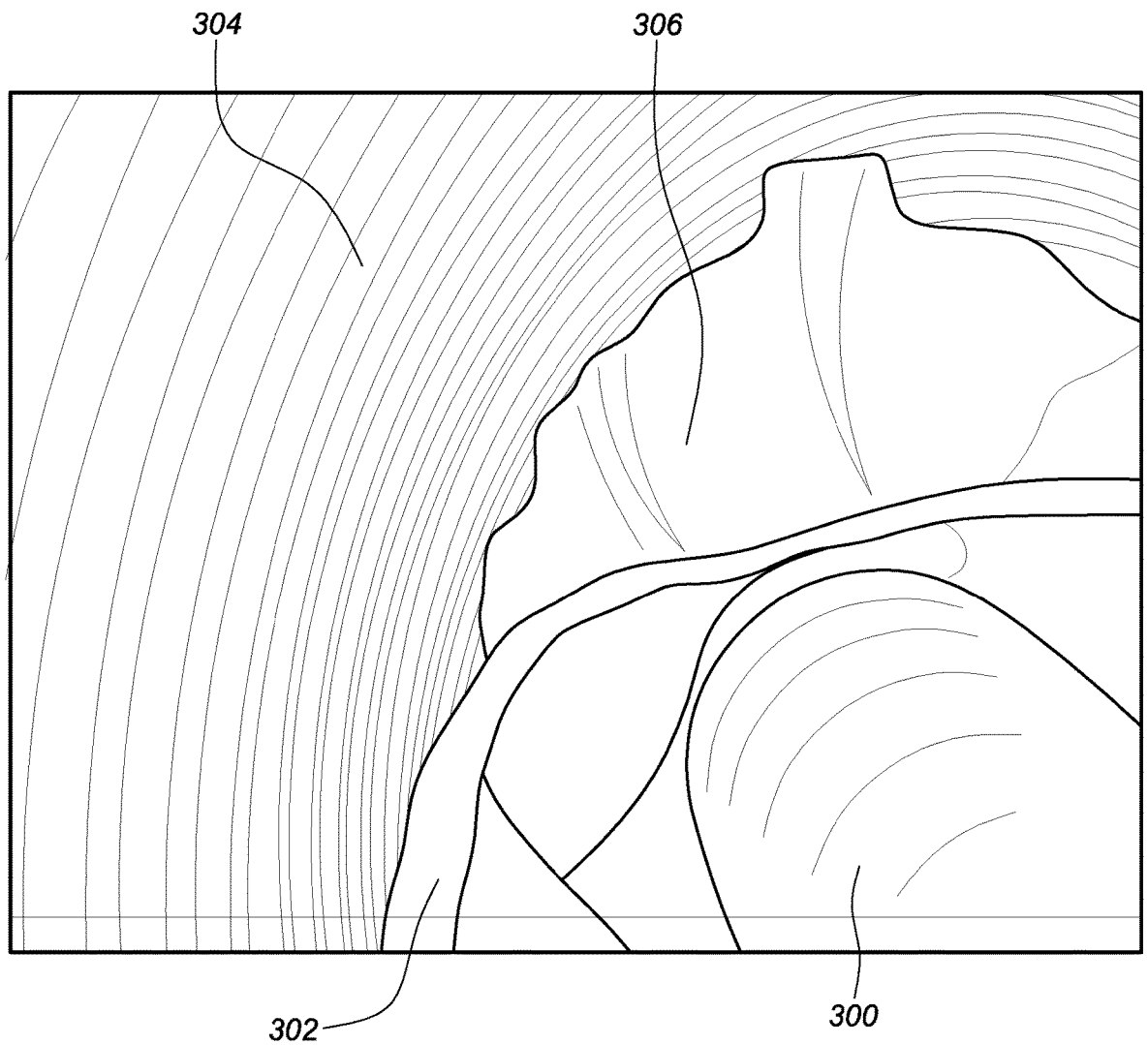
FIG. 6D is a stylized representation of a view from the visualization device in FIG. 6A, in accordance with embodiments of the present disclosure.

FIG. 6D represents a stylized representation of a view from a visualization device showing an elongated suction ablation device, similar to the one shown in FIG. 6C, being guided along a guidewire 302 inside of a lumen 304, in accordance with embodiments of the present disclosure. In an example, the suction body 300 of the elongated suction device is shown contacting or about to contact tissue 306 to perform an ablation. The suction body 300 can include the guide lumen (not shown) mounted dorsally along the suction body, as depicted in FIG. 6C. The guidewire 302 can extend through the guide lumen and can form a distal loop, as discussed herein. As the suction body 300 is advanced by a combination of pushing and/or pulling on the guidewire 302 and/or pushing and/or pulling on the shaft connected to the suction body 300, the dorsal guide lumen can move along the guidewire 302 causing the suction body 300 to be positioned in a particular manner, as discussed and depicted in relation to FIGS. 5A-5D.

Figure 7:
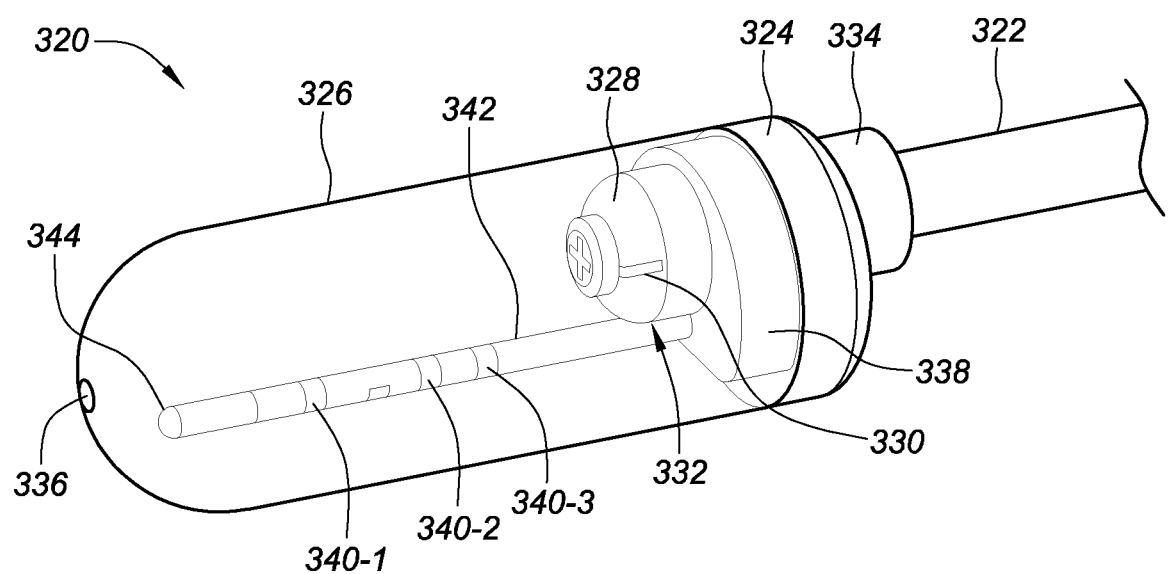
FIG. 7 is an isometric side and front view of a visualization, pacing, sensing, and/or ablation device, in accordance with embodiments of the present disclosure.

FIG. 7 depicts an isometric side and front view of a visualization, pacing, sensing, and/or ablation device (hereinafter device 320), in accordance with embodiments of the present disclosure. In some embodiments, the device 320 can include a sheath and a mount 324, to which a sealed cap 326 can be attached. In some embodiments, the sealed cap 326 can be attached to a recessed cap mounting lip 338 circumferentially extending around an exterior of the mount 324. In an example, the sheath 322 can be connected to the mount 324. In some embodiments, an endoscope 328 can be inserted into and extend through a lumen defined by the sheath 322. The endoscope 328 can be steerable, in some embodiments. In an example, the endoscope 328 can be slid distally from the position it is shown in FIG. 7, such that the endoscope 328 is placed within the sealed cap 326 and can be steered within the sealed cap 326 to view different area.

In some embodiments, the sealed cap 326 can create a space between the endoscope 328 and the tissue to improve visualization. In some embodiments, the sealed cap 326 can protect the endoscope 328 from fluids to enable a clear view from the endoscope 328. The sealed cap 326 can make ablation more effective and enhance the view with further separation from target tissue while still minimizing a profile of the device 320.

In some embodiments, the mount 324 can include a port 332 for the endoscope 328 to pass through. In an example, a distal end of the port 332 can include one or more axial relief cuts 330 made around a circumference of the port 332, which can extend parallel with a longitudinal axis extending through the port 332. The one or more relief cuts 330 can allow a distal rim of the port 332 to flex when the endoscope 328 is placed in the port 332. Flexing of a distal rim of the port 332 via the relief cuts when the endoscope 328 is placed through the port 338 can create a frictional force between the endoscope 328 and the distal rim of the port 332, thus keeping the endoscope 328 in place, within the port 332, and preventing the endoscope 328 from being accidentally shifted.

In some embodiments, the mount 324 can include a proximal outer lip, to which a flexible torqueable sheath can be connected (e.g., slid over). The flexible torqueable sheath can be passively flexible, such that it can deflect when the endoscope 328 is deflected, as further discussed herein. For example, the sealed cap 326 can be provided with four-way steerability.

In some embodiments, an irrigation lumen can be in fluid communication with the sealed cap, such that the sealed cap 326 can be filled with a fluid (e.g., liquid, gas). In an example, liquid can be introduced into the sealed cap 326 and can fill the sealed cap 326 to reduce a glare produced on an inner surface of the sealed cap 326. The fluid can be expelled from a distal tip hole 336 and/or other holes formed in the sealed cap 326 to provide irrigation.

In some embodiments, electrodes 340-1, 340-2, 340-3 can be disposed on an outside of the sealed cap 326. In an example, an electrode shaft 342 can include ring electrodes 340-1, 340-2, 340-3 spaced apart between a distal tip of the electrode shaft 342 and a proximal end of the electrode shaft 342. In some embodiments, as depicted, the electrode shaft 342 can extend parallel, but off-axis with respect to a longitudinal axis extending through the sealed cap 326. The ring electrodes 340-1, 340-2, 340-3 can be separated from one another via an insulating material and can be used for ablation, sensing, and/or pacing. The distal end of the electrode shaft 342 can include a tip electrode 344 in some embodiments, which can be used for ablation, sensing, and/or pacing.

In some embodiments, the device 320 and/or the sealed cap 326 can be made from a rigid, semi-rigid, flexible, and/or elastic material that is translucent and/or semi-translucent, such that the endoscope 328 can look through the sealed cap. In some embodiments, an axial groove can be disposed in an outer surface of the sealed cap 326 that extends parallel, but off axis with respect to a longitudinal axis extending through the sealed cap 326. In an example, the electrode shaft 342 can be placed within the axial groove, as discussed herein.

In some embodiments, the sealed cap 326 can be inflated and/or deflated through introduction of a fluid into the sealed cap 326. Inflation or deflation of the sealed cap 326 can allow for the sealed cap 326 to more easily fit into a distal end of an expansion catheter and/or be more easily introduced into various cavities of the body. Upon deployment of the sealed cap 326 from the expanded catheter, for example, the sealed cap 326 can be inflated from a deflated and/or partially deflated state.

Figure 8A:
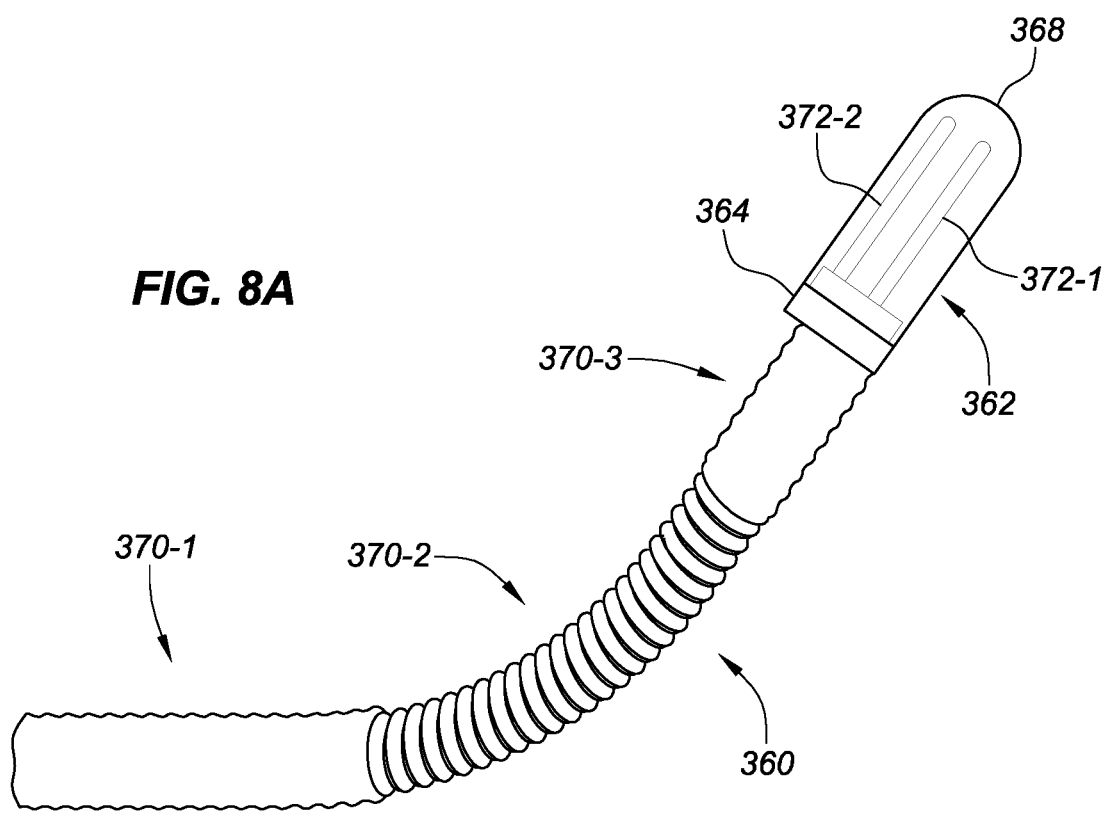
FIG. 8A is a side view of the visualization, pacing, sensing, and/or ablation device similar to that depicted in FIG. 7 attached to a distal end of a catheter, in accordance with embodiments of the present disclosure.

FIG. 8A depicts a side view of the visualization, pacing, sensing, and/or ablation device 362 similar to that depicted in FIG. 7 attached to a distal end of a catheter 360, in accordance with embodiments of the present disclosure. The device 362 can include a mount 364, endoscope (not depicted), and/or sealed cap 368, as discussed in relation to the device in FIG. 7. The device 362 can be attached to a distal end of a catheter 360, as shown in FIG. 8. In some embodiments, the catheter 360 can include different materials such that different portions of the catheter 360 can have a different flexibility. For example, distal and proximal portions of the catheter 370-1, 370-3 can be less flexible than an intermediate portion 370-2 of the catheter 360. In some embodiments, the distal and proximal portions of the catheter 370-1, 370-3 can be a shrink wrap that is applied to an outer surface of the catheter. This can allow the intermediate portion of the catheter 370-2 to be more flexible, thereby allowing for an increased flexibility associated with that portion of the catheter.

In some embodiments, the device 362 can include a first electrode shaft 372-1 and a second electrode shaft 372-2 that contain one or more ablation, sensing, and/or pacing electrodes. As discussed in relation to FIGS. 7, 10A, and 10B, the sealed cap 368 can include an axial groove disposed along the outside of the sealed cap 368 for the first electrode shaft 372-1 and the second electrode shaft 372-2. The first and second electrode shafts 372-1, 372-2 can be placed in each respective axial groove.

Figure 8B:
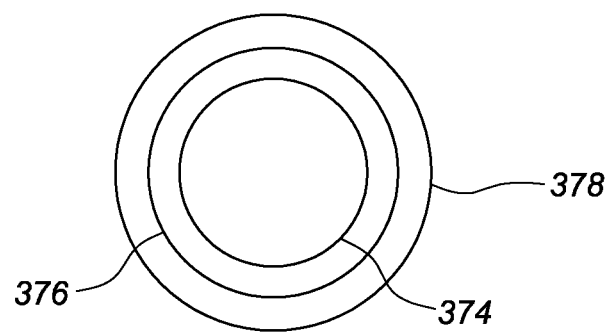
FIG. 8B depicts a cross section of the catheter shown in FIG. 8A, in accordance with embodiments of the present disclosure.

FIG. 8B depicts a cross section of the catheter shown in FIG. 8A, in accordance with embodiments of the present disclosure. In some embodiments, an endoscope cable 374 can pass through a central lumen of a sheath 376, which is depicted in FIG. 7. The endoscope cable 374 can be passively flexible, in some embodiments, and the sheath 376 can include pull wires, which can be selectively tensioned to deflect the sheath 376. Alternatively, the endoscope cable 374 can be deflectable and the sheath 376 can be passively flexible. In some embodiments, the sheath 376 can be inserted into a lumen defined by the proximal lip 334, but not connected to the mount, shown in FIG. 7. In some embodiments, a flexible torqueable sheath 378 can be coaxial with the sheath 376, such that the sheath 376 passes through a center of the flexible torqueable sheath 378. In an example, the flexible torqueable sheath 378 can be connected to an outer face of the proximal lip 334 and can be rotatable with respect to the sheath 376 and the endoscope. As such, the flexible torqueable sheath 378 can be rotated, thus rotating the mount 364 and the sealed cap 368 with respect to the endoscope, and the sheath 376. Thus, the electrode shafts 372-1, 372-2 disposed on the outside of the sealed cap 368 can be rotated to a particular position. In some embodiments, the endoscope can also be rotated to orient the endoscope in such a way that a display generated by the endoscope appears in a proper orientation (e.g., right side up).

Figure 9:
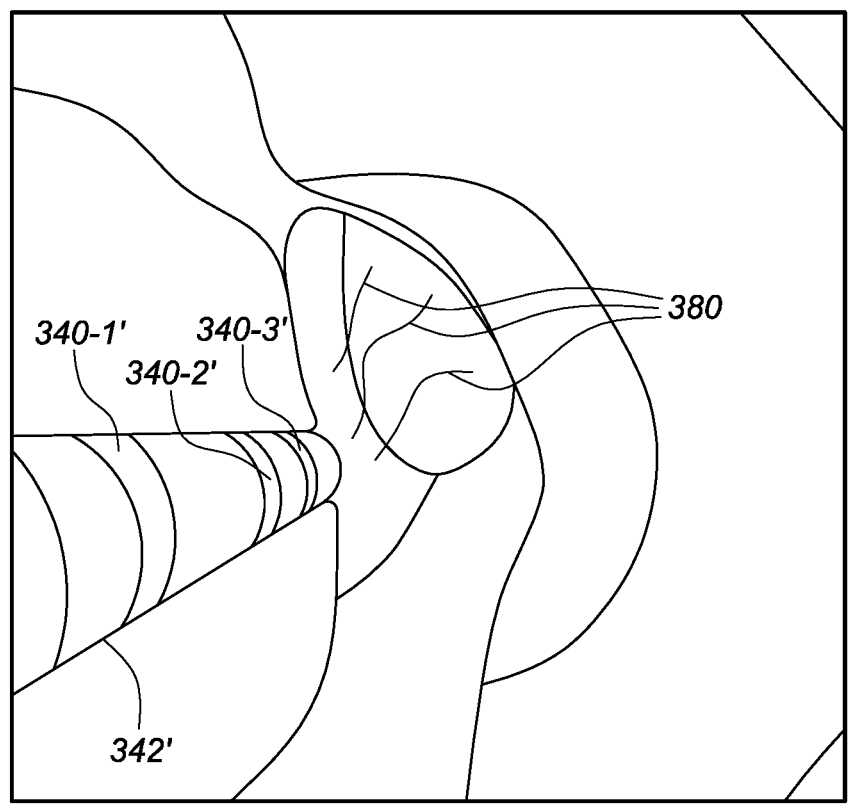
FIG. 9 depicts a stylized representation of a view from a visualization device within the visualization, pacing, sensing, and/or ablation device in FIG. 7, in accordance with embodiments of the present disclosure.

FIG. 9 depicts a stylized representation of a view from an endoscope within the visualization, pacing, sensing, and/or ablation device in FIG. 7, in accordance with embodiments of the present disclosure. In an example, the view can be from the endoscope placed with the sealed cap 326. The view from the endoscope can overlook the electrode shaft 342' that contains electrodes 340-1', 340-2', 340-3' and also overlook the tissue that has been ablated or will be ablated. As depicted, the ablation lines have been created via a tip electrode 344 located at a distal tip of the electrode shaft 342. In some embodiments, the endoscope can be used to provide a view when navigating the device 320 into position to perform an ablation, sensing, and/or pacing procedure.

Figure 10A:
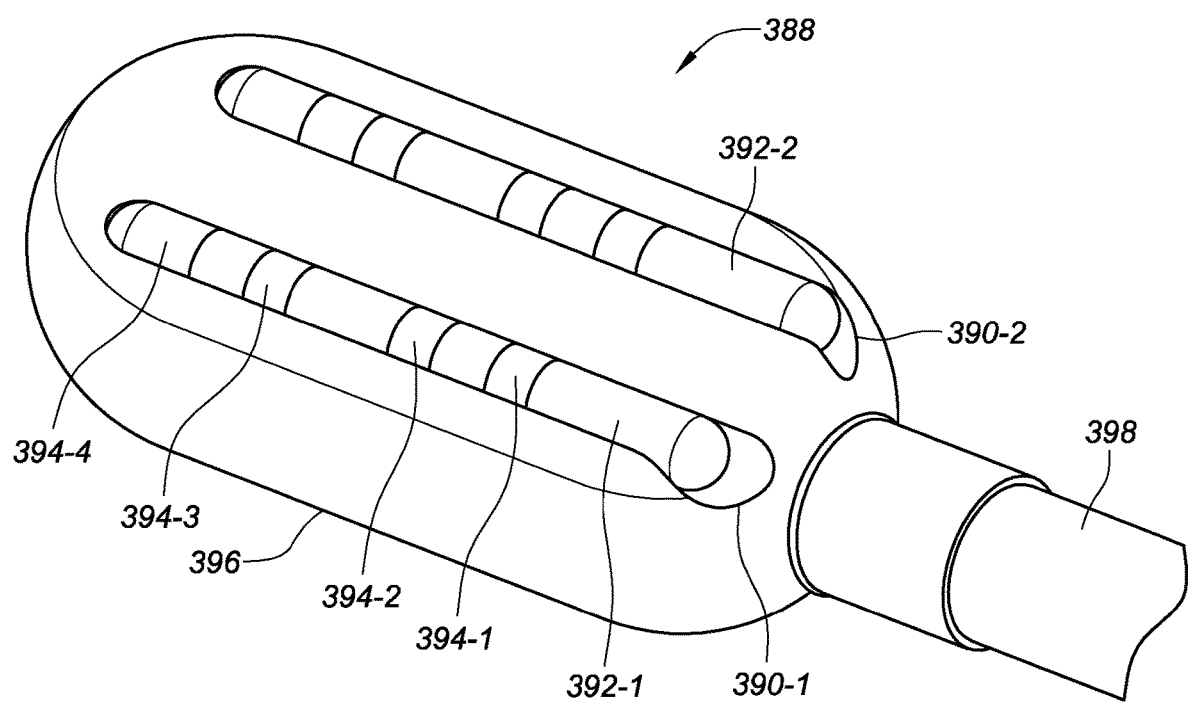
FIG. 10A is an isometric side and bottom view of a visualization, pacing, sensing, and/or ablation device, in accordance with embodiments of the present disclosure.

FIG. 10A depicts an isometric side and bottom view of a visualization, pacing, sensing, and/or ablation device 388, in accordance with embodiments of the present disclosure. In some embodiments, a proximal end of a sealed cap 396 can be connected to a distal end of a shaft 398. As depicted, the sealed cap 396, as previously discussed, can include grooves formed in a bottom of the sealed cap 396, in which electrode shafts can be placed. The electrode shafts 392-1, 392-2 can include electrodes 394-1, 394-2, 394-3, 394-4 for ablation, sensing, and/or pacing, in some embodiments. In some embodiments, the device 388 can comprise two or more electrodes, which can be used for bi-polar ablation of tissue. In some embodiments, material forming the bottom of the sealed cap 396 (e.g., portion of the sealed cap in which the grooves are formed) can be thicker than in other portions of the sealed cap to provide support for the electrode shafts 392-1, 392-2 and more easily allow the grooves to be formed, as shown in relation to FIG. 11A.

Figure 10B:
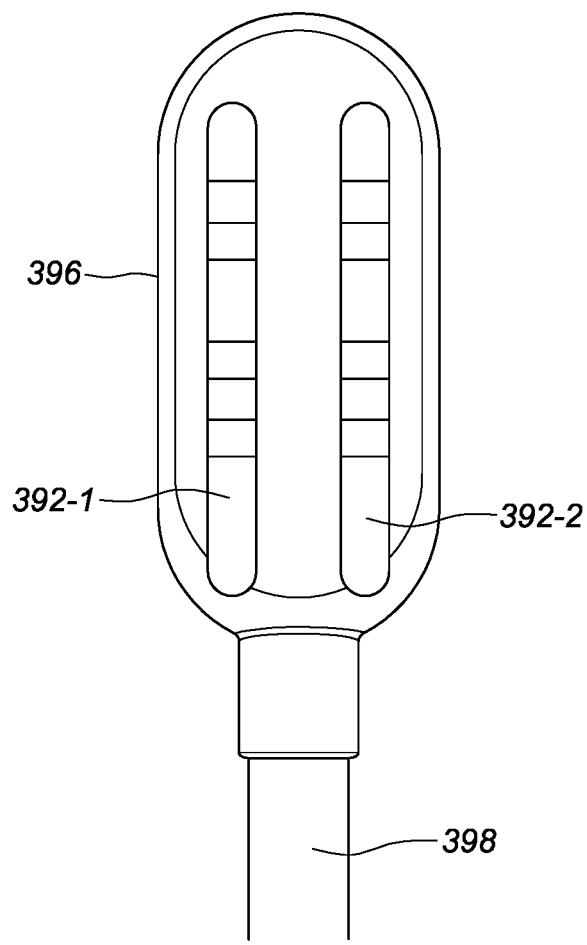
FIG. 10B is a bottom view of a visualization, pacing, sensing, and/or ablation device depicted in FIG. 10A, in accordance with embodiments of the present disclosure.

FIG. 10B depicts a bottom view of the visualization, pacing, sensing, and/or ablation device 388 depicted in FIG. 10A, in accordance with embodiments of the present disclosure. As depicted, the electrode shafts 392-1, 392-2 can extend axially along the bottom of the sealed cap 396. As discussed herein, the sealed cap 396 can be formed of a translucent and/or semi-translucent material so the endoscope can provide an image through the sealed cap 396.

Figure 11A:
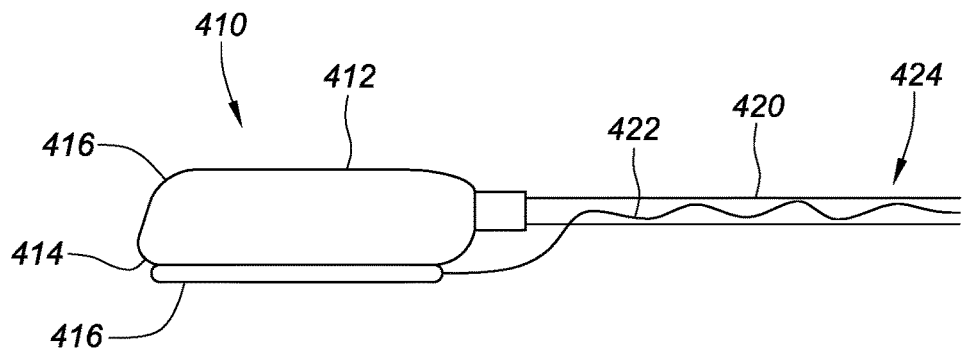
FIG. 11A is a side view of a visualization, pacing, sensing, and/or ablation device, in accordance with embodiments of the present disclosure.

FIG. 11A depicts a side view of a visualization, pacing, sensing, and/or ablation device 410, in accordance with embodiments of the present disclosure. In an example, the device 410 can include the sealed cap, as discussed herein. In some embodiments, a bottom portion 414 of the sealed cap 412 can include a thicker walled material than some other portions of the sealed cap 412. As depicted, the bottom portion 414 can be thick walled and other portions can be thin walled. In some embodiments, the electrode shafts 416 can be connected to the thick walled bottom portion 414.

In some embodiments, the bottom portion can be formed of a substrate that is different than thin walled portions 418. For example, the substrate can be a translucent material that is formed from a semi-rigid and/or rigid material, while some other portions of the sealed cap 412 (e.g., thin walled portions 418) can be formed of a flexible or elastic material. In an example, only a portion of the sealed cap 412 that houses the electrode shafts 416 with a reasonable margin is comprised of a rigid optically clear polymer. The remainder of the sealed cap 412 can be comprised of an expandable member such as a woven wire frame or optionally a balloon, bonded to the rigid element to provide an expansion means, discussed herein. If a balloon is used, the balloon can be separated from the rigid ablation element to avoid issues of heat/cold affecting the balloon's integrity. For example, a balloon can be connected to the substrate, such that the balloon can be inflated and/or deflated to reduce a size of the sealed cap 412 for introduction into the body of a patient. In an example, the device 410 can be reduced to a size that would fit into a 4/10 millimeter cannula. As further depicted, a sheath 420 can be connected to the proximal end of the sealed cap 412 and a wire can provide electricity to the electrodes on the electrode shafts 416. In some embodiments, the sheath 420 can include pull wires for steering the sheath 420. The pull wires, in some embodiments, can also provide electricity to the electrodes or other components associated with the sealed cap 412. In addition, an endoscope can be included in the sealed cap 412, as discussed herein. A view from the endoscope can be of an area where an ablation or other procedure is being performed. A cable associated with the endoscope can pass through an opening 424 in the sheath 420 to provide connectivity with the endoscope.

In some embodiments, as discussed herein, ablation elements disposed on an outside of the sealed cap 412 can be electrodes. Ablation elements can be configured as an RF-electrode, cryo-electrode, bipolar RF shaft, or a vacuum trough with opposing electrodes, such as those associated with the COBRA Fusion® device.

Figure 11B:
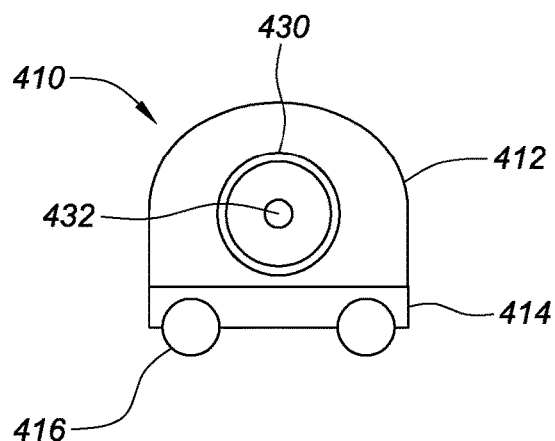
FIG. 11B is a front view of the visualization, pacing, sensing, and/or ablation device depicted in FIG. 11A, in accordance with embodiments of the present disclosure.

FIG. 11B depicts a front view of the visualization, pacing, sensing, and/or ablation device 410 depicted in FIG. 11A, in accordance with embodiments of the present disclosure. In some embodiments, a fluid lumen can pass through the shaft 420 associated with the sealed cap 412 and can be used to introduce a fluid into the sealed cap 412 to inflate the sealed cap 412 and/or reduce a glare within the sealed cap 412 and/or visual distortion that arises from the air to polymer interface of the inner surface within. In an example, the fluid can be a gas such as carbon dioxide and/or a liquid such as saline. In some embodiments, fluid entering the sealed cap from the fluid lumen 430 can pass through the distal tip hole 432 in the sealed cap such that irrigation fluid can be provided to a therapy site and/or gas can be provide to a therapy site for insufflation.

Figure 12A:
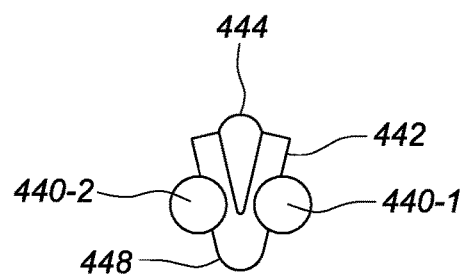
FIG. 12A is a front view of an alternate embodiment of the visualization, pacing, sensing, and/or ablation device in FIG. 11B with a hinge and in a folded state, in accordance with embodiments of the present disclosure.

FIG. 12A depicts a front view of an alternate embodiment of the visualization, pacing, sensing, and/or ablation device in FIG. 11B with a hinge 448 and in a folded state, in accordance with embodiments of the present disclosure. In some embodiments, the sealed cap can include a hinge 448 that extends axially along a bottom of the sealed cap. In an example, the hinge can extend between the two electrode shafts 440-1, 440-2 and can be connected to the substrate 442 that forms the bottom of the sealed cap. In an example, the substrate 442 can be a semi-rigid and/or rigid material and the hinge 448 can axially divide the substrate 442 in half, such that the substrate 442 can be folded in half. In an example, a flexible material 444 can be connected to a perimeter of the substrate 442 and the pieces of the substrate 442 that are divided by the hinge can be folded toward the flexible material (e.g., upward) to collapse the sealed cap and flexible material and reduce its size, as shown in FIG. 12A.

Figure 12B:
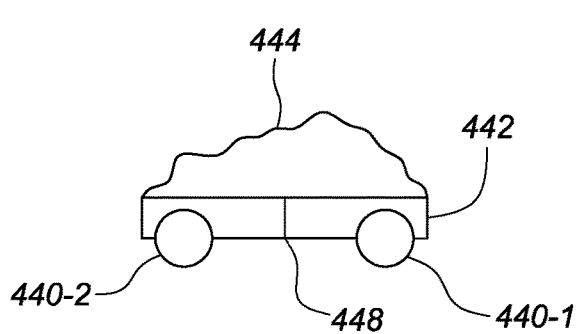
FIG. 12B is a front view of the visualization, pacing, sensing, and/or ablation device in FIG. 12A in an opened and partially expanded state, in accordance with embodiments of the present disclosure.

FIG. 12B depicts a front view of the visualization, pacing, sensing, and/or ablation device in FIG. 12A in an opened and partially expanded state, in accordance with embodiments of the present disclosure. In an example, the device in FIG. 12A can be unfolded about the hinge 448, as illustrated in FIG. 12B. As depicted, a joint can be seen running through the substrate between the electrodes in FIG. 12B at which the hinge 448 can be placed. In some embodiments, the hinge 448 can be a sealed hinge, such that fluid does not leak from an inner space of the sealed cap through the hinge 448. The flexible material 444 can be seen in a partially expanded state draped across a top of the substrate 442 and connected to the perimeter of the substrate 442.

Figure 12C:
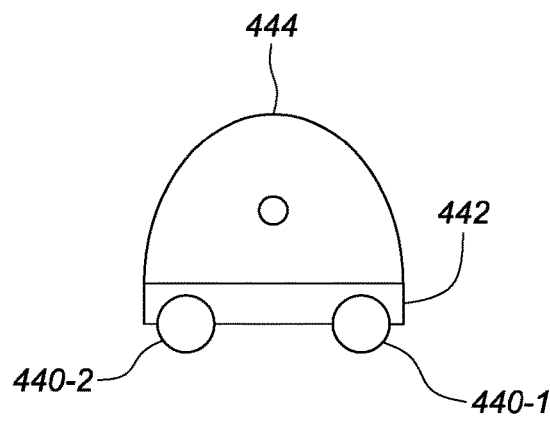
FIG. 12C is a front view of the visualization, pacing, sensing, and/or ablation device in FIG. 12A in an opened and expanded state, in accordance with embodiments of the present disclosure.

FIG. 12C depicts a front view of the visualization, pacing, sensing, and/or ablation device in FIG. 12A in an opened and expanded state, in accordance with embodiments of the present disclosure. As depicted, a fluid can be introduced into the sealed cap and the fluid can cause the flexible material 444 to be expanded and inflated to a particular size. The device can have an inflated diameter in some embodiments of 1 to 3 centimeters.

Figure 13A:
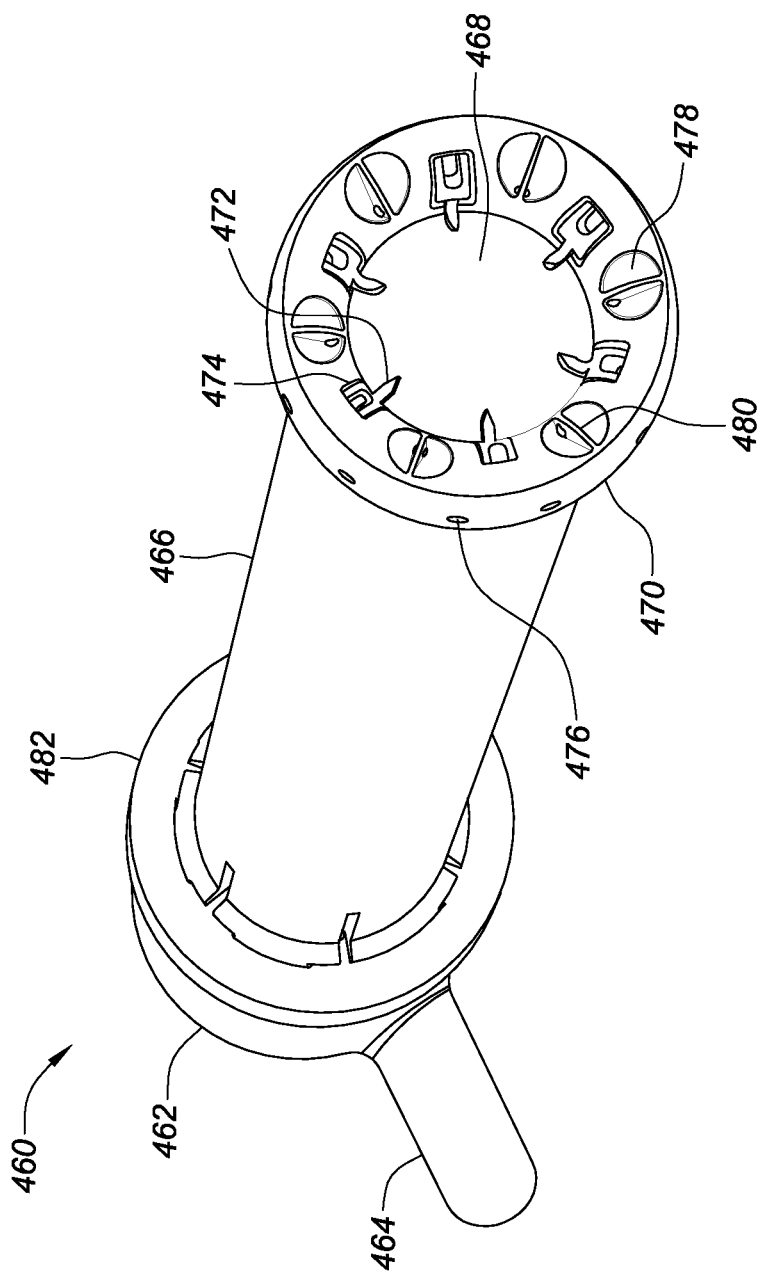
FIG. 13A is an isometric front and side view of a portal access device in a retracted state, in accordance with embodiments of the present disclosure.

FIG. 13A depicts an isometric front and side view of a portal access device in a retracted state, in accordance with embodiments of the present disclosure. In an example, the portal access device 460 can be used in relation with embodiments discussed herein to provide an access pathway into a space within the body. In an example, the portal access device 460 can include a manifold 462 at a proximal end of the portal access device 460. The manifold can include a suction tube 464, as shown in FIG. 13A. A distal end of the manifold 462 can be connected to a proximal end of a central cannula 466. The central cannula 466 can comprise a central lumen 468 that runs through a center of the central cannula 466. In some embodiments, the central lumen 468 can extend through the manifold 462, such that an instrument can be inserted through a proximal end of the manifold 462 distally through the central lumen 468.

In some embodiments, a coupling ring 470 can be connected to a distal end of the central cannula 466. In some embodiments, the coupling ring 470 can have a larger diameter than the central cannula 466. In some embodiments, the coupling ring 470 can include hooks positioned around a distal inner perimeter (e.g., distal face) of the coupling ring 470, as depicted in FIG. 13A. In an example, the hooks 472 can be housed in hook housings 474 formed in a distal face of the coupling ring 470. A number of hook pin bores 476 can be formed in an outer surface of the coupling ring 470. In an example, a pin can be driven into the hook pin bore 476 for each hook 472 and through an opening in each hook 472 to hold the hook 472 in place and allow the hook 472 to rotate about the pin. In some embodiments, hook pin bore 476 can be associated with a hook pin hole for hook 472.

In some embodiments, a distal face of the coupling ring 470 can include a plurality of suction ports 478 spaced around the distal face of the coupling ring 470. In an example, a suction lumen can extend proximally (e.g., through a wall of the central cannula) from each of the suction ports 478 to the manifold 462 and to the suction tube 464. As such, the suction tube 464 can be in fluid communication with each of the suction ports 478 located on the face of the coupling ring 470. In some examples, each of the suction ports 478 can include a suction rib 480 that extends in a radial direction from the central lumen 468. In an example, the suction rib 480 can extend across each suction port 478 to prevent tissue from being sucked into the suction port 478. For instance, the tissue can be draped over the suction port 478, exposing additional surface area of the tissue to the suction drawn through the suction port 478. Thus, a greater suction force can be applied to the tissue with use of the suction rib 480 and/or prevent damage to the tissue caused by the tissue being drawn into the suction port 478.

In some embodiments, the proximal end of the portal access device 460 can be introduced into a patient's chest. The coupling ring 470 can be placed in contact with the pericardium. Once the coupling ring 470 contacts the pericardium, a suction can be drawn through the suction tube 464, thus creating an applied suction at each one of the suction ports 478. The tissue of the pericardium can be sucked into each one of the suction ports 478 and can thus be drawn against the coupling ring 470. With the pericardium in close relation to the proximal surface of the coupling ring 470 due to the suction force applied to the tissue via each one of the suction ports 478, the pericardium can be lifted from the myocardium, in some embodiments. In some embodiments, suction can also be applied in the central lumen 468, which can provide an increased suctional force for lifting the pericardium from the myocardium. In some embodiments, the suction tube can be in fluid communication with the central lumen 468 and/or an additional lumen suction tube can be in fluid communication with the central lumen 468, which can be used to apply suction to the central lumen 468. The hooks 472 can be deployed to penetrate the pericardium and hold it in close relation to the proximal end of the coupling ring 470, as further depicted in the following figures.

In an example, the portal access device 460 can be used to introduce an instrument into the interstitial space between the pericardium and the myocardium. In some embodiments, the portal access device 460 can be used to introduce any one of the devices disclosed in the present disclosure into an interstitial space between the pericardium and the myocardium, as further discussed herein.

Figure 13B:
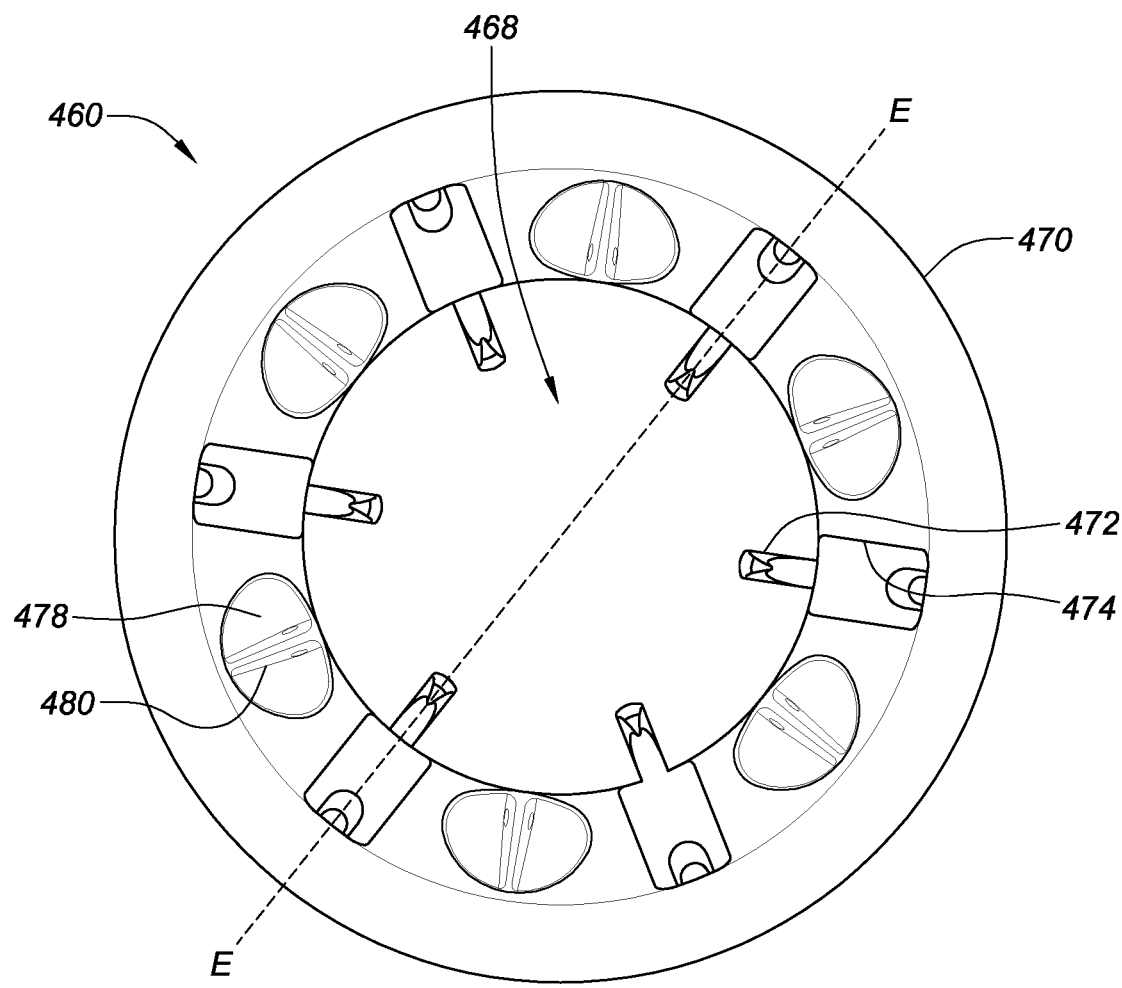
FIG. 13B is a front view of the portal access device in FIG. 13A in the retracted state, in accordance with embodiments of the present disclosure.

FIG. 13B depicts a front view of the portal access device 460 in FIG. 13A in the retracted state, in accordance with embodiments of the present disclosure. As depicted, the portal access device 460 includes the coupling ring that has suction ports 478 dispersed around a distal face of the coupling ring 470. In some embodiments, the hook housings 474 can be formed between the suction ports 478 to hold the hooks 472. In addition, the suction ports 478 can include the suction ribs 480, as discussed herein, which can extend in a radial direction radially from the central lumen 468. Alternatively, the suction ribs 480 can extend across the suction ports 478 in a direction that is tangential to the cylindrical coupling ring 470. In some embodiments, a screen can be placed over each of the suction ports 478 to prevent tissue from being sucked into the suction port 478.

Figure 13C:
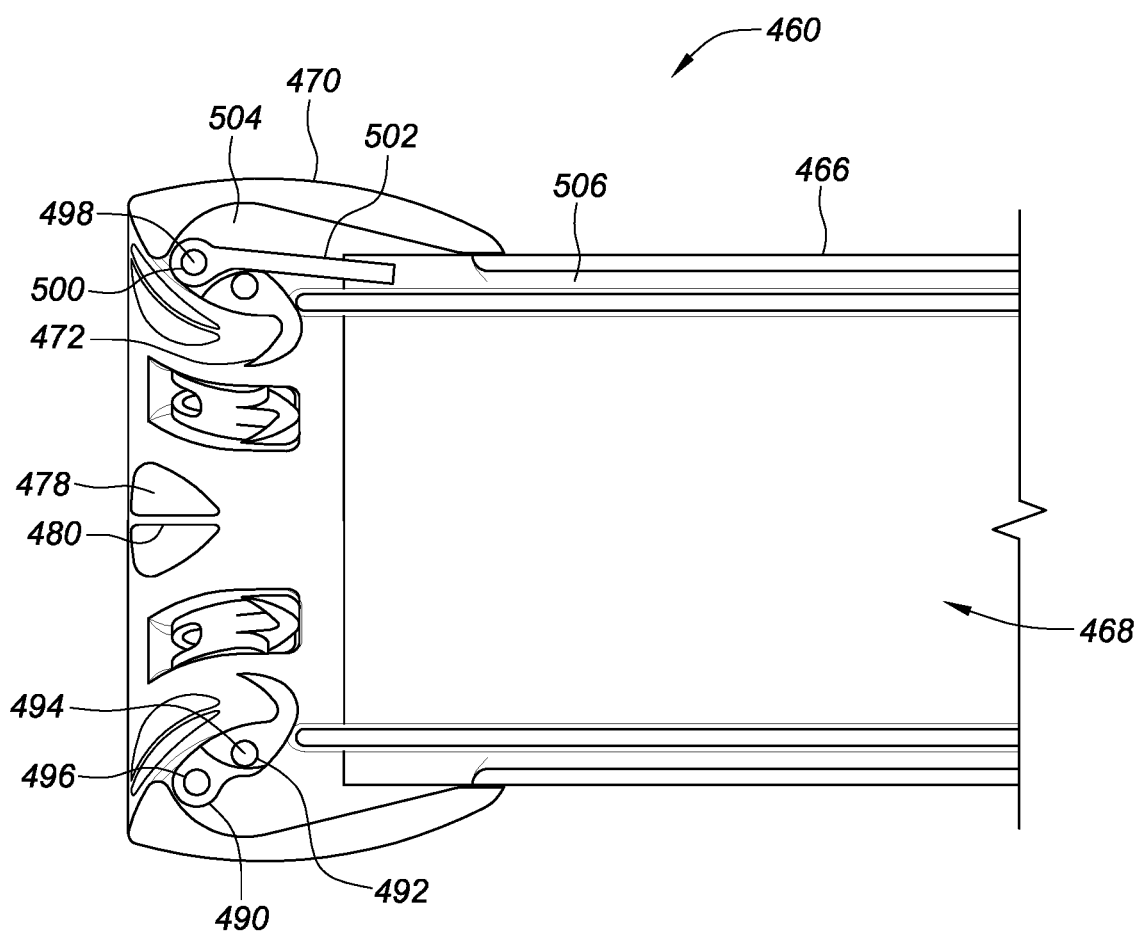
FIG. 13C is a cross-sectional side view of the portal access device in FIG. 13B along line A-A in a retracted state, in accordance with embodiments of the present disclosure.

FIG. 13C depicts a cross-sectional side view of the portal access device 460 in FIG. 13B along line E-E in a retracted state, in accordance with embodiments of the present disclosure. As depicted, the portal access device 460 includes the coupling ring 470 attached to the distal end of the central cannula 466. The cross-sectional view depicts the hooks 472 in a retracted state. Each hook 472 can include a control rod attachment point 490 disposed on an opposite side of a hook pin hole 492. A hook pin 494 can be placed in the hook pin hole 492 via a corresponding hook pin bore 476 to hold the hook pin 494 in place and create a fulcrum point for the hook 472 to rotate about. The control rod attachment point 490 can include a hook fulcrum pin hole 496, through which a control rod pin 498 can pass through to connect a control rod 502 to the hook 472. The control rod 502 can pass through a control rod lumen 506 to the pull ring 482.

In some embodiments, the control rod 502 can extend all the way through the control rod lumen 506 to the pull ring 482. Alternatively, a pull wire can connect the control rod 502 to the pull ring 482. Moving the pull ring 482 distally or proximally can move the control rod 502 distally or proximally, such that the control rod 502 can rotate the control rod attachment point 490 and the hook 472 about the hook pin 494. As such, the hook 472 can be retracted or engaged via movement of the pull ring 482. In some embodiments, the control rod 502 can be connected to another type of device, such as a joy stick, for example. In some embodiments, the coupling ring 470 can include a fulcrum channel 504, as depicted, to allow space for the control rod attachment point 490 to move.

As further depicted, the coupling ring 470 includes the suction port 478 and the suction rib 480 located in the proximal face of the coupling ring. In some embodiments, the distal face of the coupling ring can be contoured from a most distal outer perimeter towards a center of the central lumen. For example, the proximal face can be curved (e.g., radiused), as illustrated.

Figure 13D:
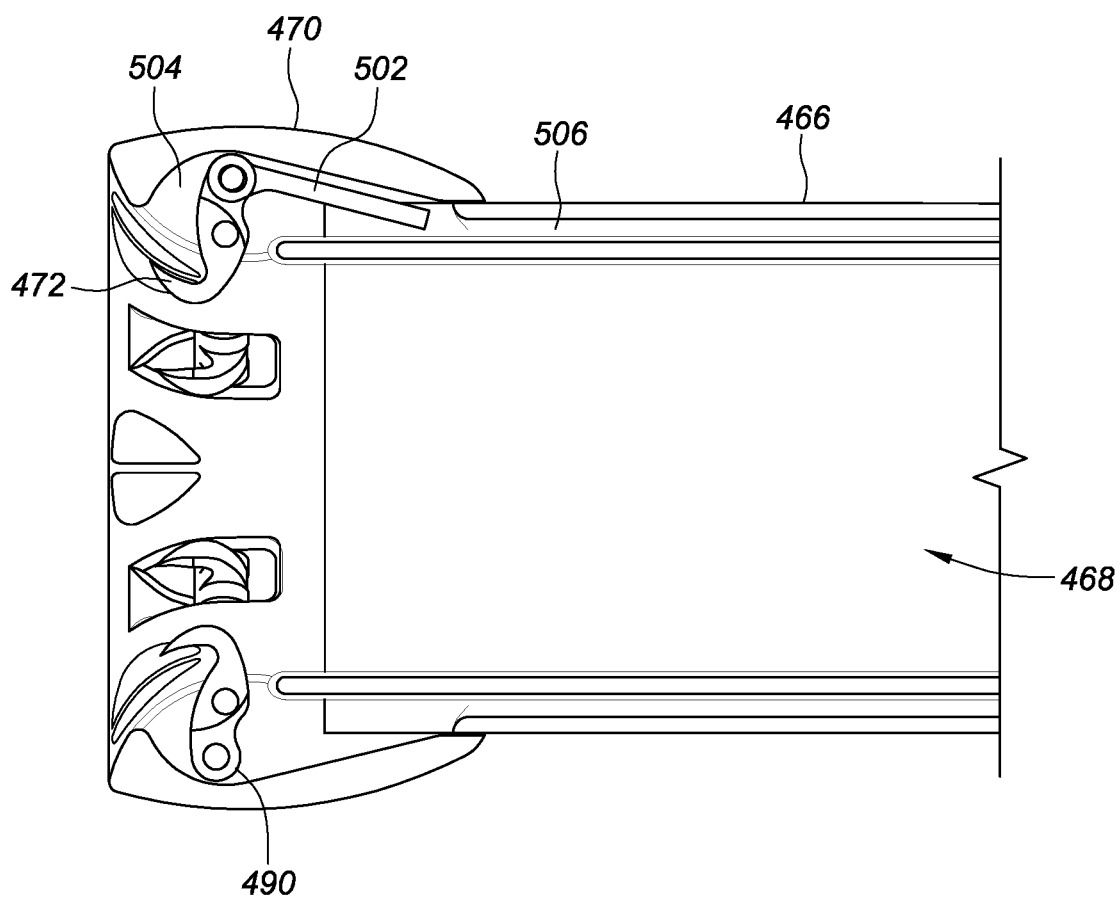
FIG. 13D is a cross-sectional side view of the portal access device in FIG. 13C in a penetrating state, in accordance with embodiments of the present disclosure.

FIG. 13D depicts the cross-sectional side view of the portal access device in FIG. 13C in a penetrating state, in accordance with embodiments of the present disclosure. As depicted, the control rod 502 has been moved proximally toward the control rod lumen 506, thus rotating the hook fulcrum proximally in the fulcrum channel 504, which, in turn has rotated the hook 472 distally towards the distal end of the coupling ring 470 into a penetrating state.

Figure 13E:
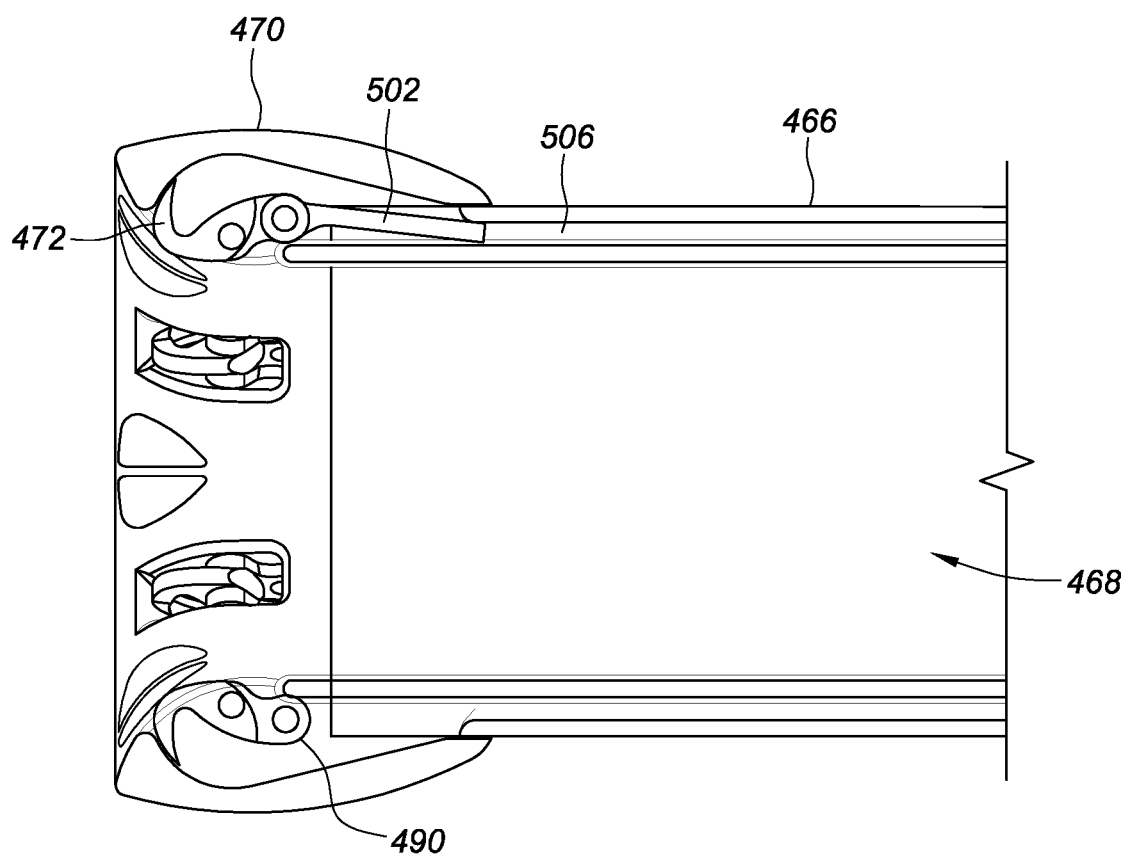
FIG. 13E is a cross-sectional side view of the portal access device in FIG. 13C in an engaged state, in accordance with embodiments of the present disclosure.

FIG. 13E depicts the cross-sectional side view of the portal access device 460 in FIG. 13C in an engaged state, in accordance with embodiments of the present disclosure. As depicted, the control rod 502 has been moved further proximally toward the control rod lumen 506, more fully rotating the control rod attachment point 490 towards a proximal end of the portal access device 460, which, in turn has rotated the hook distally towards the distal end of the coupling ring 470 into an engaged state.

In some embodiments, when the hook 472 is in a penetrating state, grasping the pericardium, the tip of the hook 472 can be configured in relation to the coupling ring 470 to not pass the most distal end of the coupling ring 470. This can be to prevent accidental grasping of the myocardium, in some examples. Through use of the suction ports 478, the pericardium can be sucked into reach of the hooks 472, and the hooks 472 can grasp the pericardium. This can further prevent accidental grasping of the myocardium with the hooks 472, since the pericardium can be sucked into reach of the hooks 472 and in some embodiments pulled from the myocardium, separating the hooks 472 from the myocardium.

Figure 13F:
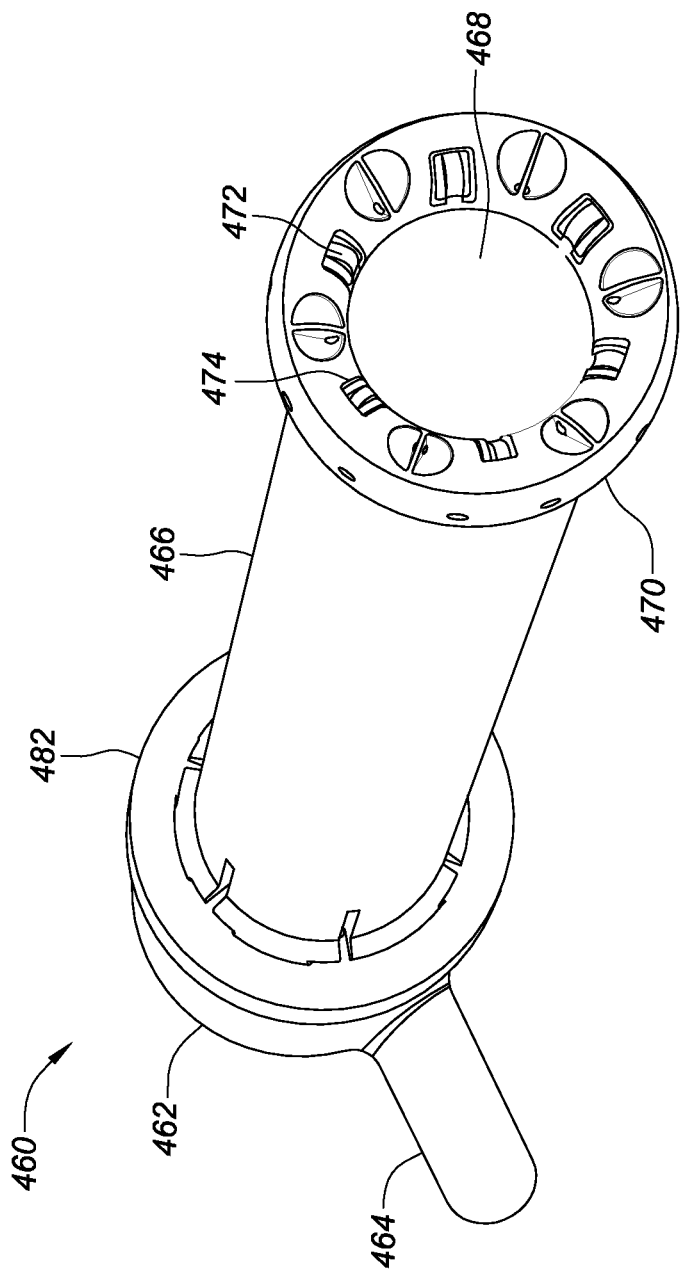
FIG. 13F is an isometric front and side view of the portal access device in FIG. 13A in an engaged state, in accordance with embodiments of the present disclosure.

FIG. 13F depicts an isometric front and side view of the portal access device 460 in FIG. 13A in an engaged state, in accordance with embodiments of the present disclosure. As depicted, the hook 472 can be retracted into the hook housing 474. In some embodiments, the portal access device 460 can be configured to be inserted into the patient using a subxiphoid approach and the coupling ring 470 can be placed into contact with the pericardium via suction, as discussed herein. Alternatively, the portal access device 460 can be attached to the pericardium proper. In some embodiments, the coupling ring 470 can be placed in contact with the apex of the heart. As discussed herein, the pericardium can be suctioned to the coupling ring 470 via the suction ports, the hooks 472 can be engaged to hook and retain the pericardium, and the suction can be turned off.

In some embodiments, the pericardium can be incised with a blade or cautery inserted down the central lumen 468 of the portal access device 460 to create an access port into the interstitial space through the pericardium. In some embodiments, a lumen can extend through a proximal end of the manifold 462 and can be in communication with the central lumen 468. As such, a continuous lumen can pass through the portal access device 460 from a proximal end to a distal end. In some embodiments, the lumen in the manifold 462 can include a seal, through which an instrument can be passed through. For example, a layer of silicon material can be placed across the lumen in the manifold 462 that includes a hole through which an instrument can be passed. As an instrument is inserted in the hole, the silicon can expand and seal around the instrument to prevent any fluid or gas from exiting the manifold 462 of the portal axis device.

In some embodiments, the portal access device can include an insufflation tube that is in communication with the central lumen 468. In an example, when the portal access device 460 has been attached to the pericardium via the hooks 472, an insufflation gas and/or liquid can be pumped in through the insufflation tube and down the central lumen 468 and into the interstitial space in the pericardium. In some embodiments, a flexible seal can be placed around a proximal end of the hook housing 474, which can make contact with the pericardium and help create a seal such that leakage of the insufflation gas and/or liquid can be minimized from the interface between the coupling ring 470 and the pericardium.

In some embodiments, a pair of inflatable rings can be deployed from the coupling ring 470 and/or from a portion of the portal access device 460 adjacent to the coupling ring 470. In an example, an inflatable ring could be deployed within the pericardial sac and a second inflatable ring could be deployed external to the pericardial sac. In an example, the pericardium can be sandwiched by the inflatable rings to help create a seal, such that leakage of the insufflation fluid from between the interface of the coupling ring 470 and the pericardium can be minimized.

In some embodiments the portal access device 460 can include an integral endoscope. The integral endoscope can be placed with the central lumen 468, along one side of the central lumen 468 and/or can be placed within a distal end of the coupling ring 470, in some embodiments.

Figure 14A:
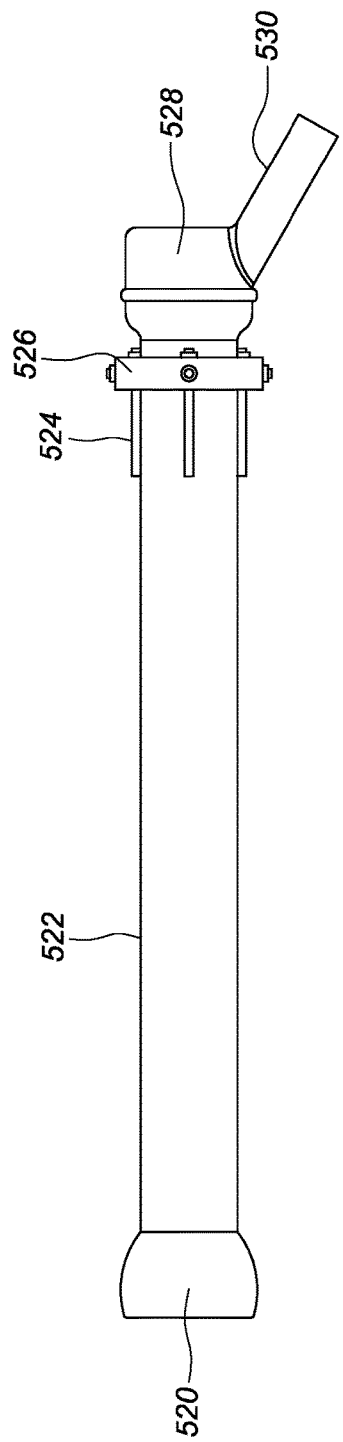
FIGS. 14A to 14C depict various embodiments of a portal access device, in accordance with embodiments of the present disclosure.
Figure 14B:
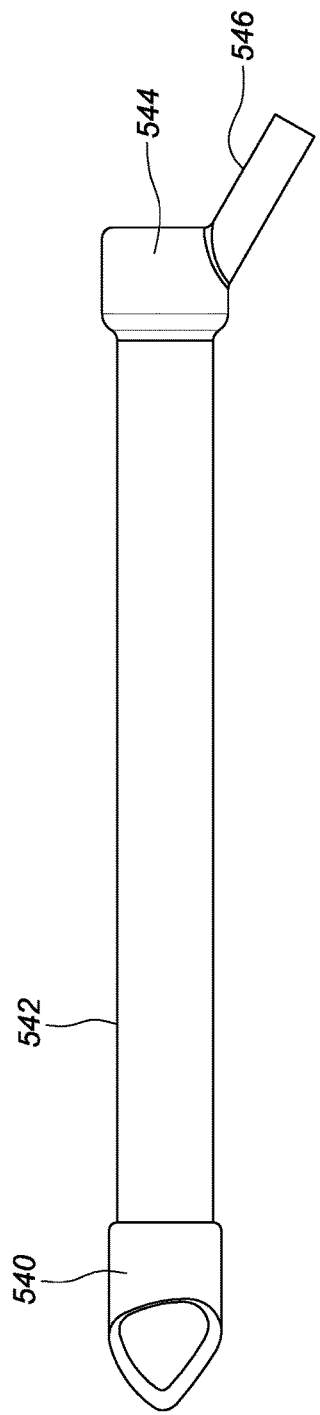
Figure 14C:
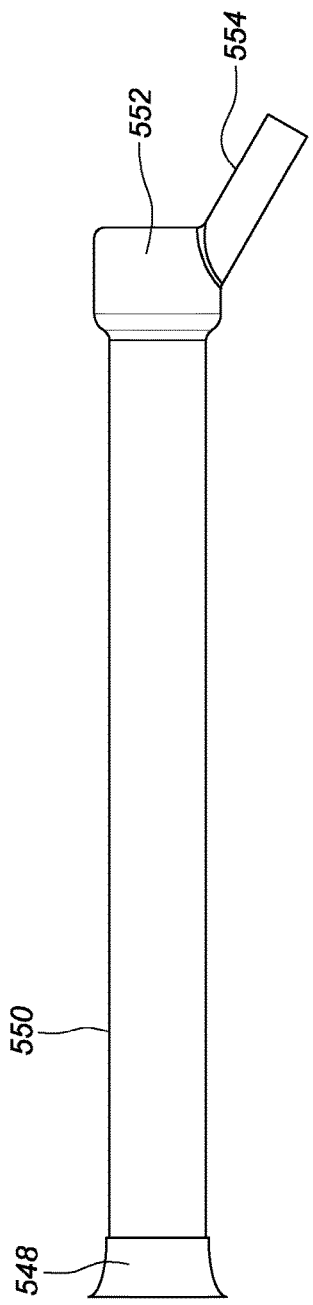

FIGS. 14A to 14C depict various embodiments of the portal access device, in accordance with embodiments of the present disclosure. FIG. 14A depicts an exemplary representation of the portal access device shown in FIG. 13A, including the coupling ring 520, the central cannula 522, control rods 524 for actuating the hooks in the coupling ring 520, and the pull ring 526. In an example, the pull ring 526 can be pulled in a proximal direction and/or pushed in a distal direction (e.g., retracted, protracted) such that each of the control rods are moved equally. Alternatively, the pull ring 526 can be rocked to move the control rods differentially. As such, some of the hooks can be moved a greater amount than or sequentially in relation to other hooks.

Figure 14D:
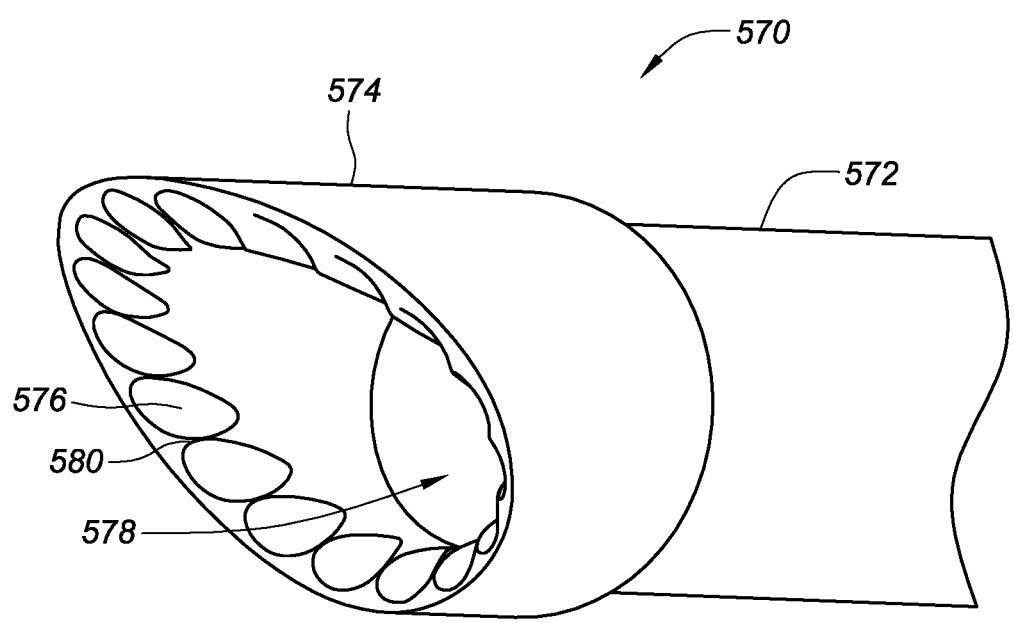
FIG. 14D is an isometric side and front view of the distal end of the portal access device in FIG. 14B, in accordance with embodiments of the present disclosure.

FIG. 14B depicts another embodiment of the portal access device including an angled coupling ring 540, which is further illustrated in FIGS. 14D and 14E. The portal access device in FIG. 14B includes a central cannula 542, manifold 544, and suction tube 546, as previously discussed. Due to the angle formed on the angled coupling ring, hooks may not be employed on the angled coupling ring and the device depicted in FIG. 14B may be a suction device. In some embodiments, larger suction ports may be included in the angled coupling ring 540 and/or a sealing device, as discussed previously, may be used on the angled coupling ring 540 to prevent leakage of insufflation fluid from between an interface between the pericardium and the angled coupling ring. Further aspects of the embodiments depicted in FIG. 14B are discussed and depicted in relation to FIGS. 14D to 14F.

FIG. 14C depicts another embodiment of the portal access device that includes a central cannula 550, a suction tube 554, and a manifold 552. The coupling ring 548 of the portal access device depicted in FIG. 14C does not include hooks, but otherwise employs the suction ports, depicted in FIG. 13A, for example. In some embodiments, the suction ports associated with the embodiments in FIGS. 14B and 14A can be larger in size to provide a greater suction force to lift the pericardium from the myocardium and may or may not include screens and/or suction ribs. Further aspects of the embodiments depicted in FIG. 14C are discussed and depicted in relation to FIGS. 14D to 14F.

FIG. 14D depicts an isometric side and front view of the distal end of the portal access 570 device in FIG. 14B, in accordance with embodiments of the present disclosure. As depicted, the angled coupling ring 574 can be attached to a distal end of the central cannula 572 and can include an angled distal end that includes a plurality of suction ports 576 formed around the distal opening of the angled coupling ring 574. In some embodiments, a distal face of the angled coupling ring 574 can be formed at an angle with respect to the central cannula. In some embodiments, this angle can be in a range from 1 degree to 75 degrees, 10 degrees to 65 degrees, 20 degrees to 55 degrees, 30 to 50 degrees, and/or 35 to 45 degrees, although other ranges of angles are possible. In some embodiments, the distal face of the angled coupling ring 574 can be angled and/or radiused towards the central lumen 578. For example, a surface of the distal face of the angled coupling ring 574 disposed between a distal outer perimeter of the angled coupling ring 574 and an inner perimeter of the angled coupling ring 574 can be angled towards a proximal end of the portal access device. The angled coupling ring can be connected with the distal end of the central cannula.

As further depicted in FIG. 14D, each of the suction ports 576 can be flared open towards a distal end of the angled coupling ring 574. In some embodiments, the suction ports 576 can be equally spaced around the central lumen 578 on a distal surface of the angled coupling ring 574. In some embodiments, the coupling ring 574 can include from 5 to 30, 10 to 25, or 15 to 20 suction ports 576, although fewer than 5 or greater than 30 suction ports 576 can be included in the coupling ring 574. As depicted, the coupling ring 574 includes 17 suction ports 576. In some embodiments, a suction ridge 580 can be formed between adjacent suction ports 576. In an example, a width (e.g., circumferential width) of the suction ridges 580 can be minimized such that suction is applied across a greater surface area of the pericardium. In some embodiments, the suction ridge 580 can be radiused such that as the pericardium is drawn against the distal surface of the angled coupling ring, the pericardium is not cut by the suction ridge 580.

FIG. 14E depicts a diagrammatic side view of the distal end of the portal access device in FIG. 14B, in accordance with embodiments of the present disclosure. As depicted, the angled coupling ring 574 can have a plurality of suction ports 576 disposed around the distal opening of the angled coupling ring 574. The suction ports can be in fluid communication with suction lumens traveling through a wall of the central cannula. For example, suction port 576 can be in fluid communication with suction lumen 578, which can be disposed in an inner wall of the central cannula 572. The suction lumens can be in fluid communication with the suction tube, as previously discussed.

In some embodiments, the suction lumens 578 can be disposed in a wall of the central cannula 572 and the number of suction lumens 578 can equal the number of suction ports. In some embodiments, the central cannula can include one suction lumen and the angled coupling ring 574 can include a manifold that connects each of the suction ports to the one suction lumen. As shown, the angled distal end of the coupling ring 754 can have a curved shape to facilitate an intimate and tangential fit with the surface of the heart (e.g., apex of the heart), in some embodiments. For example, the distal face of the coupling ring 754 can be curved inward towards a proximal end of the portal access device 570 between a distal tip 580 of the angled coupling ring and a distal base of the angled coupling ring 582, as depicted in FIG. 14E. In some embodiments, the distal face of the coupling ring 754 can be perpendicular to a longitudinal axis formed by the central cannula 572, as depicted in FIG. 14C.

Figure 14F:
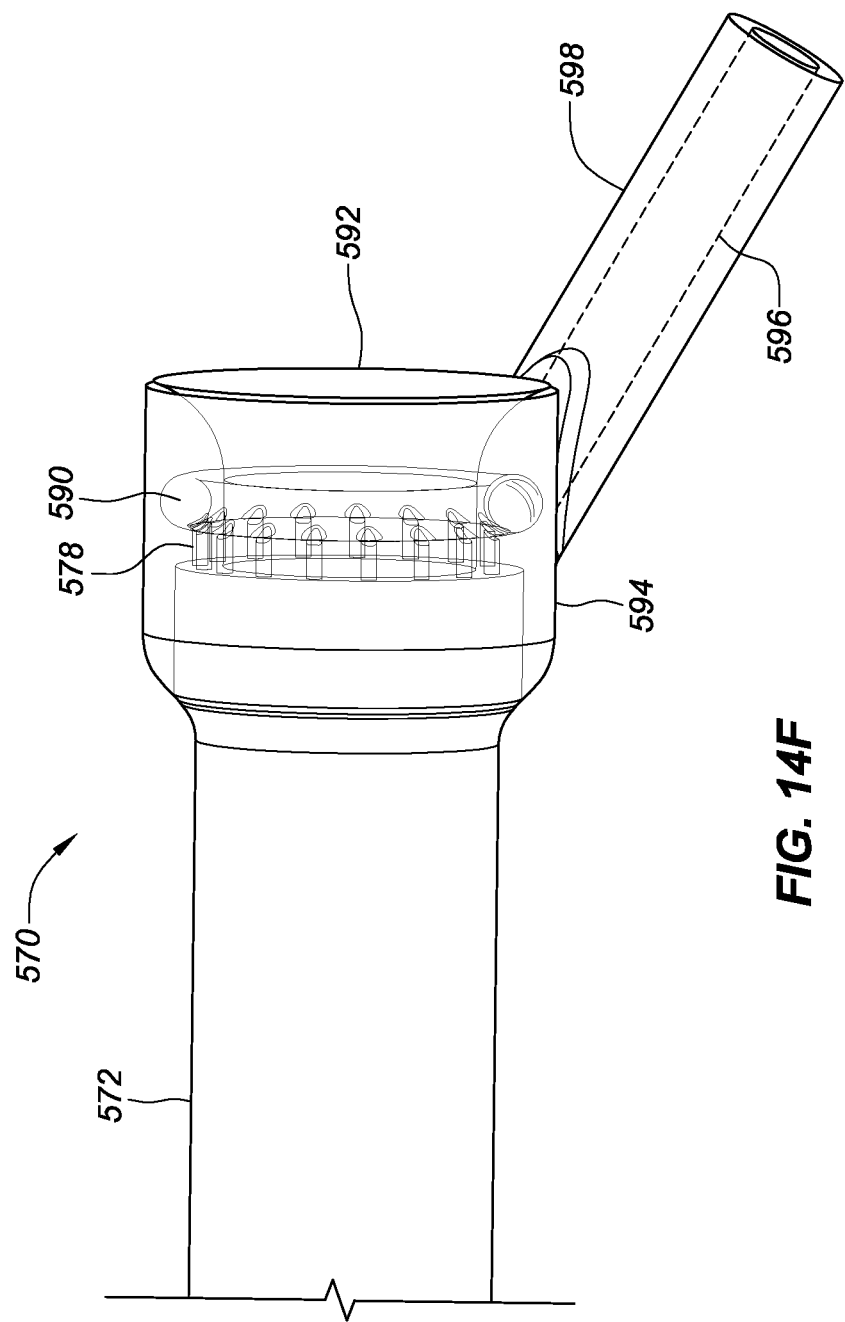
FIG. 14F is an isometric side view of a proximal end of the portal access device in FIG. 13A, in accordance with embodiments of the present disclosure.

FIG. 14F depicts an isometric side view of a proximal end of the portal access device in FIG. 13A to 14F, in accordance with embodiments of the present disclosure. In an example, the portal axis device includes the central cannula 572, to which the manifold 594 is attached to a proximal end. The manifold 594 includes a suction tube 598, which defines a suction tube lumen 596 that is in fluid communication with a suction manifold ring 590 that extends around a circumference of the manifold 594 and is coaxial with an axis extending through the manifold 594 and the central cannula 572. The suction manifold ring 590 is in fluid communication with a plurality of suction lumens 578, which are in fluid communication with the suction ports 576 located at the distal end of the portal access device, as discussed herein. As such, the suction tube lumen 596 is in fluid communication with the suction ports 576. The suction manifold ring 590 can distribute the suction applied through the suction tube lumen 596 substantially equally to the suction ports 576 via the suction manifold ring 590. In some embodiments, the suction manifold ring can be formed in a distal base of the central cannula and/or in a proximal end of the coupling ring, allowing for one or more suction lumens to be disposed in the central cannula, which are in fluid communication with the suction tube lumen 596. In some embodiments, although the suction manifold ring 590 is depicted as a ring shaped lumen, with a circular cross-section, the manifold ring can have a triangular, square, or other shaped cross-section, in some embodiments.

In some embodiments, the manifold ring 590 can be coaxial with a longitudinal axis defined by the portal axis device. The suction lumens can extend parallel to the longitudinal axis, in some embodiments, and can intersect with a distal portion of the manifold ring 590. In some embodiments, the central cannula associated with embodiments depicted in FIGS. 13A to 14F can be flexible and/or have a fixed curve associated therewith, in some embodiments.

The manifold includes a manifold hole, through which various devices can be inserted. In an example, as discussed herein, the manifold hole can include a seal that can prevent or minimize leakage of fluids from the manifold hole.

Figure 15A:
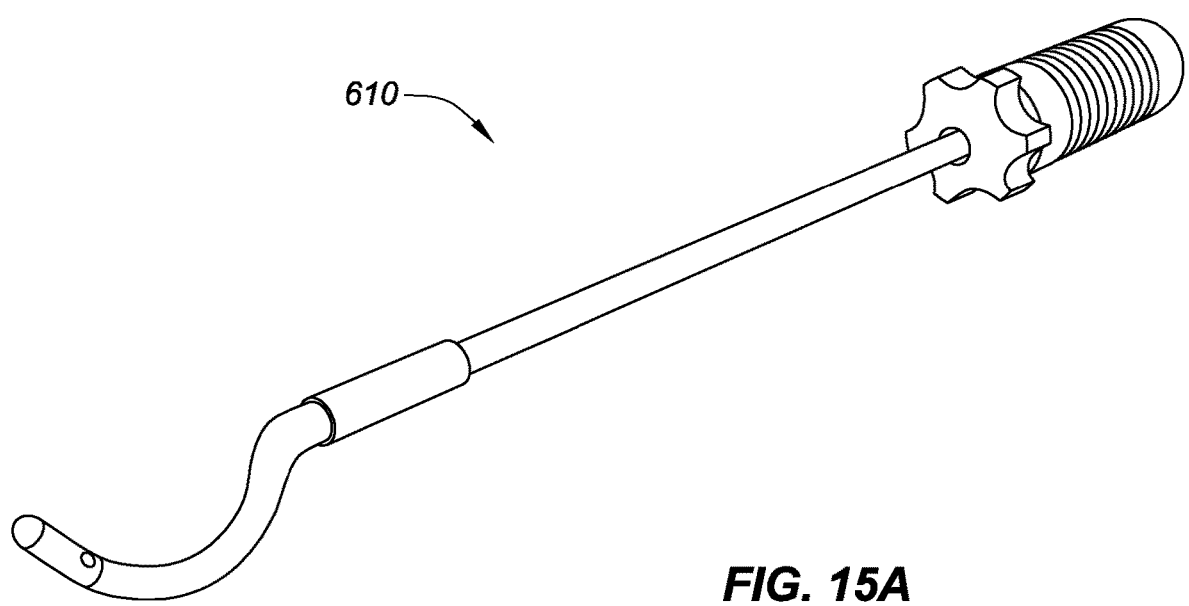
FIG. 15A is an isometric side and front view of an access propagation device in accordance with embodiments of the present disclosure.

FIG. 15A is an isometric side and front view of an access propagation device 610 in accordance with embodiments of the present disclosure. The access propagation device 610 can be similar to a Lumitip™ dissection system, produced by AtriCure. The access propagation device can be used in conjunction with access tape 620, depicted in FIG. 15B. The access tape 620 can have a distal pocket 622 into which a distal tip 624 of the access propagation device 610 can be inserted. For example, the access tape 620 can have a top layer 626 and a bottom layer 628. In an example, a slit can be formed in the top layer 626 of the access tape 620 to form an insertion port 630 into the distal pocket 622. In some embodiments, the distal end of the distal pocket can be formed by sealing the edges of the top layer 626 and the bottom layer 628 together to form a distal port 632 in the access tape 620.

In some embodiments, corners of the distal end of the distal pocket can be sealed to form sealed edges 634-1, 634-2. In some embodiments, the access tape can include a hollow cylindrical magnet 636 inserted into the distal pocket 622, as shown. In some embodiments, as depicted, the hollow cylindrical magnet 636 can be inserted along a longitudinal axis formed by the distal pocket 622, such that a longitudinal axis of the magnet 636 is generally aligned with the longitudinal axis formed by the distal pocket 622. In some embodiments, the distal tip 624 of the access propagation device 610 can be inserted through the insertion port 630, into the distal pocket 622, and into the magnet. In an example, the access propagation device 610 can include a light at the end of the distal tip 624, which can be used for navigation of the access propagation device 610. When the distal tip 624 is inserted into the distal pocket 622 and into the magnet 636, the light from the distal tip 624 can shine through the magnet 636 and out of the distal port 632. As such, by including a hollow cylindrical magnet 636 in the distal pocket 622 and by forming the distal port 632, a light disposed on the distal tip 624 of the access propagation device 610 can shine through the distal port 632, providing light for navigation and/or for retrieval by the access retrieval device 650.

Figure 16:
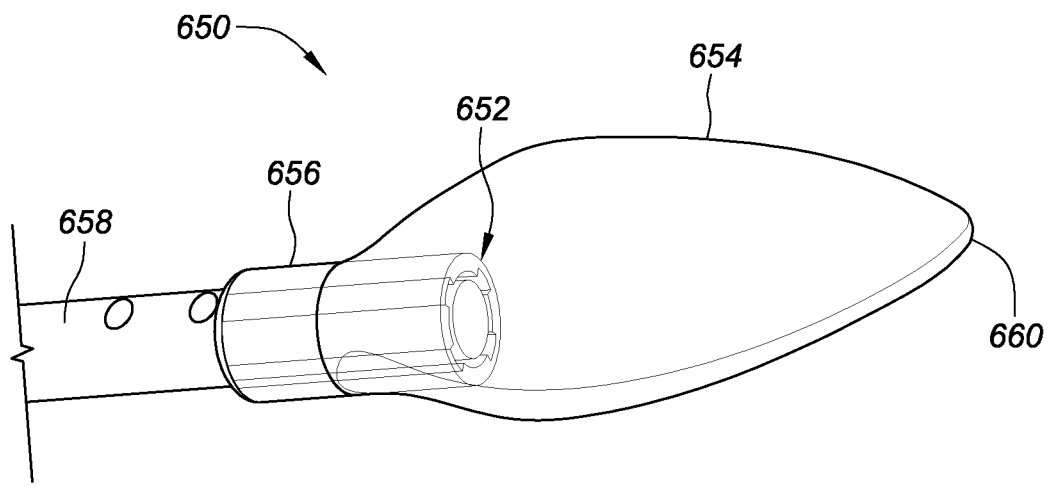
FIG. 16 is an isometric bottom view of an access retrieval device that includes an endoscope hood, in accordance with embodiments of the present disclosure.

FIG. 16 is an isometric bottom view of an access retrieval device 650 that includes an endoscope hood 654, in accordance with embodiments of the present disclosure. The access retrieval device 650 can include a shaft 658 that has a lumen extending there through. In some embodiments, an endoscope 652 can be inserted into a distal end of the shaft 658 and communication lines and/or power can be provided through the lumen extending through the shaft 658. The access retrieval device 650 can include an endoscope hood 654 that includes an endoscope hood mount 656 attached to the distal end of the shaft 658, as depicted.

The endoscope hood 654 can extend distally of the endoscope 652, as depicted and can be formed as a hemispherical pointed dome (e.g., hemispherical distally elongated dome), such that a distal tip 660 of the endoscope hood 654 is pointed, as depicted. In some embodiments, the distal tip 660 of the endoscope hood 654 can be more or less rounded than depicted. In some embodiments, upon insertion of the distal end of the device 650 into the interstitial space between the pericardium and myocardium, the endoscope hood 654 can lift the pericardial sac slightly and create room for the endoscope 652 to capture a field of view that extends distally from the shaft 658. In addition, the endoscope hood 654 can keep material (e.g., fluid, tissue) from contacting a lens of the endoscope 652, thus providing a clear distally facing view.

Figure 15B:
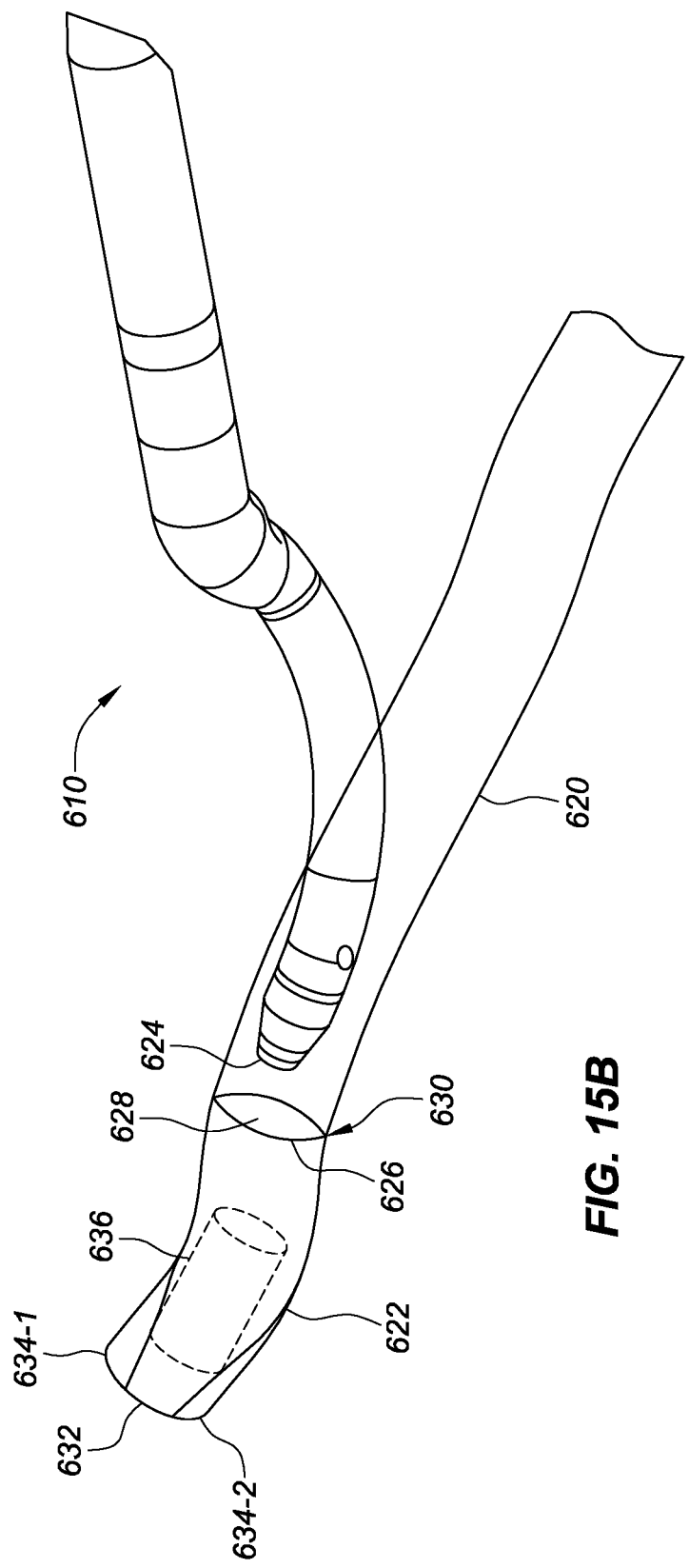
FIG. 15B is a side view of the access propagation device in FIG. 15A being inserted into access tape, in accordance with embodiments of the present disclosure.

In some embodiments, a magnet can be connected to a distal end of the endoscope hood 654, which can be of an opposite polarity in relation to the hollow cylindrical magnet 636 depicted in FIG. 15B. In some embodiments, the magnet can be attached to an interior (e.g., same side as endoscope 652) or an exterior of the endoscope hood 654. In some embodiments, the access retrieval device 650 can be used to retrieve the access tape 620. For example, the opposite polarity magnet on the access retrieval device 650 can attract the hollow cylindrical magnet 636 inserted in the access tape 620 and the magnets can magnetically connect with one another. In some embodiments, the endoscope 652, shielded by the endoscope hood 654 can be used to look for the light produced by the access propagation device 610 to navigate the endoscope hood 654 toward the light to retrieve the magnet and access tape 620 connected with the hollow cylindrical magnet 636.

Figure 17A:
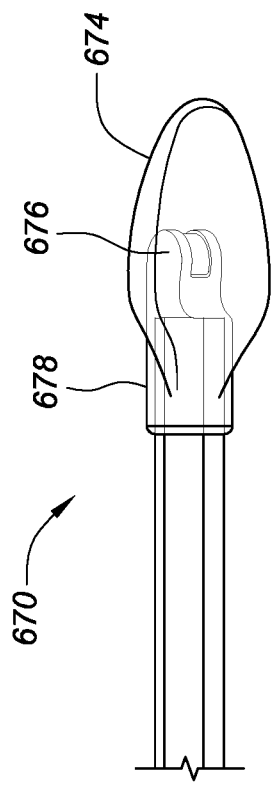
FIG. 17A is an isometric bottom view of an embodiment of an access retrieval device that includes an endoscope hood, in accordance with embodiments of the present disclosure.

FIG. 17A is an isometric bottom view of another embodiment of an access retrieval device 670 that includes an endoscope hood 674, in accordance with embodiments of the present disclosure. As depicted, an endoscope hood 674 similar to that discussed in relation to FIG. 16 can be included on the distal end of a shaft 672. The shaft 672 can house an endoscope 676 at a distal end that can include a rotating view that can be adjusted to look distally through the endoscope hood 674 or below the endoscope hood 674. The endoscope hood 674 can include a mount 678, connecting the endoscope hood 674 to the shaft 672, as discussed herein.

Figure 17B:
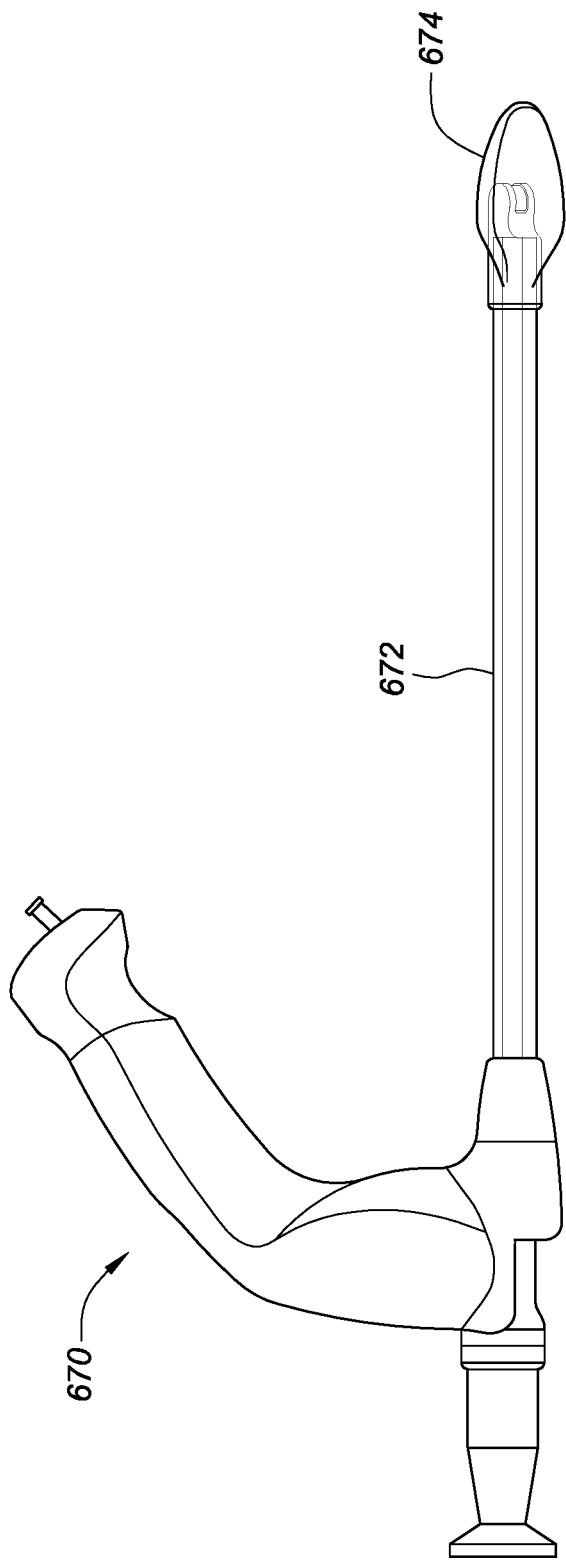
FIG. 17B is an isometric bottom view the access retrieval device that includes the endoscope hood in FIG. 17A, in accordance with embodiments of the present disclosure.

FIG. 17B is an isometric bottom view of another embodiment of a distal end of the access retrieval device depicted in FIG. 17A, in accordance with embodiments of the present disclosure. In an example, an endoscope hood 674 can be included on a distal end of the shaft 672.

Figure 18C:
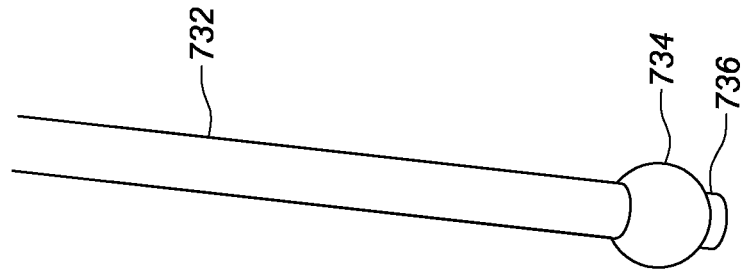
FIGS. 18A to 18C is an isometric bottom view of additional embodiments of an access retrieval device, in accordance with embodiments of the present disclosure.
Figure 18B:
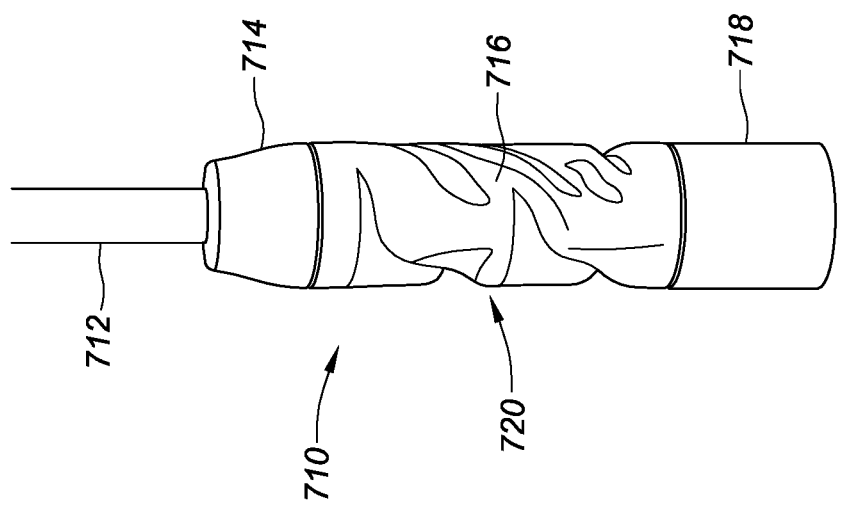
Figure 18A:
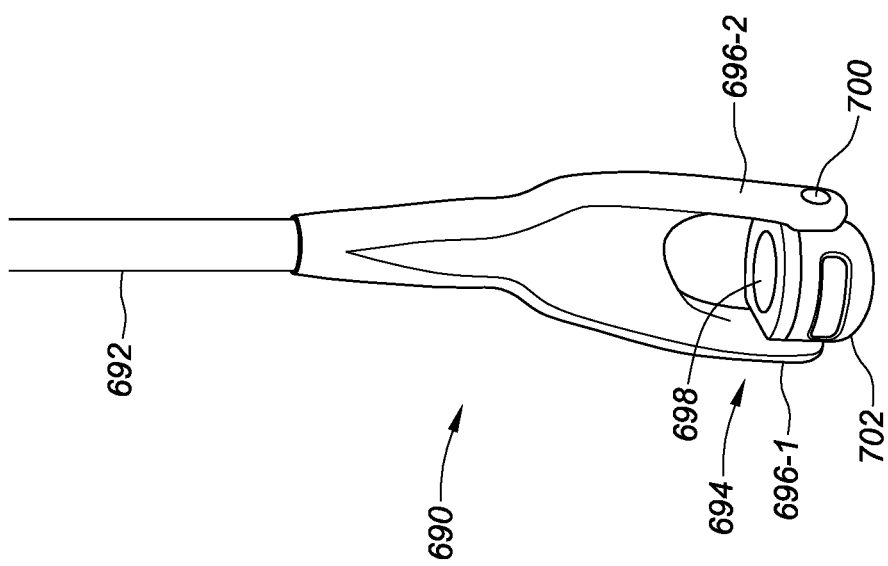

FIGS. 18A to 18C are isometric bottom views of additional embodiments of an access retrieval device, in accordance with embodiments of the present disclosure. FIG. 18A depicts an embodiment of an access retrieval device 690 that includes a shaft 692 with a yoke 694 that includes distally extending yoke arms 696-1, 696-2 attached to a distal end of the shaft 692. A distal end of the yoke 694 can be configured to hold a magnet 698 between two forks (e.g., yoke arms 696-1, 696-2) of the yoke 694 that extend distally. In an example, distal interior walls of the yoke 694 can be parallel to one another.

In some embodiments, the yoke 694 can include holes formed in a distal end of each of the forks that can be configured to accept a swivel pin 700, such that the swivel pin 700 can be inserted through the holes and through a magnet housing. In an example, the holes can be longitudinally aligned and perpendicular to a longitudinal axis defined by the access retrieval device 690 and the shaft 692. In some embodiments, instead of forming holes that extend all the way through each yoke arm 696-1, 696-2, depressions can be made on an interior side of each yoke 694, which can each accept a swivel pin 700 formed on each side of the magnet housing 702. The swivel pins can be diametrically opposed to one another and can extend radially from the magnet housing 702. In some embodiments, the depressions can be made in the magnet housing 702 which can accept a swivel pin 700 formed on the inside of each of the yoke arms 696-1 and 696-2. In some embodiments, the pins cab be integrally formed in either the housing or yoke. Alternatively, an axle can pass through the magnet housing 702, such that tips of the axle are diametrically opposed to one another and extend radially from the magnet housing 702.

In some embodiments, the magnet housing 702 and the yoke 694 can be formed of a polymer, such as a plastic, metal, and/or composite. In some embodiments, the magnet housing 702 can include an open through hole, as depicted in FIG. 18A, which exposes a surface of the magnet 698. In an example, the access retrieval device 690 depicted in FIG. 18A can be used to retrieve the access tape 620 depicted in FIG. 15B, in some embodiments. For instance, the magnet 698 in the distal pocket 622 of the access tape 620 can be magnetically attached to the magnet associated with the access retrieval device 690.

In an example, the magnet 698 is suspended in a yoke 694 at the distal end of the shaft 692 and can be configured to swivel. This allows atraumatic introduction, as the magnet housing 702 has a rounded back end. In some embodiments, the magnet housing 702 can have an elongate shape, which allows for torque transmission to a device being retrieved that has a matching magnet socket to contain the elongate housing. The swivel yoke 694 can allow the magnet 698 and magnet housing 702 to swivel with respect to the yoke 694 as a device being retrieved is being pulled into place. In an example, because the magnet housing 702 and magnet 698 can swivel, an alignment of the device being retrieved can change with respect to the access retrieval device 690, allowing the retrieved device to be pulled into place within a profile of the access retrieval device itself.

The retrieved device can be pulled by the attached magnet but the retrieval device 690 can apply this retrieving force with a pull or a push on its handle depending on whether the distal end of the retrieved device is pointing toward the operator or swiveled around to pointing away from the operator. The transition between the two can be performed around, for instance, the curve of the heart, in one smooth motion: The operator can magnetically attach to the retrieved device that is pointing toward him, in line with the shaft, pull it toward him, then begin a sideways sweep and then push it into a pocket or sinus such as the transverse sinus such that the retrieved device is now pointing away from him and back to parallel with the shaft.

A polarity of the magnet on the device being retrieved can cause automatic alignment of the rotatable distal magnet 698 with respect to the magnet on the device being retrieved as they come into close proximity. The access retrieval device 690 depicted in FIG. 18A can allow for torque transmission to the device being retrieved (if this device has a matching elongate feature that engages with aforementioned elongate retriever housing) when an axis of each device is aligned within about 45° to each other, either pointing forward or trailing. For example, when a longitudinal axis of the shaft is aligned within about 45° of the device being retrieved, the shaft 692 can be turned and torque can be transferred to the device being retrieved.

FIG. 18B depicts an embodiment of an access retrieval device 710 that includes a shaft 712 connected to a proximal end of the access retrieval device 710. In some embodiments, the shaft 712 can be connected to a proximal mount 714 of the access retrieval device 710. The access retrieval device 710 can include a distal tip that includes a magnet socket 718, further depicted in FIG. 18D. The access retrieval device 710 can include a bendable and torqueable section 720 between the proximal mount 714 and the magnet socket 718, which can include a number of universal joints, further depicted in FIG. 18D. The universal joints allow for an angulation between a longitudinal axis of the shaft 712 and the device being retrieved. The universal joints can provide good deflection of the magnetic socket 718, while still allowing for torque transmission deflection angles of 90° or more with respect to a longitudinal axis of the shaft 712. A flexible sleeve 716 can be placed over the bendable and torqueable section to prevent material and/or fluid from contacting or being pinched by internal components of the bendable and torqueable section 720.

FIG. 18C depicts an embodiment of an access retrieval device 730 that includes a shaft 732, a distal end of which is connected to a retrieval ball 734. The retrieval ball 734 can be formed from a material that has a magnetic susceptibility, such that a magnet included on a device being retrieved can be attracted to the retrieval ball 734. In some embodiments, the retrieval ball 734 can be a magnet.

In some embodiments, a separation rod 736 can extend from a proximal end of the shaft 732, through a central lumen of the shaft 732, through the retrieval ball 734, and can exit through a rod port in a distal end of the retrieval ball 734, as depicted. In some embodiments, the rod port can be aligned with a longitudinal axis of the shaft 712 and access retrieval device 730. The separation rod 736 can be deployed by a control connected to the proximal end of the shaft 732, as depicted in FIG. 18F, to separate the access retrieval device 730 and the device being retrieved. For example, the separation rod 736 can separate the retrieval device 730 and the device being retrieved to help reduce a magnetic force between the access retrieval device 730 and the device being removed. Upon reduction of the magnetic force, the access retrieval device 730 can be pulled away from the device being retrieved, while leaving the device being retrieved substantially in place. In a stored state, a distal tip of the separation rod 736 can sit flush, recessed, or slightly raised with respect to a surface of the retrieval ball 734. Upon activation of the control, the separation rod 736 can be moved axially and distally, such that a distal tip of the separation rod 736 is raised from its position in the stored state to a deployed state, thus allowing separation of the access retrieval device 730 from the device being retrieved.

Figure 18D:
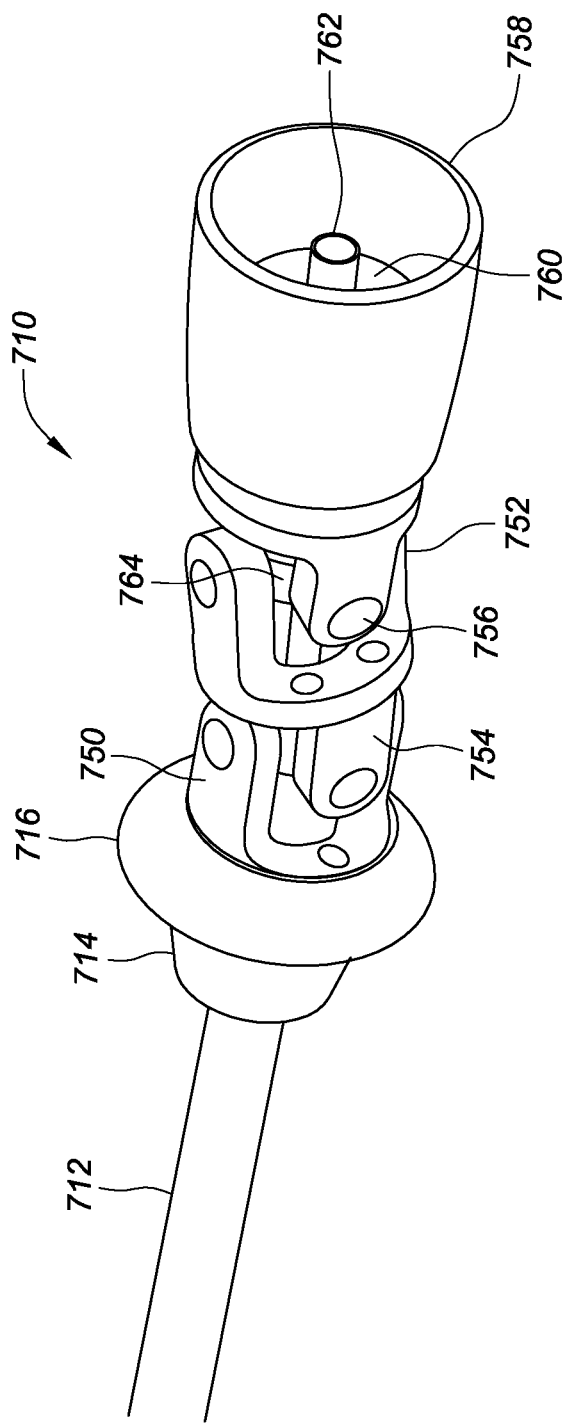
FIG. 18D is an isometric side view of a distal end of the access retrieval device in FIG. 18B, in accordance with embodiments of the present disclosure.

FIG. 18D depicts an isometric side view of a distal end of the access retrieval device 710 in FIG. 18B, in accordance with embodiments of the present disclosure. The access retrieval device 710 can include the shaft 712, the flexible sleeve 716, which has been rolled back in FIG. 18D to expose the internal components of the access retrieval device 710. The shaft 712 can be connected to the proximal mount 714, which is connected to the proximal universal joint 750. In some embodiments, the proximal universal joint 750 can be directly connected to a distal universal joint 752 with a cross journal 764. However, as depicted, the access retrieval device 710 can include N universal joints 754 between the proximal universal joint 750 and the distal universal joint 752, where N can be a number greater than 1. Each of the universal joints 754 can include cross journal holes 756 in which individual journals of each cross journal 764 can be inserted to connect the universal joints 754. The distal universal joint 752 can include an elongate socket 758, which can house a magnet 760 or another magnetically susceptible material. The magnet 760 can have a flat face and can include a rod port that passes through a center of the magnet (e.g., is axially aligned with a longitudinal axis of the magnet 760).

Figure 18E:
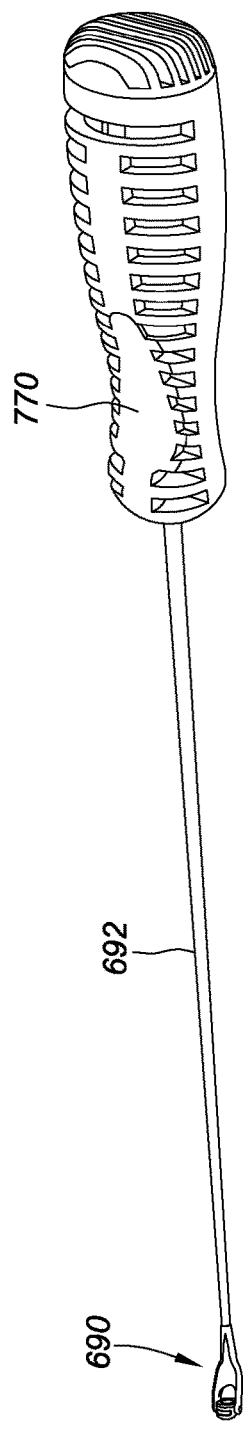
FIGS. 18E to 18G is an isometric bottom view of the additional embodiments of the access retrieval devices depicted in FIGS. 18A to 18C, in accordance with embodiments of the present disclosure.
Figure 18F:
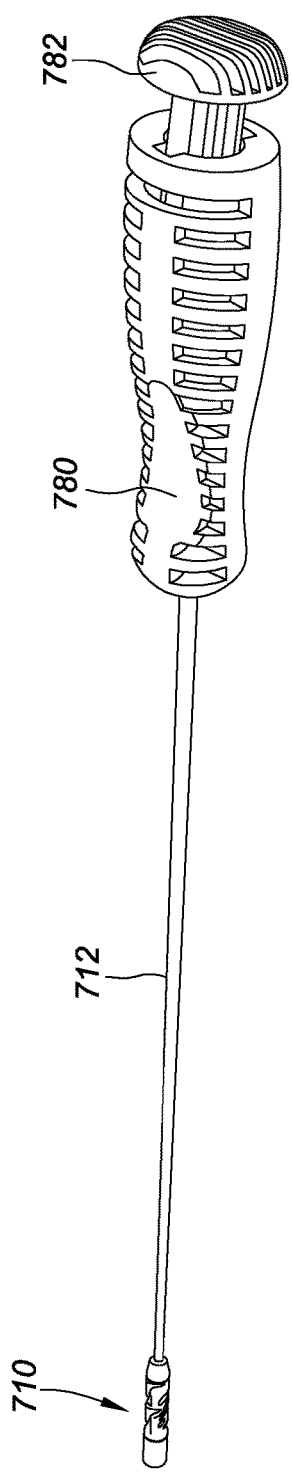

As discussed in relation to FIG. 18C, the separation rod 762 can be deployed by a control connected to the proximal end of the shaft 712, as depicted in FIG. 18E, to separate the access retrieval device 710 and the device being retrieved. For example, the separation rod 762 can separate the retrieval device 710 and the device being retrieved to help reduce a magnetic force between the access retrieval device 710 and the device being removed. In a stored state, a distal tip of the separation rod 762 can sit flush, recessed, or slightly raised with respect to a surface of the magnet 760. Upon activation of the control, the separation rod 762 can be moved axially and distally, such that a distal tip of the separation rod 762 is raised from its position in the stored state to a deployed state, thus allowing separation of the access retrieval device 710 from the device being retrieved.

In some embodiments, the device being retrieved can have a magnet that does not have a hole in its center and can have a flat uninterrupted surface that can be pushed on by the separation rod 762. Alternatively, or in addition, the separation rod 762 can include a push plate or push object connected to its distal end. For example, the push plate can be connected to the distal end of the separation rod 762 so a planar surface of the push plate is parallel with the flat surface of the magnet 760. Thus if the device being retrieved has a magnet with a hole in its center, the push plate can still push on the magnet to separate the devices. Alternatively, the separation rod 762 can have a push object which has a larger diameter than a hole included in the magnet associated with the device being retrieved.

As depicted, the separation rod 762 can travel through a center of the universal joints. The cross journals 764 can each have a hole formed in a middle of each cross journal 764 to allow the separation rod 762 to pass from the distal end of the access retrieval device 710 to the proximal end of the access retrieval device 710. The separation rod 762 can be of sufficient stiffness that it does not fold over as it extends from the magnet in a deployed state, but it does flex going through the cross journals 764, which guide it from bowing outward under compression.

The access retrieval device 710 can include an elongate socket 758 which can accept a mating surface of the device being retrieved (e.g., magnet associated with the device being retrieved). For example, the device being retrieved can slip (e.g., can be configured to fit) inside a lumen formed by the elongate socket 758. Alternatively, the device being retrieved can slip over the elongate socket 758. The elongated socket 758 can aid in transferring torque to the device being retrieved, in some embodiments.

Figure 18G:
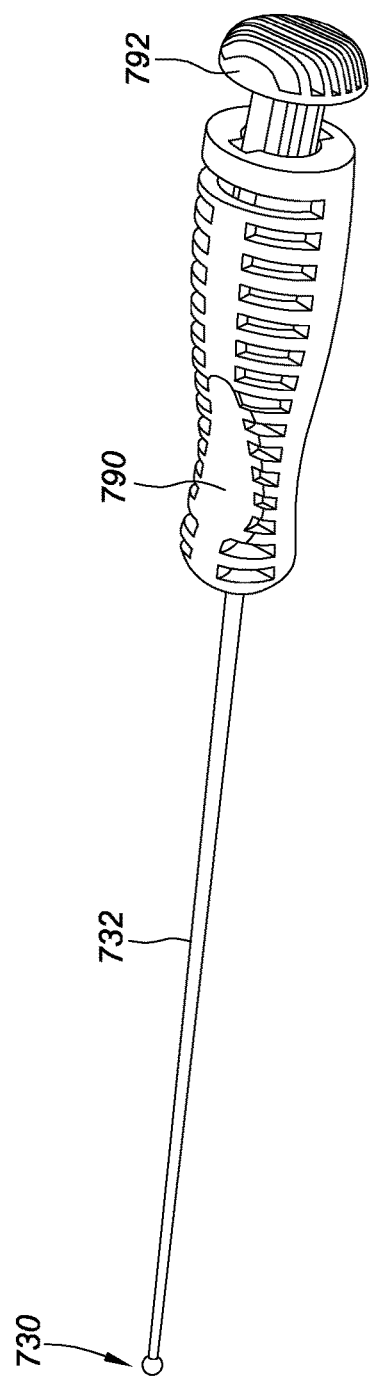

FIGS. 18E to 18G depict isometric bottom views of the additional embodiments of the access retrieval devices depicted in FIGS. 18A to 18C, in accordance with embodiments of the present disclosure. FIG. 18E depicts the handle 770 located at the proximal end of the shaft 772 of the access retrieval device 690 in FIG. 18A. FIG. 18F depicts the handle 780 located at the proximal end of the shaft 712 of the access retrieval device 710 in FIG. 18B. The handle 780 can include a push button control 782 to deploy the separation rod 762. The push button control 782 can be and distally axially depressed, in an embodiment, resulting in the distal extension of the separation rod 762. FIG. 18G depicts the handle 790 located at the proximal end of the shaft 732 of the access retrieval device 730 in FIG. 18C. The handle 790 can include a push button control 792 to deploy the separation rod 736. The push button control can be distally and axially depressed, in an embodiment, resulting in the distal extension of the separation rod 736.

Figure 19A:
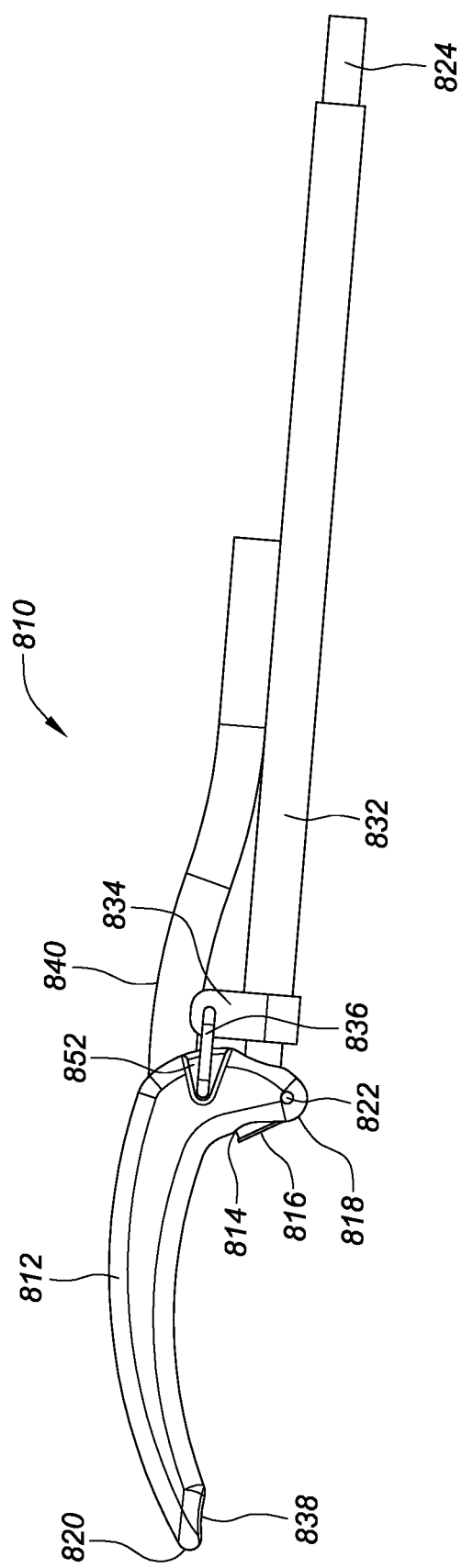
FIG. 19A is a side view of an endoscope hood device, in accordance with embodiments of the present disclosure.

FIG. 19A depicts a side view of an endoscope hood device 810, in accordance with embodiments of the present disclosure. The endoscope hood device 810 can include an endoscope hood 812 that has a port 814 for an endoscope 816 to pass through the endoscope hood 812 at a proximal end of the endoscope hood 812. The endoscope hood 812 can form an arc, beginning at an endoscope proximal base 818 and extending upward and distally from the endoscope 816. The distal portion of the endoscope hood can be curved downward to a distal tip 820 to form the arc, which can reduce a potential for injury upon introduction into anatomic spaces, tissue planes, and interstitial space such as the intrapericardial space. An endoscope proximal base 818 of the endoscope hood 812 can include a hinge pin slot, through which a hinge pin 822 can pass through. The hinge pin 822 can pass through an endoscope base 830, as depicted in FIG. 19C, which can be connected around a distal end of the endoscope 816 and/or distal end of an inner tube 824. The endoscope proximal base 818 can have a vertical relief slot 850, allowing it to be slipped over the endoscope 816 and/or inner tube 824 and fastened so it does not move axially.

The endoscope 816 can be positioned at a distal end of an inner tube 824, in some embodiments. In some embodiments, the inner tube 824 can be a shaft associated with the endoscope. A push/pull tube 832 can be coaxial with the inner tube 824 and can be slid axially along the inner tube 824 (e.g., protracted, retracted) to move the endoscope hood 812. A distal end of the push/pull tube 832 can include a push/pull plate 834, which extends vertically from the push pull tube 832 and can be connected to the endoscope hood 812 via a hinge wire 836, as depicted.

In an example, as the push/pull tube 832 is moved axially and distally (e.g., protracted), the endoscope hood 812 can be deflected downward. As the push/pull tube is moved axially and proximally (e.g., retracted), the endoscope hood 812 can be deflected upward. For example, by protracting the push/pull tube 832 with respect to the inner tube 824, the push/pull plate 834 can be moved distally, thus causing the hinge pin 836 to translate the distal motion to the endoscope hood 812, to which it can be rotatably connected (e.g., can pass through a hinge pin hole in the push/pull plate 834 and a hinge pin hole in the endoscope hood 812). In some embodiments, a relief slot 852 can be formed around a hinge pin hole disposed in the endoscope hood 812, such that the endoscope hood 812 can be deflected upward and downward without the hinge pin 836 contacting the endoscope hood 812. Upon translation of the distal motion to the endoscope hood 812, the endoscope hood 812 can rotate about the hinge pin 822, causing the endoscope hood (e.g., distal tip 820) to move (e.g., deflect) upwardly or downwardly.

In some embodiments, the endoscope hood 812 can include a fluid port 838 that is in fluid communication with a fluid lumen 842 defined by a fluid tube 840 via a fluid lumen 844 extending through the endoscope hood 812. In some embodiments, the fluid tube 840 can be inserted into a recessed tube mounting bore 846 that has a diameter that closely matches that of the fluid tube 840. In some embodiments, a diameter of the fluid lumen 844 can be less than the recessed tube mounting bore 846. In an example, irrigation liquid can be expelled from the fluid port 838, a gas can be expelled from the fluid port 838 for insufflation, and/or a vacuum can be drawn through the fluid port 838. The endoscope hood device 810 can have the ability to tent the pericardium while providing the ability to flush a field of view of the endoscope 816 with fluid, clear the field via vacuum, and/or gently grasp structures such as the pericardium for incision or left atrial appendage to assist with a deployment of a clip at its base, in some examples. The ability to gently tease the left atrial appendage into a clip, such as an AtriClip®, produced by AtriCure, without an extra tool, such as a kitner or graspers can simplify a procedure and minimize a number of instruments to be handled.

Figure 19B:
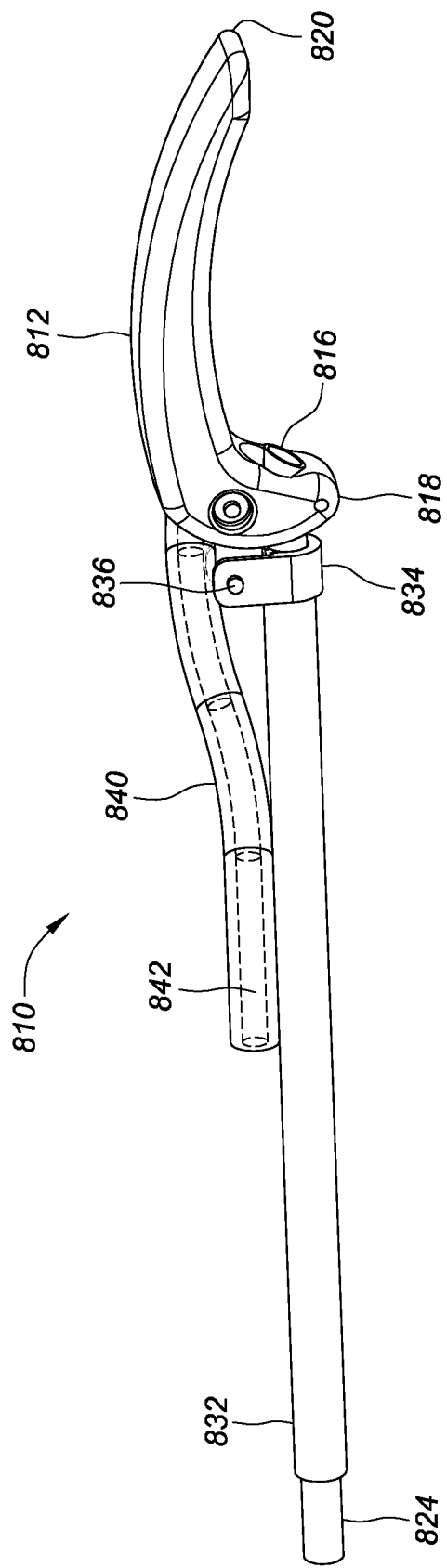
FIG. 19B is an isometric side view of the endoscope hood device in FIG. 19A, in accordance with embodiments of the present disclosure.
Figure 19C:
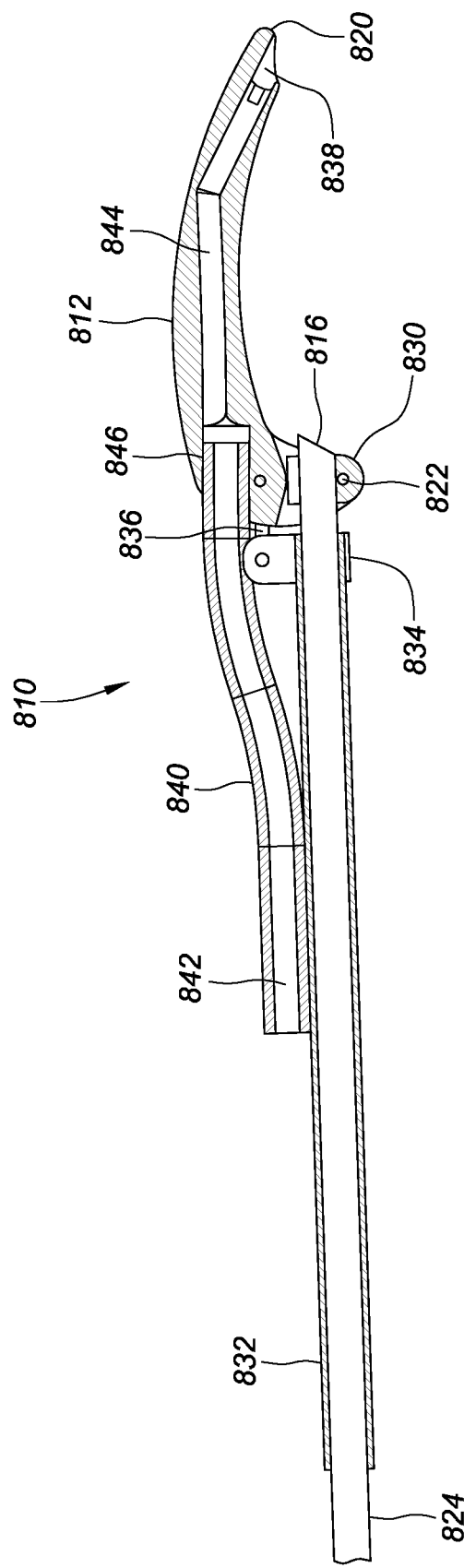
FIG. 19C is a cross-sectional side view of the endoscope hood device in FIG. 19A, in accordance with embodiments of the present disclosure.
Figure 19D:
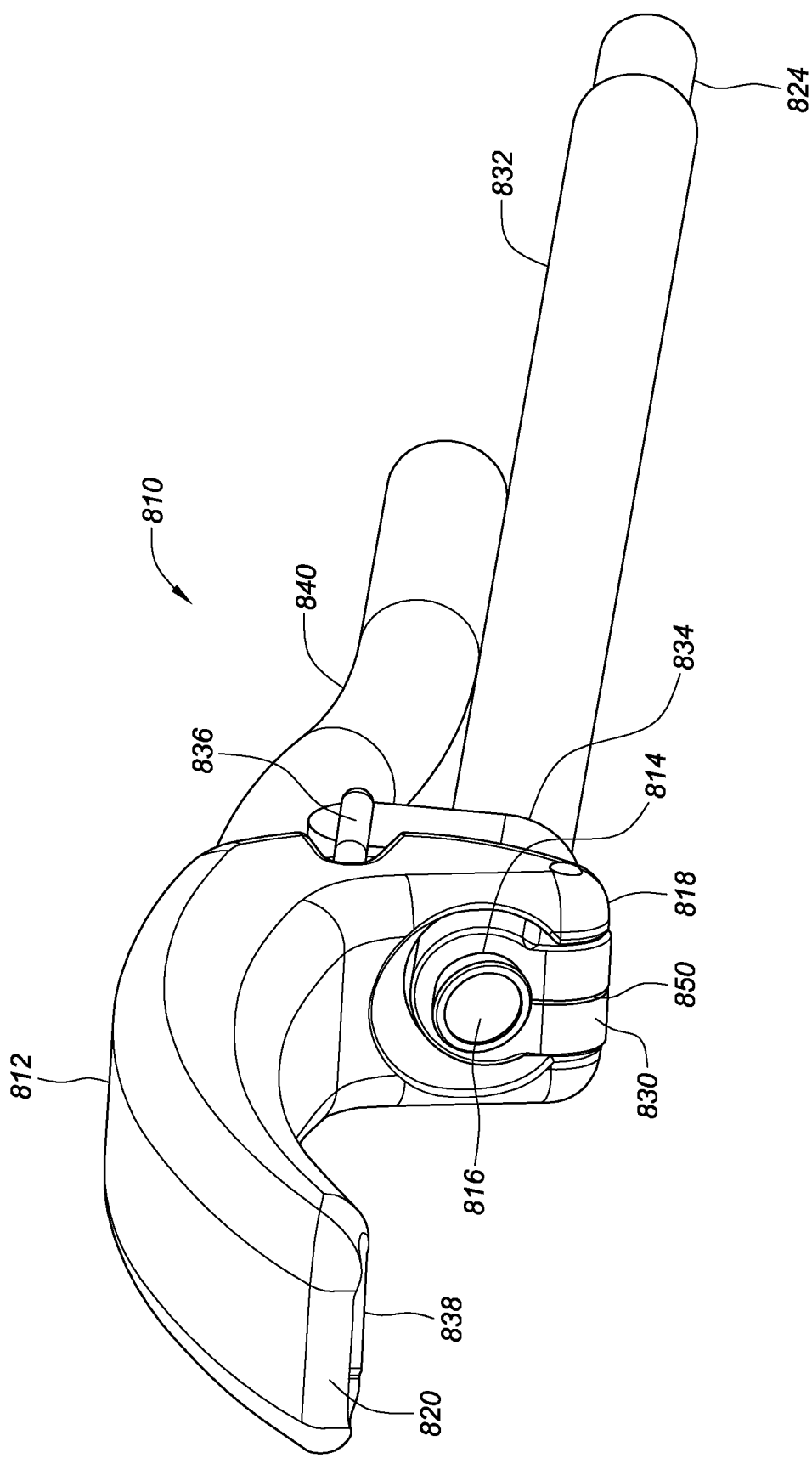
FIG. 19D is an isometric front and side view of the endoscope hood device in FIG. 19A, in accordance with embodiments of the present disclosure.
Figure 19E:
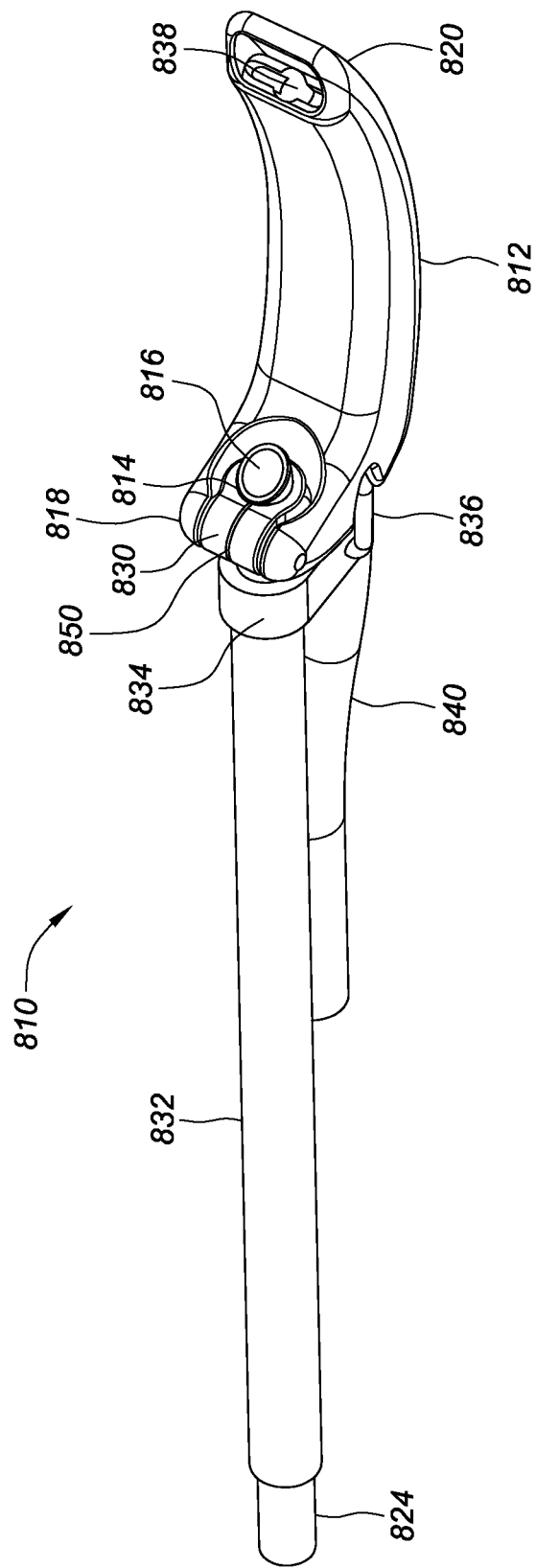
FIG. 19E is an isometric bottom, front, and side view of the endoscope hood device in FIG. 19A, in accordance with embodiments of the present disclosure.

FIG. 19B depicts an isometric side view of the endoscope hood device 810 in FIG. 19A, in accordance with embodiments of the present disclosure. An opposite side of the endoscope hood device 810 is depicted in FIG. 19B in relation to the view depicted in FIG. 19A. FIG. 19C depicts a cross-sectional side view of the endoscope hood device 810 in FIG. 19A, in accordance with embodiments of the present disclosure. As shown, the endoscope hood 812 can include an inner lumen 844 that connects the fluid port 838 with the fluid tube 840. FIG. 19D depicts an isometric front and side view of the endoscope hood device 810 in FIG. 19A, in accordance with embodiments of the present disclosure. As depicted, the endoscope base 830 can include the vertical relief slot 850, as previously discussed herein. FIG. 19E depicts an isometric bottom, front, and side view of the endoscope hood device 810 in FIG. 19A, in accordance with embodiments of the present disclosure.

Figure 19F:
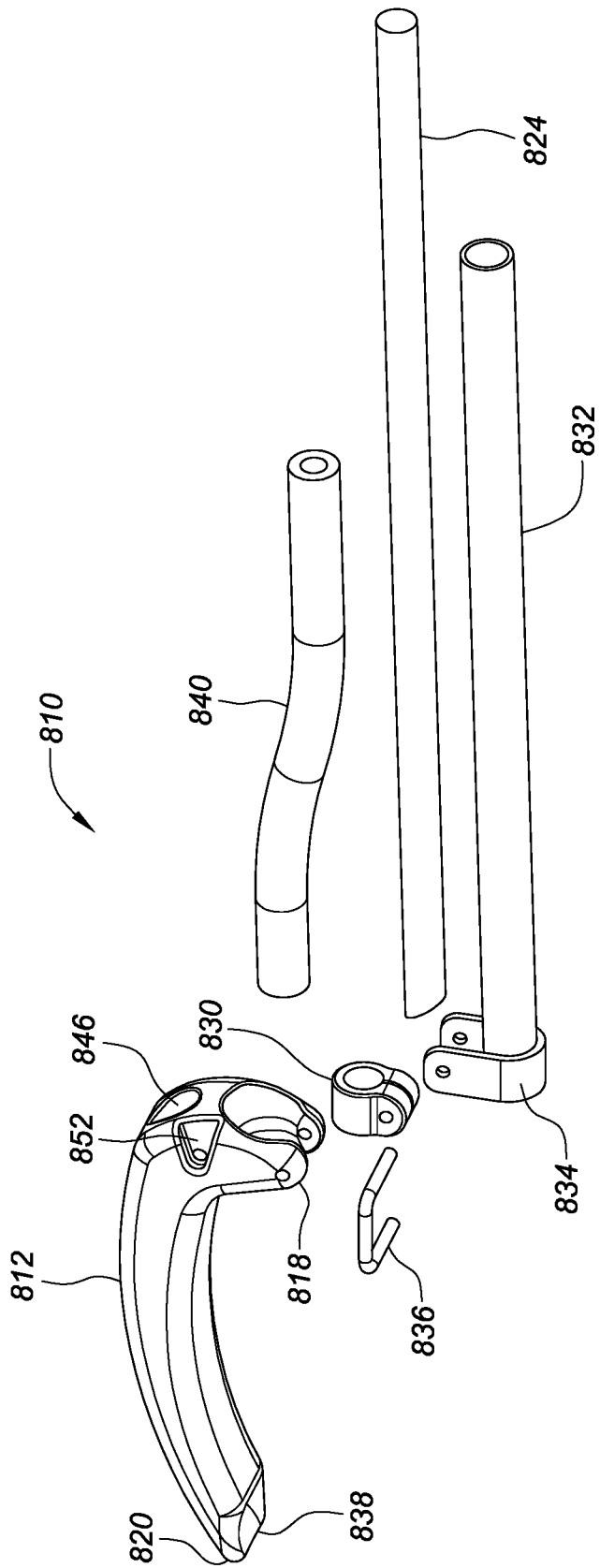
FIG. 19F is an isometric bottom and side component view of the endoscope hood device in FIG. 19A, in accordance with embodiments of the present disclosure.

FIG. 19F depicts an isometric bottom and side component view of the endoscope hood device 810 in FIG. 19A, in accordance with embodiments of the present disclosure. As discussed herein, the endoscope hood device 810 can include the endoscope hood 812, the endoscope base 830, the fluid tube 840, the hinge pin 822, the push/pull tube 832, and the inner tube 824, which can house the endoscope 816 at its distal end.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the endoscope of the embodiments, the endoscope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for determination of a medical device has been described above with a certain degree of particularity, those skilled in the art could make numerous alterations to the disclosed embodiments without departing from the spirit or endoscope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method of using a medical device, comprising: deploying a first guidewire distal looped portion and a second guidewire distal looped portion of the medical device from a distal end of an elongate outer sheath that extends along a sheath longitudinal axis and defines a central lumen extending therethrough; guiding an occlusion device disposed at a distal end of an elongate flexible shaft along the first guidewire distal looped portion and the second guidewire distal looped portion; and activating the occlusion device via a control disposed proximally of the distal end of the elongate outer sheath, wherein the occlusion device includes a top support jaw and a bottom support jaw and activating the occlusion device includes closing the top support jaw and the bottom support jaw.

2. The method of claim 1, wherein the method includes guiding the occlusion device from a straight orientation, the straight orientation being aligned with the sheath longitudinal axis, by causing the occlusion device to be moved distally about the first and second distal looped portions.

3. The method of claim 2, wherein activating the occlusion device includes causing a first jaw and a second jaw of the occlusion device to be opened, wherein a first guide lumen through which the first guidewire distal looped portion passes is connected to the first jaw and a second guide lumen through which the second guidewire distal looped portion passes is connected to the second jaw.

4. The method of claim 1, wherein deploying the first guidewire distal looped portion and the second guidewire distal looped portion from the distal end of the elongate outer sheath includes laterally expanding the first guidewire distal looped portion and the second guidewire distal looped portion with respect to the sheath longitudinal axis.

5. The method of claim 1, wherein guiding the occlusion device includes guiding the occlusion device from an orientation that is aligned with the sheath longitudinal axis toward an orientation that is perpendicular with the sheath longitudinal axis.

6. The method of claim 1, wherein the occlusion device includes a clip hinge and closing the top support jaw and the bottom support jaw includes pivoting at least one of the top support jaw and the bottom support jaw about the clip hinge.

7. The method of claim 1, wherein guiding the occlusion device along the first guidewire distal looped portion and the second guidewire distal looped portion includes guiding the occlusion device along the first guidewire distal looped portion via a top guide that defines a top guide lumen and guiding the occlusion device along the second guidewire distal looped portion via a bottom guide that defines a bottom guide lumen.

8. The method of claim 1, wherein guiding the occlusion device along the first guidewire distal looped portion and the second guidewire distal looped portion includes pushing the elongate flexible shaft distally with respect to the elongate outer sheath.

9. The method of claim 1, wherein the occlusion device includes a first support jaw and a second support jaw and guiding the occlusion device includes guiding the first support jaw distally along the first guidewire distal looped end and guiding the second support jaw distally along the second guidewire distal looped end.

10. The method of claim 9, further comprising turning the first support jaw and the second support jaw from a straight orientation aligned with the sheath longitudinal axis, as the first support jaw and the second support jaw are moved distally along the first and second guidewire distal looped ends.

11. The method of claim 1, further comprising deploying an endoscope from the distal end of the elongate outer sheath.

12. A method of using a medical device, comprising: deploying a first guidewire distal looped portion and a second guidewire distal looped portion of the medical device from a distal end of an elongate outer sheath that extends along a sheath longitudinal axis and defines a central lumen extending therethrough; guiding an occlusion device disposed at a distal end of an elongate flexible shaft along the first guidewire distal looped portion and the second guidewire distal looped portion, wherein the occlusion device is guided from an orientation that is aligned with the sheath longitudinal axis towards an orientation that is perpendicular with the sheath longitudinal axis; and activating the occlusion device via a control disposed proximally of the distal end of the elongate outer sheath, wherein activating the occlusion device includes activating the occlusion device via a control disposed at a proximal end of the elongate outer sheath, wherein activating the occlusion device includes causing a first jaw and a second jaw to move with respect to one another, upon actuation of the control disposed at the proximal end of the elongate outer sheath.

13. The method of claim 12, wherein activating the occlusion device includes activating electrodes disposed on the first jaw and the second jaw of the occlusion device.

14. A method of using a medical device, comprising:
deploying a first guidewire distal looped portion and a second guidewire distal looped portion of the medical device from a distal end of an elongate outer sheath that extends along a sheath longitudinal axis and defines a central lumen extending therethrough;
guiding an occlusion device disposed at a distal end of an elongate flexible shaft along the first guidewire distal looped portion and the second guidewire distal looped portion, wherein the occlusion device is guided from an orientation that is aligned with the sheath longitudinal axis towards an orientation that is perpendicular with the sheath longitudinal axis; and
activating the occlusion device via a control disposed proximally of the distal end of the elongate outer sheath, wherein activating the occlusion device includes causing a first jaw and a second jaw of the occlusion device to be opened.

15. The method of claim 14, wherein guiding the occlusion device includes guiding the occlusion device along the first and second guidewire distal looped portion via a pair of guide lumens defined on the occlusion device.

16. The method of claim 15, wherein the occlusion device includes a top jaw and a bottom jaw and a first one of the pair of guide lumens is disposed on the bottom jaw and the second one of the pair of guide lumens is disposed on the top jaw, and wherein guiding the occlusion device includes guiding the first guidewire distal looped end through the first guide lumen and guiding the second guidewire distal end through the second guide lumen.

17. The method of claim 14, further comprising deploying a visualization device between the first guidewire distal looped portion and the second guidewire distal looped portion.

\* \* \* \* \*